(12) United States Patent
Ehrlich et al.

(10) Patent No.: US 11,348,690 B2
(45) Date of Patent: *May 31, 2022

(54) METHODS AND SYSTEMS OF PRIORITIZING TREATMENTS, VACCINATION, TESTING AND/OR ACTIVITIES WHILE PROTECTING THE PRIVACY OF INDIVIDUALS

(71) Applicants: Gal Ehrlich, Ramat-Gan (IL); Maier Fenster, Petach-Tikva (IL)

(72) Inventors: Gal Ehrlich, Ramat-Gan (IL); Maier Fenster, Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/386,606

(22) Filed: Jul. 28, 2021

(65) Prior Publication Data

US 2022/0005610 A1    Jan. 6, 2022

Related U.S. Application Data

(63) Continuation of application No. 17/106,279, filed on Nov. 30, 2020, now Pat. No. 11,107,588.

(30) Foreign Application Priority Data

| Aug. 11, 2020 | (IL) | 276648 |
| Aug. 11, 2020 | (IL) | 276665 |
| Sep. 1, 2020 | (IL) | 277083 |

(51) Int. Cl.
*G06Q 10/00* (2012.01)
*G16H 50/80* (2018.01)
(Continued)

(52) U.S. Cl.
CPC ............ *G16H 50/80* (2018.01); *G06N 7/005* (2013.01); *G16H 50/30* (2018.01); *H04W 4/023* (2013.01); *H04W 4/029* (2018.02)

(58) Field of Classification Search
CPC ........ G16H 50/80; G16H 50/30; G16H 15/00; G16H 10/60; G06N 7/005; H04W 4/023;
(Continued)

(56) References Cited

U.S. PATENT DOCUMENTS 7,705,723 B2    4/2010 Kahn et al.
8,645,538 B2    2/2014 Pan
(Continued)

FOREIGN PATENT DOCUMENTS

WO    WO 2022/034572    2/2022

OTHER PUBLICATIONS

Interview Summary dated Apr. 9, 2021 From the US Patent and Trademark Office Re. U.S. Appl. No. 17/106,279. (2 Pages).
(Continued)

*Primary Examiner* — Anh V La

(57) ABSTRACT

System and methods for anonymously selecting subjects for treatment against an infectious disease caused by a pathogen. The system comprises a plurality of electronic devices comprising instructions to generate an ID and, when in proximity of another such electronic device, one or both electronic devices transmit/receive the ID to/from the other electronic device. Then, a score is generated based on a plurality of such received IDs. Additionally, based on information received from a server, relevant treatment instructions are displayed to the subjects based on the received information and the score. The server comprises instructions for sending to the plurality of electronic devices the information to be displayed with the relevant treatment instructions, additionally the server and/or the electronic devices comprise instructions to generate a prediction of likelihood of a subject transmitting said pathogen, based on the score of the subject.

29 Claims, 12 Drawing Sheets

(51) Int. Cl.
  *H04W 4/02* (2018.01)
  *G16H 50/30* (2018.01)
  *G06N 7/00* (2006.01)
  *H04W 4/029* (2018.01)
(58) Field of Classification Search
  CPC ..... H04W 4/029; H04W 4/80; H04W 12/069;
    G08B 21/02; G07C 9/28; G07C 9/22;
    G06F 1/163; G06F 3/14; H04L 9/30;
    G09G 5/36; G09G 5/02; G09G 2354/00;
    G06K 7/10366
  USPC ............ 340/539.13, 539.12, 539.23, 539.11;
    705/2
  See application file for complete search history.

(56) References Cited

U.S. PATENT DOCUMENTS

| | | | |
|---|---|---|---|
| 8,862,448 | B2 | 10/2014 | Holmes et al. |
| 9,075,909 | B2 | 7/2015 | Almogy et al. |
| 10,275,526 | B2 | 4/2019 | Dodge et al. |
| 11,107,588 | B2* | 8/2021 | Ehrlich ................. G16H 50/80 |
| 11,170,898 | B2* | 11/2021 | Neumann .............. G16H 50/20 |
| 2004/0236604 | A1 | 11/2004 | McNair |
| 2006/0036619 | A1 | 2/2006 | Fuerst et al. |
| 2006/0218010 | A1 | 9/2006 | Michon et al. |
| 2008/0091471 | A1 | 4/2008 | Michon et al. |
| 2009/0319295 | A1 | 12/2009 | Kass-Hout et al. |
| 2011/0238432 | A1 | 9/2011 | DeLoach |
| 2012/0274464 | A1 | 11/2012 | Sweeney et al. |
| 2015/0350850 | A1 | 12/2015 | Edge |
| 2017/0019765 | A1 | 1/2017 | Hoyer et al. |
| 2017/0352119 | A1 | 12/2017 | Pittman |
| 2020/0105422 | A1* | 4/2020 | Ribble ................. A61B 5/0205 |
| 2020/0242566 | A1* | 7/2020 | Agarwal ............... G16H 40/20 |
| 2020/0279464 | A1 | 9/2020 | Llewelyn et al. |
| 2020/0357510 | A1 | 11/2020 | Bhavani et al. |
| 2020/0388382 | A1 | 12/2020 | Costantino et al. |
| 2021/0020294 | A1 | 1/2021 | Bharmi et al. |
| 2021/0082583 | A1 | 3/2021 | Ehrlich et al. |

OTHER PUBLICATIONS

Notice of Allowance & Interview Summary dated May 25, 2021 From the US Patent and Trademark Office Re. U.S. Appl. No. 17/106,279. (13 Pages).
Office Action and Search Report dated Dec. 17, 2020 From the Israel Patent Office Re. Application No. 276648. (9 Pages).
Office Action and Search Report dated Dec. 17, 2020 From the Israel Patent Office Re. Application No. 276665. (9 Pages).
Office Action and Search Report dated Dec. 17, 2020 From the Israel Patent Office Re. Application No. 277083. (10 Pages).
Official Action dated Feb. 3, 2021 From the US Patent and Trademark Office Re. U.S. Appl. No. 17/106,279. (22 Pages).
Translation Dated Jan. 3, 2021 of Office Action dated Dec. 17, 2020 From the Israel Patent Office Re. Application No. 276665. (5 Pages).
Translation Dated Jan. 3, 2021 of Office Action dated Dec. 17, 2020 From the Israel Patent Office Re. Application No. 277083. (5 Pages).
Translation Dated Jan. 3, 2021 of Office Action Report dated Dec. 17, 2020 From the Israel Patent Office Re. Application No. 276648. (5 Pages).
Abbasi et al. "Modeling Vaccine Allocations in the COVID-19 Pandemic: A Case Study in Australia", Available at SSRN, P,1-34, Dec. 9, 2020.
ACS "2011-2015 5-Year ACS Commuting Flows: Tables", ACS, 1 P., Last Revised Oct. 24, 2019.
Ahmed et al. "A Survey of COVID-19 Contact Tracing Apps", IEEEAccess, 8: 134577-134601, Published Online Jul. 20, 2020.
Ahmed et al. "Coronavirus Disease 2019 (COVID-19) Complicated by Acute Respiratory Distress Syndrome: An Internist's Perspective", Cureus, 12(3): e7482-1-e7482-7, Published Online Mar. 31, 2020.
Anderson et al. "Challenges in Creating Herd Immunity to SARS-CoV-2 Infection by Mass Vaccination", The Lancet, 396(10263): 1616-1618, Published Online Nov. 4, 2020.
Anglemyer et al. "Digital Contact Tracing Technologies in Epidemics: A Rapid Review" , Cochrane Database of Systematic Reviews, 2020(8/Art.No.CD013699): 1-45, Aug. 18, 2020.
Aspnes et al. "Inoculation Strategies for Victims of Viruses and the Sum-of-Squares Partition Problem", Journal of Computer and System Sciences, 72(6): 1077-1093, Available Online Apr. 17, 2006.
Barabasi et al. "Emergence of Scaling in Random Networks", Science, 286(5439): 509-513, Oct. 15, 1999.
Barrett et al. "Generation and Analysis of Large Synthetic Social Contact Networks", Proceedings of the 2009 Winter Simulation Conference, WSC, Austin TX, USA, Dec. 13-16, 2009, p. 1-12, Dec. 13, 2009.
Beckman et al. "Creating Synthetic Baseline Populations", Transportation Research Part A: Policy and Practice, 30(6): 415-429, Nov. 1996.
Ben Tovim "The Ministry of Health Stops the Development of the 'Shields': It Prefers to Force You to Install A New Application", Geek Time, p. 1-9, Dec. 1, 2020.
Bertsimas et al. "Optimizing Vaccine Allocation to Combat the COVID-19 Pandemic", MedRxiv Preprint, p. 1-27, Posted Nov. 18, 2020.
Bollobas et al. "Robustness and Vulnerability of Scale-Free Random Graphs", Internet Mathematics, 1(1): 1-35, Jan. 2004.
Britton et al. "A Mathematical Model Reveals the Influence of Population Heterogeneity on Herd Immunity to SARS-CoV-2", Science, 369(6505): 846-849, Aug. 14, 2020.
Bubar et al. "Model-Informed COVID-19 Vaccine Prioritization Strategies by Age and Serostatus", Science, 371(6532): 916-921, Feb. 26, 2021.
Buckner et al. "Optimal Dynamic Priorization of Scarce COVID-19 Vaccines", MedRxiv Preprint, p. 1-37, Sep. 22, 2020.
Cattuto et al. "Dynamics of Person-to-Person Interactions From Distributed RFID Sensor Networks", PLoS ONE, 5(&): e11596-1-e11596-9, Jul. 15, 2010.
CDC "COVID-19 Pandemic Planning Scenarios", Centers for Disease Control and Prevention, CDC, Office of the Assistant Secretary for Preparedness and Response, ASPR, p. 1-9, Updated Sep. 10, 2020.
CDC "COVID-19 Pandemic Planning Scenarios", Centers for Disease Control and Prevention, CDC, p. 1-9, Updated Mar. 19, 2021.
Centre for Time Use Research "Multinational Time Use Study", Centre for Time Use Research, p. 1-3, 2021.
Chan et al. "PACT: Privacy-Sensitive Protocols and Mechanisms for Mobile Contact Tracing", ArXiv Preprint ArXiv:2004.03544v4, p. 1-22, May 7, 2020.
Chen et al. "Medical Costs of Keeping the US Economy Open During COVID-19", Scientific Reports, 10(1): 18422-1-18422-10, Oct. 28, 2020.
Chen et al. "Next Generation Technology for Epidemic Prevention and Control: Data-Driven Contact Tracing", IEEE Access, 7: 2633-2642, Dec. 24, 2018.
Cohen et al. "Efficient Immunization Strategies for Computer Networks and Populations", ArXiv Preprint ArXiv:Cond-Mat/0207387v3, p. 1-5, Dec. 10, 2003.
Cox "The Vulnerable Can Wait. Vaccinate the Super-Spreaders First. Who Gets Priority When Covid-19 Shots Are in Short Supply? Network Theorists Have A Counterintuitive Answer: Start With the Sociel Butterflies". Wired, Avid Reader Press, p. 1-20, Dec. 2020-Jan. 2021.
Deming et al. "On A Least Squares Adjustment of A Sampled Frequency Table When the Expected Marginal Totals Are Known", The Annals of Mathematical Statistics, 11(4): 427-444, Dec. 1940.
Draief et al. "Thresholds for Virus Spread on Networks", The Annals of Applied Probability, 18(2): 359-378. Apr. 2008.
Eames et al. "Epidemic Prediction and Control in Weighted Networks", Epidemics, 1(1): 70-76. Published Online Dec. 25, 2008.

(56) References Cited

OTHER PUBLICATIONS

Eubank et al. "Modelling Disease Outbreaks in Realistic Urban Social Networks", Nature, 429(6988): 180-184, May 13, 2004.

Eubank et al. "Structure of Social Contact Networks and Their Impact on Epidemics", Discrete Methods in Epidemiology, DIMACS Series Diescrete Mathematics and Theoretical Computer Science, American Mathematic Society, 70: 181-1-181-32, 2021.

Ferretti et al. "Quantifying SARS-CoV-2 Transmission Suggests Epidemic Control With Digital Contact Tracing", Science, 368(6491): eabb6936-1-eabb6936-7, Published Online Mar. 31, 2020.

FHWA "National Household Travel Survey", U.S. Department of Transportation, Federal Highway Administration, FHWA, 2 P., Mar. 29, 2021.

Foy et al. "Comparing COVID-19 Vaccine Allocation Strategies in India: A Mathematical Modelling Study", International Journal of Infectious Diseases, 103: 431-438. Published Online Dec. 31, 2020.

Ganesh et al. "The Effect of Network Topology on the Spread of Epidemics", Proceedings IEEE 24th Annual Joint Conference of the IEEE Computer and Communications Societies. Miami, FL, USA. Mar. 13-17, 2005, p. 1-12, Mar. 13, 2005.

Gayle et al. "Framework for Equitable Allocation of COVID-19 Vaccine", Committee of Equitable Allocation of Vaccine for the Novel Coronavirus, Board on Health Sciences Policy, Board on Population Health and Public Health Practice, Health and Medicine Division, A Consensus Study Report of The National Academies of Sciences—Engineering—Medicine, National Academy of Medicine, P.i-xx, 1-252, 2020.

Genois et al. "Can Co-Location Be Used as A Proxy for Face-to-Face Contacts?", EPJ Data Science, 7(1): 11-1-11-18, Dec. 2018.

Germann et al. "Mitigation Strategies for Pandemic Influenza in the United States", Proc. Natl. Acad. Sci. USA, PNAS, 103(15): 5935-5940, Apr. 11, 2006.

Gillespie "A General Method for Numerically Simulating the Stochastic Time Evolution of Coupled Chemical Reactions", Journal of Computational Physics, 22(4): 403-434, Dec. 1976.

GitHub Microsoft "Computer Generated Building Footprints for the Untied States", GitHub—Microsoft / USBuilding Footprints, Version v2.0, p. 1-9, Jul. 13, 2018.

GitHub Nytimes "An Ongoing Repository of Data on Coronavirus Cases and Deaths in the U.S.", GutHub Nytimes / Covid-19 Data, The New York Times, p. 1-12, 2021.

Halloran et al. "Modeling Targeted Layered Containment of An Influenza Pandemic in the United States", Proc. Natl. Acad. Sci. USA, PNAS, 105(12): 4639-4644, Mar. 25, 2008.

Hayrapetyan et al. "Unbalanced Graph Cuts", ESA'05, Proceedings of the 13th Annual European Conference on Algorithms, LNCS, 3669: 191-202, Oct. 3, 2005.

Hogan et al. "Report 33: Modelling the Allocation and Impact of A COVID-19 Vaccine", Imperial College London. p. 1-21, Sep. 25, 2020.

IBM Research Editorial Staff "Tracking Tuberculosis in South Africa", IBM Research Blog, 7 P., Oct. 11, 2016.

Jenvald et al. "Simulation as Decision Support in Pandemic Influenza Preparedness and Response", Proceedings of The Conference on Intelligent Human Computer Systems for Crisis Response and Management 2007. ISCRAM 2007, p. 295-304, May 13, 2007.

Kretschmar et al. "Impact of Delays on Effectiveness of Contact Tracing Strategies for COVID-19: A Modelling Study", Lancet Public Health, 5(8): e452-e459, Published Online Jul. 16, 2020.

Kumar et al. "Existence Theorems and Approximation Algorithms for Generalized Network Security Games", 2010 IEEE 30th International Conference on Distributed Computing Systems, Genoa, Italy, Jun. 21-25, 2010, p. 1-19, Jun. 21, 2010.

Lipsitch et al. "Understanding COVID-19 Vaccine Efficacy: Vaccine Efficacy in High-Risk Groups and reduced Viral Shedding Are Important for Protection". Science, 370(6518): 763-766, Nov. 13, 2020.

Lofgren et al. "Opinion: Mathematical Models: A Key Tool for Outbreak Response", Proc. Natl. Acad. Sci. USA, PNAS, 111(51): 18095-18096, Dec. 23, 2014. & Correction, 112(2): E234, Jan. 13, 2015.

Longini Jr. et al. "Containing Pandemic Influenza With Antiviral Agents", American Journal of Epidemiology, 159(7): 623-633, Apr. 1, 2004.

Lum et al. "A Two-Stage, Fitted Values Approach to Activity Matching", International Journal of Transportation, 4(1): 41-56, 2016.

Machi et al. "Scalable Epidemiological Workflows to Support COVID-19 Planning and Response", MedRxiv Preprint, p. 1-19, Posted Online Feb. 26, 2021.

Matrajt et al. "Vaccine Optimization for COVID-19: Who to Vaccinate First?", MedRxiv Preprint, p. 1-84, Posted Nov. 10, 2020.

May et al. "Spatial Heterogeneity and the Design of Immunization Programs", Mathematical Biosciences, 72(1): 83-111, Nov. 1984.

Medlock "Optimizing Influenza Vaccine Distribution", Clemson University, Department of Mathematical Sciences, p. 1-29, Aug. 3, 2009.

Morawska et al. "Airborne Transmission of SARS-CoV-2: The World Should Face the Reality", Environmental International, 139: 105730-1-105730-4, Available Online Apr. 10, 2020.

Pastor-Satorras et al. "Epidemic Processes in Complex Networks", ARXiv Preprint ArXiv: 1408.2701v2, p. 1-62, Sep. 18, 2015.

Pastor-Satorras et al. "Immunization of Complex Networks", ArXiv Preprint ArXiv:Cond-Math/010766v2, p. 1-9, Apr. 11, 2002.

Preciado et al. "Optimal Resource Allocation for Networks Protection Against Spreading Processes", ArXiv Preprint ArXiv: 1309.6270v2, p. 1-10, May 11, 2014.

Preciado et al. "Optimal Vaccine Allocation to Control Epidemic Outbreaks in Arbitrary Networks", ArXiv Preprint ArXiv:1303.3984v1, p. 1-8, Mar. 16, 2013.

Qian et al. "Ventilation Control for Airborne Transmission of Human Exhaled BioAerosols in Buildings", Journal of Thoracic Disease, 10(Suppl.19): S2295-S2304, Jul. 2018.

Saad-Roy et al. "Immune Life History, Vaccination, and the Dynamics of SARS-CoV-2 Over the Next 5 Years", Science, 370(6518): 811-818, Nov. 13, 2020.

Saha et al. "Approximation Algorithms for Reducing the Spectral Radius to Control Epidemic Spread", ArXiv Preprint ArXiv: 1501.0661v1, p. 1-14, Jan. 26, 2015.

Sambaturu et al. "Designing Effective and Practical Interventions to Contain Epidemics", Proceedings of the 19th International Conference on Autonomous Agents and MultiAgent Systems, AAMAS 2020, Auckland, New Zealand, May 9-13, 2020, p. 1187-1195, May 9, 2020.

Skene et al. "A Marginal Benefit Approach for Vaccinating Influenza 'Superspreaders'", Medical Decision Making, 34(4): 536-549, May 2014.

Straetemans et al. "Priorization Strategies for Pandemic Influenza Vaccine in 27 Countries of the European Union and the Global Health Security Action Group: A Review", BMC Public Health, 7(1): 236-1-236-12, Published Online Sep. 7, 2007.

Tennenholtz et al. "Sequential Vaccination for Containing Epidemics", MedRxiv Preprint, p. 1-16, Posted Apr. 14, 2020.

Tong et al. "Gelling, and Melting, Large Graphs by Edge Manipulation". Proceedings of the 21st ACM International Conference on Information and Knowledge Management, CIKM'12, Maui, HI, USA, Oct. 29-Nov. 2, 2012, p. 245-254, Oct. 29, 2012.

U.S Bureau of Labor Statistics "American Time Use Survey (ATUS)", U.S Bureau of Labor Statstics, p. 1 -4, Jun. 25, 2020.

U.S. Census Bureau "American Community Survey 2013-2017 5-Year Data Release: Median Household Income, Poverty Rates and Computer and Internet Use", U.S Census Bureau, Press Release, 7 P., Dec. 6, 2018.

Van Mieghem et al. "Virus Spread in Networks", IEEE/ACM Transactions on Networking, 17(1): 1-14, Published Online Jun. 24, 2008.

Van Mieghem et al. "Decreasing the Spectral Radius of A Graph by Link Removals", Physical Review E, 84(1): 016101-1-016101-12, Jul. 6, 2011.

(56) References Cited

OTHER PUBLICATIONS

Venkatramanan et al. "Optimizing Spatial Allocation of Seasonal Influenxa Vaccine Under Temporal Constraints", PLoS ONE, Computational Biology, 15(9): e1007111-1-e1007111-17, Sep. 16, 2019.
Venkatramanan et al. "Optimizing Spatial Allocation of Seasonal Influenza Vaccine Linder Temporal Constraints", PLoS Computational Biology, 15(9): e1007111-1-e1007111-17, Published Online Sep. 16, 2019.
Venkatramanan et al. "Spatio-Temporal Optimization of Seasonal Vaccination Using A Metapopulation Model of Influenza", 2017 IEEE INternational Conference on Healthcare Informatics, ICHI, Park City, UT, USA, Aug. 23-26, 2017, p. 134-144, Aug. 23, 2017.
Versel "Smartphone App Seeks 'Superspreaders' of Flu", MobileHealthNews, 3 P., Apr. 26, 2011.
Who "Draft Landscape of COVID-19 Candidate Vaccines", 9 P., Aug. 10, 2020.
Wilder et al. "Preventing Infectious Disease in Dynamic Populations Under Uncertainty", The Thirty-Second AAAI Conference on Artificial Intelligence, Computational Sustainability and Artificial Intelligence, AAAI-18, 32(1): 841-848, Apr. 25, 2018.
Yang et al. "Efficient Vaccination Strategies for Epidemic Control Using Network Information", Epidemics, 27: 115-122, Published Online Mar. 6, 2019.
Zhang et al. "Near-Optimal Algorithms for Controlling Propagation at Group Scale on Networks", IEEE Transactions on Knowledge and Data Engineering, 28(12): 3339-3352, Published Online Sep. 1, 2016.
Marathe et al. "Computational Epidemiology", KDD '14, Proceedings of the 20th ACM SIGKDD International Conference on Knowledge Discovery and Data Mining. New York City, NY, USA, Aug. 24-27, 2014, Slide Show. p. 1-209. Aug. 24, 2014. (Part 1 of 2).
Marathe et al. "Computational Epidemiology", KDD '14, Proceedings of the 20th ACM SIGKDD International Conference on Knowledge Discovery and Data Mining. New York City, NY, USA, Aug. 24-27, 2014, Slide Show, p. 1-209, Aug. 24, 2014. (Part 2 of 2).
Peters "RECEIPTS: DoD Joint Artificial Intelligence Center Monitoring Vaxx Deaths", Stew Peters Show, Rumble Video, Oct. 8, 2021.
Wilson "A Patent Issued for the Purpose of Contact Tracing All Vaccinated Humans Worldwide—Wake Up Stupid Little Sheep. You Are Being Led to Your Slaughter", The Exposé, 28 P., Oct. 16, 2021.
International Search Report and the Written Opinion dated Nov. 12, 2021 From the International Searching Authority Re. Application No. PCT/IL2021/050903 (12 Pages).
Whaiduzzaman et al. "A Privacy-Preserving Mobile and Fog Computing Framework to Trace and Prevent COVID-19 Community Transmission", IEEE Journal of Biomedical and Health Informatics. XP081708921, 24(12): 3564-3567, Sep. 23, 2020.
Yilmaz et al. "Kemeny-Based Testing for COVID-19", PLoS One, XP081712055,15(11): e0242401, 10 pages, Nov. 19, 2020.

\* cited by examiner

METHODS AND SYSTEMS OF PRIORITIZING TREATMENTS, VACCINATION, TESTING AND/OR ACTIVITIES WHILE PROTECTING THE PRIVACY OF INDIVIDUALS

RELATED APPLICATIONS

This application is a continuation of U.S. patent application Ser. No. 17/106,279 filed on Nov. 30, 2020, which claims the benefit of priority of Israel Patent Application No. 277083 filed on Sep. 1, 2020, Israel Patent Application No. 276665 filed on Aug. 11, 2020, and Israel Patent Application No. 276648 filed on Aug. 11, 2020. The contents of the above applications are all incorporated by reference as if fully set forth herein in their entirety.

This application is also related to United Arab Emirates Patent Application No. P6001304/2020 filed on Sep. 17, 2020, the contents of which are incorporated herein by reference in their entirety.

FIELD AND BACKGROUND OF THE INVENTION

The present invention, in some embodiments thereof, relates to methods and systems of prioritizing vaccinations\treatments\testing and, more particularly, but not exclusively, to method and systems of prioritizing vaccinations\treatments\testing in a pandemic situation, whereby vaccines are at short supply and while protecting the privacy of the individuals in the population.

Coronavirus disease 2019 (COVID-19) is an infectious disease caused by severe acute respiratory syndrome coronavirus 2 (SARS-CoV-2). It was first identified in December 2019 in Wuhan, Hubei, China, and has resulted in an ongoing pandemic. The first confirmed case has been traced back to 17 Nov. 2019 in Hubei. As of 6 Aug. 2020, more than 18.7 million cases have been reported across 188 countries and territories, resulting in more than 706,000 deaths. More than 11.3 million people have recovered. The virus is primarily spread between people during close contact, most often via small droplets produced by coughing, sneezing, and talking. The droplets usually fall to the ground or onto surfaces rather than travelling through air over long distances. However, the transmission may also occur through smaller droplets that are able to stay suspended in the air for longer periods of time in enclosed spaces, as typical for airborne diseases. Less commonly, people may become infected by touching a contaminated surface and then touching their face. It is most contagious during the first three days after the onset of symptoms, although spread is possible before symptoms appear, after they disappear and from people who show very mild or do not show symptoms at all.

In addition, about 5% of COVID-19 patients experience complications including septic shock, acute respiratory distress syndrome (ARDS), acute cardiac or kidney injury, and disseminated intravascular coagulation (DIC). These complications are thought to be manifestations of the cytokine storm triggered by the host immune response of the virus. In critically ill patients, ARDS was the most common complication in 67% of the patients with a 28-day mortality of 61.5%. DIC has been widely reported in COVID-19. Pulmonary embolism (PE) in COVID-19 patients has been reported in a few studies. A recent study pointed to a higher incidence of PE with 23% in severe COVID-19 patients. The relationship between virally triggered inflammation, venous thromboembolism, and ARDS in COVID-19 is still under investigation. Given that patients with severe COVID-19 often present with shortness of breath and pulmonary infiltrates, the diagnosis of PE may be overlooked in the context of an ARDS diagnosis.

A research article by Straetemans et. al. called "*Prioritization strategies for pandemic influenza vaccine in 27 countries of the European Union and the Global Health Security Action Group: a review*" discussed vaccine prioritization strategies during pandemic times, but its conclusions are limited to the critical groups, for example, health care providers (e.g., doctors, nurses, laboratories, hospitals, etc.), essential service providers (e.g., police, fire fighters, public sector personnel, governmental personnel, etc.) and high risk individuals (e.g., people with high risk of complications, pregnant women, children, etc.). These obvious groups usually amount to less than 2-10% of the total population, which still leaves the government with the question of what is the best order to vaccinate the rest of the population, namely prioritizing vaccinations.

SUMMARY OF THE INVENTION

Following is a non-exclusive list including some examples of embodiments of the invention. The invention also includes embodiments, which include fewer than all the features in an example, and embodiments using features from multiple examples, also if not expressly listed below.

Example 1. An anonymized method of treating subjects against an infectious disease caused by a pathogen, comprising:

a. providing an electronic device with proximity tracking circuitry for each of said subjects;

b. generating an ID for each said electronic device;

c. at a proximity event, when a particular said electronic device of a particular said subject is in proximity of one or more other of said electronic devices, one or both of transmitting said ID or an indication thereof to said one or more other devices and receiving an ID or indication thereof from said one or more other devices, by said particular electronic device;

d. generating, by said particular electronic device a score reflecting a propensity for proximity, according to a plurality of received IDs;

e. generating for said particular electronic device a prioritization of treatment based on said score;

f. treating said particular subject according to said prioritization.

Example 2. The method according to example 1, wherein said generating an ID comprises generating an ID having fewer than 100,000 potential values.

Example 3. The method according to example 2, wherein said generating an ID comprises generating a unique ID and also generating said ID as a portion of said unique ID.

Example 4. The method according to example 1, further comprising changing said ID periodically.

Example 5. The method according to example 1, further comprising generating a second ID and transmitting said second ID or indication thereof together with said ID.

Example 6. The method according to example 5, wherein said transmitting a second ID is carried out only at a fraction of said proximity events.

Example 7. The method according to example 6, wherein said transmitting comprises transmitting also second IDs previously received from others of said electronic devices.

Example 8. The method according to example 6, comprising generating an indication of closeness of a population met by said electronic device based on said received second IDs.

Example 9. The method according to example 1, wherein said score depends on an estimation of propensity of proximity of said one or more other devices.

Example 10. The method according to example 1, wherein said generating said score comprises counting the number of received IDs.

Example 11. The method according to example 10, wherein said counting comprises counting unique IDs.

Example 12. The method according to example 10, wherein said counting comprises counting IDs with a weighted parameter, said weighted parameter is generated by analyzing said exchanged second IDs.

Example 13. The method according to example 1, wherein said generating for said particular device comprises transmitting said score to a server and generating said prioritization on said server.

Example 14. The method according to example 13, wherein generating said prioritization comprises comparing scores by different ones of said electronic devices.

Example 15. The method according to example 1, wherein said generating for said particular device comprises generating said prioritization on said particular electronic device.

Example 16. The method according to example 15, wherein said generation comprises receiving form a server a list or a function indication prioritization according to score.

Example 17. The method according to example 1, comprising displaying treatment instructions on said particular electronic device based on said generated prioritization.

Example 18. The method of example 1, wherein said pathogen comprises a corona virus and wherein said treatment comprises a vaccination and wherein said prioritization is used to select subjects at greater risk of transmitting the pathogen during a pandemic to be vaccinated sooner than subjects less likely to transmit the pathogen.

Example 19. A system for anonymously selecting subjects for treatment against an infectious disease caused by a pathogen, comprising:
a. a plurality of electronic devices configured to be carried around by said subjects and configured with instructions to:
  i. generate an ID comprising for each said electronic device;
  ii. when in proximity of another such electronic device, one or both of transmit said ID or an indication thereof to said another electronic device and receive an ID or indication thereof from said another electronic device;
  iii. generating, a score based on a plurality of such received IDs;
  iv. receiving information from a server;
  v. displaying relevant treatment instructions to said subjects based on said received information;
b. at least one server comprising a memory and a plurality of modules; said memory-comprising instructions for:
  vi. sending to said plurality of electronic devices information usable by a circuitry in said plurality of electronic devices to display said relevant treatment instructions,
wherein said at least one server or said electronic devices comprise instructions to generate a prediction of likelihood of a subject transmitting said pathogen, based on a score of the subject.

Example 20. The system according to example 19, wherein said information comprises one or more of subject specific information.

Example 21. The system according to example 19, wherein said information comprises general information usable by a plurality of subjects and devices thereof.

Example 22. The system according to example 19, wherein said server is configured with instructions to receive anonymous scores for a plurality of said electronic devices and use said received scores to generate said general information, said electronic devices configured to use said general information to determine a relative treatment priority for their respective subjects.

Example 23. The system according to example 19, wherein said electronic devices comprises a proximity-detecting module using one or more of:
a. physical proximity data received by means of electronic positioning data of said subject;
b. a distance indicating sensor which indicates physical proximity of the location of a device in relation to the location of said another device; and
c. historical location data.

Example 24. The system according to example 19, wherein said at least one server or said electronic devices comprise instructions to determine a treatment prioritization based on said likelihood.

Example 25. The system according to example 23, wherein said determine a treatment prioritization further comprises one or more of:
a. generating a score component based on a nature of a location where said physical proximity data is related;
b. generating a score component comprising health data of the subject of one or both electronic devices;
c. generating a score component comprising a profession of the subject of one or both electronic devices;
d. generating a score component reflecting relative health risk to said subject if said subject contracts said pathogen; and
e. generating a score component reflecting damage to society if said subject contracts said pathogen.

Example 26. The system according to example 23, wherein when said physical proximity data is related to a location that is either indoors or in a closed space, then said predicted likelihood of said subject of transmitting said pathogen increases by a factor of between about 10 times to about 100 times.

Example 27. The system according to example 19, further comprising a vaccination server, which allocates vaccinations for a corona virus according to, said displayed treatment information.

Example 28. The system according to example 27, wherein said server comprises a simulation module configured to perform one or both of:
(a) predict the effect of vaccination on disease spread;
(b) predict the effect of an ID transmission probability on distinguishing between subjects who contact mainly subjects in a same subpopulation.

Example 29. The system of example 19, wherein said electronic devices are configured to transmit a second ID and previously received second IDs, at a probability of less than 10% and using said received second IDs to generate said score. Example 30. The system of example 19, wherein said transmitted ID is a non-unique ID having fewer possible values than 10% of the number of said devices.

According to an aspect of some embodiments of the present invention there is provided a method of selecting subjects for being vaccinated/treated against an infectious disease caused by a pathogen, using personal physical proximity information of a subject, comprising:

a. generating, by circuitry, a predicted likelihood of said subject of transmitting said pathogen based on said physical proximity information, for a plurality of subjects;

b. selecting subjects of said plurality of subjects for vaccinating/treating based on a prediction that said vaccinating/treating said subjects will reduce a likelihood of spreading of said disease in said plurality of subjects, wherein said selecting is based on said generated predicted likelihood.

According to some embodiments of the invention, said pathogen is selected from the group consisting of a virus, a bacterium, a fungus and a protozoan.

According to some embodiments of the invention, said disease is endemic or pandemic.

According to some embodiments of the invention, said predicted likelihood of said subject of transmitting said pathogen comprises one or more score components used for generating a score.

According to some embodiments of the invention, said score relates to a predicted likelihood of a group of subjects transmitting said pathogen based on said physical proximity information, and said physical proximity information is a first score component used for said generating said score.

According to some embodiments of the invention, said generating said score further comprises a score component based on a nature of a location where said physical proximity information is related.

According to some embodiments of the invention, said nature of the location is one or more of an open space, a closed space, indoor, outdoor, ventilated indoor space, non-ventilated indoor space and any combination thereof.

According to some embodiments of the invention, when said physical proximity information is related to a location that is either indoors or in a closed space, then said predicted likelihood of said subject of transmitting said pathogen increases by a factor of between about 10 times to about 100 times.

According to some embodiments of the invention, said physical proximity information is physical proximity data received by means of electronic positioning data of said subject.

According to some embodiments of the invention, said physical proximity information is physical proximity data of the location of said subject in relation to the location of other subjects.

According to some embodiments of the invention, said physical proximity data comprises one or more of physical proximity distance data, duration of physical proximity data and/or ambience of physical proximity data.

According to some embodiments of the invention, said electronic positioning data is one or more of electronic geographical positioning data of said subject, electronic proximity positioning data of said subject relative to other subjects.

According to some embodiments of the invention, said method further comprises generating a predicted likelihood of said subject contracting said pathogen based on said physical proximity data.

According to some embodiments of the invention, said generating a score further comprises a second score component based on said predicted likelihood of said subject contracting said pathogen based on said physical proximity data.

According to some embodiments of the invention, said electronic positioning data is collected using one or more electronic devices.

According to some embodiments of the invention, said one or more electronic devices are one or more of a smartphone, a tablet, a smartwatch and a dedicated electronic device.

According to some embodiments of the invention, the method further comprising vaccinating/treating said subjects according to said score.

According to some embodiments of the invention, said generating a score further comprises a third score component reflecting relative health risk to said subject if said subject contracts said pathogen.

According to some embodiments of the invention, said generating a score further comprises a fourth score component reflecting damage to society if said subject contracts said pathogen.

According to some embodiments of the invention, said electronic positioning data comprises geographical location data.

According to some embodiments of the invention, said physical proximity information comprises historical location data.

According to some embodiments of the invention, said generating said score further comprises a component comprising historical health data.

According to some embodiments of the invention, said generating said score further comprises a component comprising a profession in record of said subject.

According to some embodiments of the invention, said physical proximity information further comprises information received from a third party.

According to some embodiments of the invention, said physical proximity information is provided by said subject actively.

According to some embodiments of the invention, said physical proximity information is provided by said subject passively by means of said one or more electronic devices.

According to some embodiments of the invention, said pathogen is a virus.

According to some embodiments of the invention, said virus is a corona virus.

According to some embodiments of the invention, said virus is SARS-CoV.

According to some embodiments of the invention, said virus is MERS-CoV.

According to some embodiments of the invention, said virus is SARS-CoV-2.

According to some embodiments of the invention, said virus is an influenza virus.

According to some embodiments of the invention, said disease results in influenza like symptoms.

According to an aspect of some embodiments of the present invention there is provided a method of selecting subjects for being vaccinated/treated against an infectious disease caused by a pathogen, comprising:

a. automatically collecting physical proximity information of a subject with other subjects;

b. generating a predicted likelihood of said subject of transmitting said virus based on said physical proximity information;

c. generating a score comprising a first score component based on said predicted likelihood of said subject of transmitting said virus;

d. repeating steps b-c for a plurality of subjects; and e. prioritizing vaccination/treatment of said subjects according to said score.

According to some embodiments of the invention, said pathogen is selected from the group consisting of a virus, a bacterium, a fungus and a protozoan.

According to some embodiments of the invention, said disease is endemic or pandemic.

According to some embodiments of the invention, said generating said score further comprises a score component based on a nature of a location where said physical proximity information is related.

According to some embodiments of the invention, said nature of the location is one or more of an open space, a closed space, indoor, outdoor, ventilated indoor space, non-ventilated indoor space and any combination thereof.

According to some embodiments of the invention, when said physical proximity information is related to a location that is either indoors or in a closed space, then said predicted likelihood of said subject of transmitting said pathogen increases by a factor of between about 10 times to about 100 times.

According to some embodiments of the invention, said physical proximity information is physical proximity data received by means of electronic positioning data of said subject.

According to some embodiments of the invention, said physical proximity information is physical proximity data of the location of said subject in relation to the location of other subjects.

According to some embodiments of the invention, said physical proximity data comprises one or more of physical proximity distance data, duration of physical proximity data and/or ambience of physical proximity data.

According to some embodiments of the invention, said electronic positioning data is one or more of electronic geographical positioning data of said subject, electronic proximity positioning data of said subject relative to other subjects.

According to some embodiments of the invention, said method further comprises generating a predicted likelihood of said subject contracting said pathogen based on said physical proximity data.

According to some embodiments of the invention, said generating a score further comprises a second score component based on said predicted likelihood of said subject contracting said pathogen based on said physical proximity data.

According to some embodiments of the invention, said electronic positioning data is collected using one or more electronic devices.

According to some embodiments of the invention, said one or more electronic devices are one or more of a smartphone, a tablet, a smartwatch and a dedicated electronic device.

According to some embodiments of the invention, the method further comprising vaccinating/treating said subjects according to said score.

According to some embodiments of the invention, said generating a score further comprises a third score component reflecting relative health risk to said subject if said subject contracts said pathogen.

According to some embodiments of the invention, said generating a score further comprises a fourth score component reflecting damage to society if said subject contracts said pathogen.

According to some embodiments of the invention, said electronic positioning data comprises geographical location data.

According to some embodiments of the invention, said physical proximity information comprises historical location data.

According to some embodiments of the invention, said generating said score further comprises a component comprising historical health data.

According to some embodiments of the invention, said generating said score further comprises a component comprising a profession in record of said subject.

According to some embodiments of the invention, said physical proximity information further comprises information received from a third party.

According to some embodiments of the invention, said physical proximity information is provided by said subject actively.

According to some embodiments of the invention, said physical proximity information is provided by said subject passively by means of said one or more electronic devices.

According to some embodiments of the invention, said pathogen is a virus.

According to some embodiments of the invention, said virus is a corona virus.

According to some embodiments of the invention, said virus is SARS-CoV.

According to some embodiments of the invention, said virus is MERS-CoV.

According to some embodiments of the invention, said virus is SARS-CoV-2.

According to some embodiments of the invention, said virus is an influenza virus.

According to some embodiments of the invention, said disease results in influenza like symptoms.

According to an aspect of some embodiments of the present invention there is provided a system for selecting subjects for being vaccinated/treated against an infectious disease caused by a pathogen, comprising:
 a. at least one server comprising a memory;
 b. an analytics module;
 c. a database module;
 d. a simulation module;
said memory in said at least one server comprising instructions, said instructions comprising:
 i. generating, by circuitry, a predicted likelihood of said subject of transmitting said pathogen based on said physical proximity information, for a plurality of subjects;
 ii. selecting subjects of said plurality of subjects for vaccinating/treating based on a prediction that said vaccinating/treating said subjects will reduce a likelihood of spreading of said disease in said plurality of subjects, wherein said selecting is based on said generated predicted likelihood.

According to some embodiments of the invention, said pathogen is selected from the group consisting of a virus, a bacterium, a fungus and a protozoan.

According to some embodiments of the invention, said disease is endemic or pandemic.

According to some embodiments of the invention, said predicted likelihood of said subject of transmitting said pathogen comprises one or more score components used for generating a score.

According to some embodiments of the invention, said score relates to a predicted likelihood of a group of subjects transmitting said pathogen based on said physical proximity information, and said physical proximity information is a first score component used for said generating said score.

According to some embodiments of the invention, said generating said score further comprises a score component based on a nature of a location where said physical proximity information is related.

According to some embodiments of the invention, said nature of the location is one or more of an open space, a closed space, indoor, outdoor, ventilated indoor space, non-ventilated indoor space and any combination thereof.

According to some embodiments of the invention, when said physical proximity information is related to a location that is either indoors or in a closed space, then said predicted likelihood of said subject of transmitting said pathogen increases by a factor of between about 10 times to about 100 times.

According to some embodiments of the invention, said physical proximity information is physical proximity data received by means of electronic positioning data of said subject.

According to some embodiments of the invention, said physical proximity information is physical proximity data of the location of said subject in relation to the location of other subjects.

According to some embodiments of the invention, said physical proximity data comprises one or more of physical proximity distance data, duration of physical proximity data and/or ambience of physical proximity data.

According to some embodiments of the invention, said electronic positioning data is one or more of electronic geographical positioning data of said subject, electronic proximity positioning data of said subject relative to other subjects.

According to some embodiments of the invention, said method further comprises generating a predicted likelihood of said subject contracting said pathogen based on said physical proximity data.

According to some embodiments of the invention, said generating a score further comprises a second score component based on said predicted likelihood of said subject contracting said pathogen based on said physical proximity data.

According to some embodiments of the invention, said electronic positioning data is collected using one or more electronic devices.

According to some embodiments of the invention, said one or more electronic devices are one or more of a smartphone, a tablet, a smartwatch and a dedicated electronic device.

According to some embodiments of the invention, the system further comprising vaccinating/treating said subjects according to said score.

According to some embodiments of the invention, said generating a score further comprises a third score component reflecting relative health risk to said subject if said subject contracts said pathogen.

According to some embodiments of the invention, said generating a score further comprises a fourth score component reflecting damage to society if said subject contracts said pathogen.

According to some embodiments of the invention, said electronic positioning data comprises geographical location data.

According to some embodiments of the invention, said physical proximity information comprises historical location data.

According to some embodiments of the invention, said generating said score further comprises a component comprising historical health data.

According to some embodiments of the invention, said generating said score further comprises a component comprising a profession in record of said subject.

According to some embodiments of the invention, said physical proximity information further comprises information received from a third party.

According to some embodiments of the invention, said physical proximity information is provided by said subject actively.

According to some embodiments of the invention, said physical proximity information is provided by said subject passively by means of said one or more electronic devices.

According to some embodiments of the invention, said simulation module further comprises a prediction module.

According to some embodiments of the invention, said pathogen is a virus.

According to some embodiments of the invention, said virus is a corona virus.

According to some embodiments of the invention, said virus is SARS-CoV.

According to some embodiments of the invention, said virus is MERS-CoV.

According to some embodiments of the invention, said virus is SARS-CoV-2.

According to some embodiments of the invention, said virus is an influenza virus.

According to some embodiments of the invention, said disease results in influenza like symptoms.

Following is a second non-exclusive list including some examples of embodiments of the invention. The invention also includes embodiments, which include fewer than all the features in an example, and embodiments using features from multiple examples, also if not expressly listed below.

Example 1. A method of selecting subjects for being vaccinated against an infectious disease caused by a pathogen, using personal physical proximity information of a subject, comprising:

a. generating, by circuitry, a predicted likelihood of said subject of transmitting said pathogen based on said physical proximity information, for a plurality of subjects;

b. selecting subjects of said plurality of subjects for vaccinating based on a prediction that said vaccinating said subjects will reduce a likelihood of spreading of said disease in said plurality of subjects, wherein said selecting is based on said generated predicted likelihood.

Example 2. The method according to example 1, wherein said pathogen is selected from the group consisting of a virus, a bacterium, a fungus and a protozoan.

Example 3. The method according to according to any one of examples 1-2, wherein said disease is endemic or pandemic.

Example 4. The method according to any one of examples 1-3, wherein said predicted likelihood of said subject of transmitting said pathogen comprises one or more score components used for generating a score.

Example 5. The method according to example 4, wherein said score relates to a predicted likelihood of a group of subjects transmitting said pathogen based on said physical proximity information, and said physical proximity information is a first score component used for said generating said score.

Example 6. The method according to any one of examples 4-5, wherein said generating said score further comprises a score component based on a nature of a location where said physical proximity information is related.

Example 7. The method of example 6, wherein said nature of the location is one or more of an open space, a closed space, indoor, outdoor, ventilated indoor space, non-ventilated indoor space and any combination thereof.

Example 8. The method according to any one of examples 1-7, wherein when said physical proximity information is related to a location that is either indoors or in a closed space, then said predicted likelihood of said subject of transmitting said pathogen increases by a factor of between about 10 times to about 100 times.

Example 9. The method according to any one of examples 1-8, wherein said physical proximity information is physical proximity data received by means of electronic positioning data of said subject.

Example 10. The method according to any one of examples 1-9, wherein said physical proximity information is physical proximity data of the location of said subject in relation to the location of other subjects.

Example 11. The method according to any one of examples 9-10, wherein said physical proximity data comprises one or more of physical proximity distance data, duration of physical proximity data and/or ambience of physical proximity data.

Example 12. The method according to any one of examples 9-11, wherein said electronic positioning data is one or more of electronic geographical positioning data of said subject, electronic proximity positioning data of said subject relative to other subjects.

Example 13. The method according to any one of examples 1-12, wherein said method further comprises generating a predicted likelihood of said subject contracting said pathogen based on said physical proximity data.

Example 14. The method according to any one of examples 4-13, wherein said generating a score further comprises a second score component based on said predicted likelihood of said subject contracting said pathogen based on said physical proximity data.

Example 15. The method according to any one of examples 9-14, wherein said electronic positioning data is collected using one or more electronic devices.

Example 16. The method of example 15, wherein said one or more electronic devices are one or more of a smartphone, a tablet, a smartwatch and a dedicated electronic device.

Example 17. The method according to any one of examples 4-16, further comprising vaccinating said subjects according to said score.

Example 18. The method according to any one of examples 4-17, wherein said generating a score further comprises a third score component reflecting relative health risk to said subject if said subject contracts said pathogen.

Example 19. The method according to any one of examples 4-18, wherein said generating a score further comprises a fourth score component reflecting damage to society if said subject contracts said pathogen.

Example 20. The method according to any one of examples 9-19, wherein said electronic positioning data comprises geographical location data.

Example 21. The method according to any one of examples 1-20, wherein said physical proximity information comprises historical location data.

Example 22. The method according to any one of examples 4-21, wherein said generating said score further comprises a component comprising historical health data.

Example 23. The method according to any one of examples 4-22, wherein said generating said score further comprises a component comprising a profession in record of said subject.

Example 24. The method according to any one of examples 1-23, wherein said physical proximity information further comprises information received from a third party.

Example 25. The method according to any one of examples 1-24, wherein said physical proximity information is provided by said subject actively.

Example 26. The method according to any one of examples 1-25, wherein said physical proximity information is provided by said subject passively by means of said one or more electronic devices.

Example 27. The method according to any one of examples 1-26, wherein said pathogen is a virus.

Example 28. The method according to any one of examples 1-27, wherein said virus is a corona virus.

Example 29. The method according to any one of examples 1-28, wherein said virus is SARS-CoV.

Example 30. The method according to any one of examples 1-28, wherein said virus is MERS-CoV.

Example 31. The method according to any one of examples 1-28, wherein said virus is SARS-CoV-2.

Example 32. The method according to any one of examples 1-27, wherein said virus is an influenza virus.

Example 33. The method according to any one of examples 1-32, wherein said disease results in influenza like symptoms.

Example 34. A method of selecting subjects for being vaccinated against an infectious disease caused by a pathogen, comprising:
 a. automatically collecting physical proximity information of a subject with other subjects;
 b. generating a predicted likelihood of said subject of transmitting said virus based on said physical proximity information;
 c. generating a score comprising a first score component based on said predicted likelihood of said subject of transmitting said virus;
 d. repeating steps b-c for a plurality of subjects; and
 e. prioritizing vaccination of said subjects according to said score.

Example 35. The method according to example 34, wherein said pathogen is selected from the group consisting of a virus, a bacterium, a fungus and a protozoan.

Example 36. The method according to any one of examples 34-35, wherein said disease is endemic or pandemic.

Example 37. The method according to any one of examples 34-36, wherein said generating said score further comprises a score component based on a nature of a location where said physical proximity information is related.

Example 38. The method according to any one of examples 34-37, wherein said nature of the location is one or more of an open space, a closed space, indoor, outdoor, ventilated indoor space, non-ventilated indoor space and any combination thereof.

Example 39. The method according to any one of examples 34-38, wherein when said physical proximity information is related to a location that is either indoors or in a closed space, then said predicted likelihood of said subject of transmitting said pathogen increases by a factor of between about 10 times to about 100 times. Example 40. The method according to any one of examples 34-39, wherein said physical proximity information is physical proximity data received by means of electronic positioning data of said subject.

Example 41. The method according to any one of examples 34-40, wherein said physical proximity information is physical proximity data of the location of said subject in relation to the location of other subjects.

Example 42. The method according to any one of examples 38-41, wherein said physical proximity data comprises one or more of physical proximity distance data, duration of physical proximity data and/or ambience of physical proximity data.

Example 43. The method according to any one of examples 38-42, wherein said electronic positioning data is one or more of electronic geographical positioning data of said subject, electronic proximity positioning data of said subject relative to other subjects.

Example 44. The method according to any one of examples 38-43, wherein said method further comprises generating a predicted likelihood of said subject contracting said pathogen based on said physical proximity data.

Example 45. The method according to any one of examples 34-44, wherein said generating a score further comprises a second score component based on said predicted likelihood of said subject contracting said pathogen based on said physical proximity data.

Example 46. The method according to any one of examples 38-45, wherein said electronic positioning data is collected using one or more electronic devices.

Example 47. The method according to example 46, wherein said one or more electronic devices are one or more of a smartphone, a tablet, a smartwatch and a dedicated electronic device.

Example 48. The method according to any one of examples 34-47, further comprising vaccinating said subjects according to said score.

Example 49. The method according to any one of examples 34-48, wherein said generating a score further comprises a third score component reflecting relative health risk to said subject if said subject contracts said pathogen.

Example 50. The method according to any one of examples 34-49, wherein said generating a score further comprises a fourth score component reflecting damage to society if said subject contracts said pathogen.

Example 51. The method according to any one of examples 38-50, wherein said electronic positioning data comprises geographical location data.

Example 52. The method according to any one of examples 34-51, wherein said physical proximity information comprises historical location data.

Example 53. The method according to any one of examples 34-52, wherein said generating said score further comprises a component comprising historical health data.

Example 54. The method according to any one of examples 34-53, wherein said generating said score further comprises a component comprising a profession in record of said subject.

Example 55. The method according to any one of examples 34-54, wherein said physical proximity information further comprises information received from a third party.

Example 56. The method according to any one of examples 34-55, wherein said physical proximity information is provided by said subject actively.

Example 57. The method according to any one of examples 34-56, wherein said physical proximity information is provided by said subject passively by means of said one or more electronic devices.

Example 58. The method according to any one of examples 34-57, wherein said pathogen is a virus.

Example 59. The method according to any one of examples 34-58, wherein said virus is a corona virus.

Example 60. The method according to any one of examples 34-58, wherein said virus is SARS-CoV.

Example 61. The method according to any one of examples 34-58, wherein said virus is MERS-CoV.

Example 62. The method according to any one of examples 34-58, wherein said virus is SARS-CoV-2.

Example 63. The method according to any one of examples 1-57, wherein said virus is an influenza virus.

Example 64. The method according to any one of examples 1-63, wherein said disease results in influenza like symptoms.

Example 65. A system for selecting subjects for being vaccinated against an infectious disease caused by a pathogen, comprising:
 a. at least one server comprising a memory;
 b. an analytics module;
 c. a database module;
 d. a simulation module;
said memory in said at least one server comprising instructions, said instructions comprising:
 i. generating, by circuitry, a predicted likelihood of said subject of transmitting said pathogen based on said physical proximity information, for a plurality of subjects;
 ii. selecting subjects of said plurality of subjects for vaccinating based on a prediction that said vaccinating said subjects will reduce a likelihood of spreading of said disease in said plurality of subjects, wherein said selecting is based on said generated predicted likelihood.

Example 66. The system according to example 65, wherein said pathogen is selected from the group consisting of a virus, a bacterium, a fungus and a protozoan.

Example 67. The system according to any one of examples 65-66, wherein said disease is endemic or pandemic.

Example 68. The system according to any one of examples 65-67, wherein said predicted likelihood of said subject of transmitting said pathogen comprises one or more score components used for generating a score.

Example 69. The system according to example 68, wherein said score relates to a predicted likelihood of a group of subjects transmitting said pathogen based on said physical proximity information, and said physical proximity information is a first score component used for said generating said score.

Example 70. The system according to any one of examples 64-69, wherein said generating said score further comprises a score component based on a nature of a location where said physical proximity information is related.

Example 71. The system of example 70, wherein said nature of the location is one or more of an open space, a closed space, indoor, outdoor, ventilated indoor space, non-ventilated indoor space and any combination thereof.

Example 72. The system according to any one of examples 65-71, wherein when said physical proximity information is related to a location that is either indoors or in a closed space, then said predicted likelihood of said subject of transmitting said pathogen increases by a factor of between about 10 times to about 100 times.

Example 73. The system according to any one of examples 65-72, wherein said physical proximity information is physical proximity data received by means of electronic positioning data of said subject.

Example 74. The system according to any one of examples 65-73, wherein said physical proximity information is physical proximity data of the location of said subject in relation to the location of other subjects.

Example 75. The system according to any one of examples 69-74, wherein said physical proximity data comprises one or more of physical proximity distance data, duration of physical proximity data and/or ambience of physical proximity data.

Example 76. The system according to any one of examples 69-75, wherein said electronic positioning data is one or more of electronic geographical positioning data of said subject, electronic proximity positioning data of said subject relative to other subjects.

Example 77. The system according to any one of examples 65-76, wherein said method further comprises generating a predicted likelihood of said subject contracting said pathogen based on said physical proximity data.

Example 78. The system according to any one of examples 64-77, wherein said generating a score further comprises a second score component based on said predicted likelihood of said subject contracting said pathogen based on said physical proximity data.

Example 79. The system according to any one of examples 69-78, wherein said electronic positioning data is collected using one or more electronic devices.

Example 80. The system according to example 79, wherein said one or more electronic devices are one or more of a smartphone, a tablet, a smartwatch and a dedicated electronic device.

Example 81. The system according to any one of examples 64-80, further comprising vaccinating said subjects according to said score.

Example 82. The system according to any one of examples 64-81, wherein said generating a score further comprises a third score component reflecting relative health risk to said subject if said subject contracts said pathogen.

Example 83. The system according to any one of examples 64-82, wherein said generating a score further comprises a fourth score component reflecting damage to society if said subject contracts said pathogen.

Example 84. The system according to any one of examples 69-83, wherein said electronic positioning data comprises geographical location data.

Example 85. The system according to any one of examples 65-84, wherein said physical proximity information comprises historical location data.

Example 86. The system according to any one of examples 64-85, wherein said generating said score further comprises a component comprising historical health data.

Example 87. The system according to any one of examples 64-86, wherein said generating said score further comprises a component comprising a profession in record of said subject.

Example 88. The system according to any one of examples 65-87, wherein said physical proximity information further comprises information received from a third party.

Example 89. The system according to any one of examples 65-88, wherein said physical proximity information is provided by said subject actively.

Example 90. The system according to any one of examples 65-89, wherein said physical proximity information is provided by said subject passively by means of said one or more electronic devices.

Example 91. The system according to any one of examples 65-90, wherein said simulation module further comprises a prediction module.

Example 92. The system according to any one of examples 65-91, wherein said pathogen is a virus.

Example 93. The system according to any one of examples 65-92, wherein said virus is a corona virus.

Example 94. The system according to any one of examples 65-92, wherein said virus is SARS-CoV.

Example 95. The system according to any one of examples 65-92, wherein said virus is MERS-CoV.

Example 96. The system according to any one of examples 65-91, wherein said virus is SARS-CoV-2.

Example 97. The system according to any one of examples 65-91, wherein said virus is an influenza virus.

Example 98. The system according to any one of examples 65-92 wherein said disease results in influenza like symptoms.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
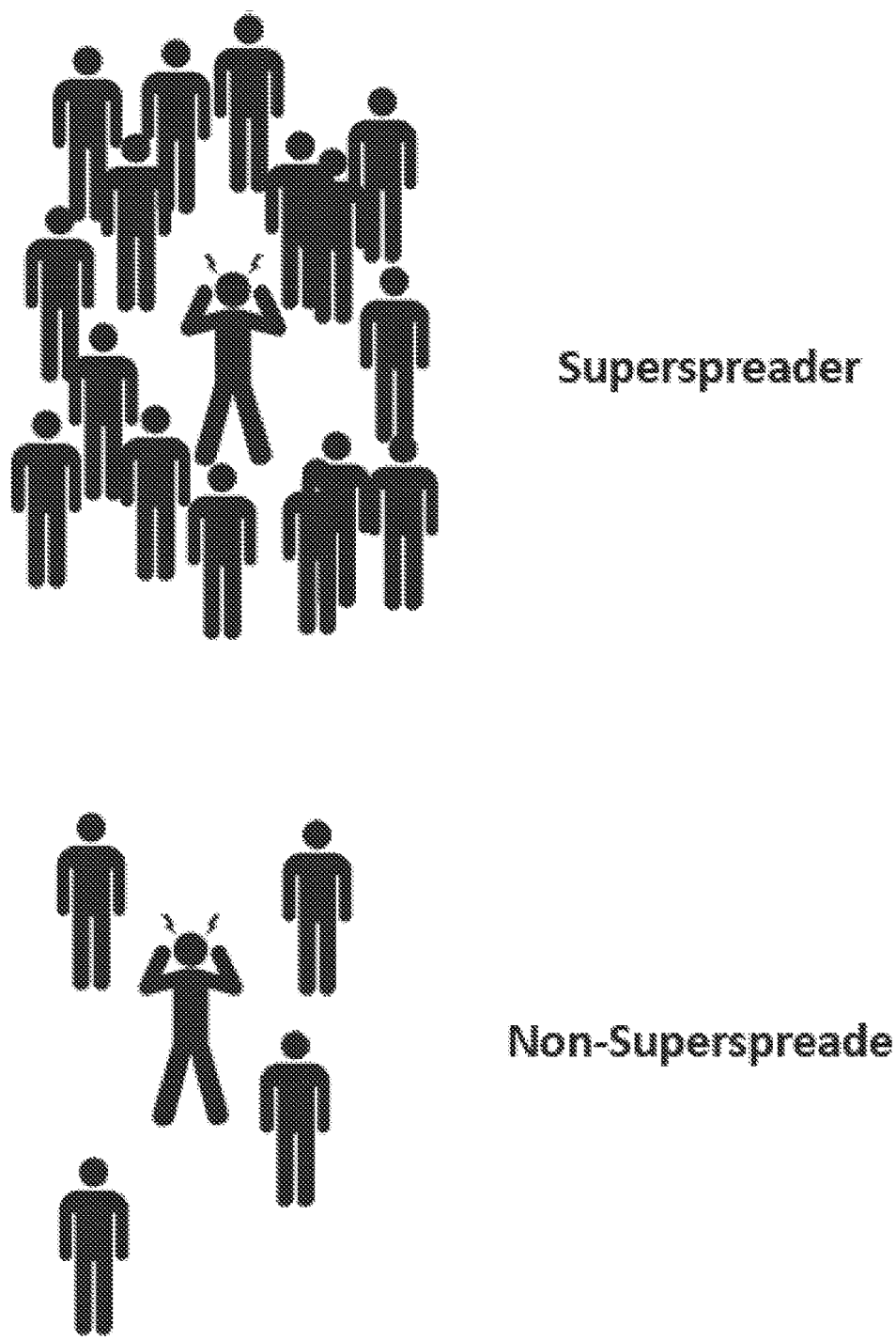
FIG. 1 is a schematic illustration of an exemplary definition of a superspreader, according to some embodiments of the invention.

The present invention, in some embodiments thereof, relates to methods and systems of prioritizing vaccination/ treatment and, more particularly, but not exclusively, to methods and systems of prioritizing vaccination/treatment in a pandemic situation.

Overview

A broad aspect of some embodiments of the invention relates to reduce a pandemic by reducing a k value of infection in addition to and/or at the expense of reducing an R0 value thereof. In some embodiments of the invention, this is achieved by identifying and vaccinating (or otherwise preventing infection by) persons who are potential super spreaders (e.g., people who, on the average, are expected to infect more than the average, for example, 1, 2, 3 or more or intermediate values of standard deviations from such average. This may result in effective lowering of R0 and/or of effective herd immunity. Optionally, people are not measured by actual spreading, but rather by characteristics and/or behavior, which is expected to lead to greater spreading than others. Optionally, such considerations also may be applied to below average in expected spreading, however, such people usually have a smaller overall effect on disease spread.

A broad aspect of some embodiments of the invention relates to using a prediction of individual behavior to decide on vaccination priority for that individual. In some embodiments of the invention, such prediction is based on past behavior of the individual. In some embodiments of the invention, an individual is given a score used for prioritization. In some embodiments of the invention, actual prioritization may be based on a determination of the expected effect of such vaccination on spread of disease. Optionally, this determination is using a simulation of population disease spread. In some embodiments of the invention, however, people are evaluated as individuals.

A broad aspect of some embodiments of the invention relates to soft-fail of vaccination prioritization, which avoids problems caused by imprecise automated tracking methods. In some embodiments of the invention, the use of imperfect information, which, on the one hand does not seriously damage the quality of scoring and, on the other hand, can be used to significantly increase privacy and/or ease of score collection is provided. It is noted that a mistake, for example, of 4%, 8%, 15% or intermediate percentages in score of an individual or missing a potential super spreader will not have a significantly (e.g., a factor of 2 or more) greater effect on a person (e.g., will not send such person into quarantine) and/or the total efficacy of a vaccination process. Also, even after such an effect, it is expected that the overall result is better than naïve or general classification-based vaccination prioritization. In some embodiments of the invention, counting of contacts is allowed to be less precise. In some embodiments of the invention, identification of the quality of the contacts (e.g., indoor/outdoor, coughing behavior, actual proximity and/or existence of protective factors) is allowed to be reduced and optionally carried out using less precise sensing means as provided, for example, by cellphones. Optionally or additionally, the identification of unique contacts is allowed to be less precise.

An aspect of some embodiments of the invention relates to prioritizing vaccinations and/or prophylactic treatments in a pandemic event by identifying potential superspreaders. In some embodiments, potential superspreaders are identified from a population before critical groups have been excluded. In some embodiments, potential superspreaders are identified from a population after critical groups have been excluded. In some embodiments, critical groups are for example, health care providers, essential service provides and high-risk individuals. In some embodiments, potential superspreaders are identified according to one or more of: their usual and/or expected level of activity, their usual and/or expected type of activity, their usual and/or expected health state, their belonging to a closed or open circle of connections, the kind of individuals a certain subject usually meets, the kind of individuals a certain subject has met and their actual sensed behavior. In some embodiments, the entire population (with or without the critical groups), or a part of the population, such as a critical group or other group, are subjected to an analysis which provides each individual with a "superspreader score" (referred hereinafter just as "score") which reflects a likelihood of such a person acting as a superspreader and/or general expected ability of that person to spread the disease. In some embodiments, potential superspreaders are identified according to a score in relation to other scores from the rest of the population. In some embodiments, potential superspreaders are identified according to a score in relation to a predetermined score generated by the system. In some embodiments, identified potential superspreaders having the highest score are vaccinated (or provided with prophylactic treatments) first. It should be appertained that the score may also be weighted with other information, such as criticality for infrastructure, social standing and/or risk form the disease or perceived risk to high-value members of society.

An aspect of some embodiments of the invention relates to prioritizing vaccinations and/or prophylactic treatments in a pandemic event according to a potential level of danger to the society. In some embodiments, the invention relates identification of individuals that, in case they were in a phase of infecting others with an infectious disease/virus/pathogen, it would potentially put everyone else in danger. For example, in the case where a subject is in potential contact with other people and those other people potentially meet a high number of individuals. For example, a subject that interacts face to face with health provider personnel, but does not belong to the health provides network. If that subject becomes infected, he/she can potentially infect a high number of health provider personnel, which will then, potentially, spread the infectious disease/virus/pathogen to a larger population.

An aspect of some embodiments of the invention relates to protecting the privacy of individuals in a population when their information is used for prioritizing vaccinations and/or prophylactic treatments in a pandemic event, optionally also according to a potential level of danger to the society. In some embodiments, actual names of individuals are encrypted and/or anonymized in the system. In some embodiments, only a device of an individual comprises the capabilities to translate between the actual name of the individual and the encrypted/anonymized user name. In some embodiments, the servers of the system comprise high levels of protection and/or encryption for the information stored therein. In some embodiments of the invention, even the device of the user stores a minimum of identifiable information, such as a score, but does not stores actual identities of persons met.

In some embodiments of the invention, private information about a person's activity and/or persons they came in contact with and/or geolocations are maintained on that person's mobile device and used to determine a priority for that person (e.g., by assessing the number of contacts and overall risk of spreading disease due to typical behavior of that person). Optionally, the mobile device is used to broadcast, optionally in an anonymous manner, the score, so that, it may be determined, for example, by a central computer, the distribution of scores across the population. It should be noted that the actual identification of the device and/or user is not needed, just the number of persons with each score, so this can be taken into account together with number and/or availability of vaccine doses, to plan a best dosing schedule. Optionally, the mobile device will receive a predetermined scale of scores from the system, which will be then used by the mobile device to translate the score in view of the scale of scores and communicate the user to get treatment and, optionally, the when and where.

In some embodiments of the invention, once calculated, such dosing schedule is broadcasted and each device can apply its score to the schedule to determine a priority, which is given to the device owner. Optionally, when arriving for a scheduled vaccination, the device owner is required to show that code and, optionally, proof that the telephone belongs to them.

In one example, the local device calculates a score based on a user's medical information and behavior. Optionally is also receives behavior of those that person meets (e.g., transmitted to the device at proximity/contact of devices of those people). In some embodiments, the information is stored without identification of source, except possibly a hash code, which, while can be used to detect that a certain device was "met", it cannot be used to identify the device. In some embodiments, once this score (e.g., risk of contagion) is calculated, the broadcasted information regarding number of vaccinations available and/or number of persons in each class is noted. In some embodiments, this data may be used to determine which vaccination priority the personal device score merits, for example, in the same manner as would be by a central computer (e.g., all scores above x, where there are y people with a score above x and y is the number of available vaccines).

In some embodiments of the invention, broadcasts and data transmissions are digitally signed to prevent tampering. This has a potential advantage of allowing more anonymous transmission method to be used (e.g., Tor).

It should be noted that additionally or alternatively to a central processing, the calculation of the vaccine priority may be distributed between some or all of the mobile devices, for example, using parallelization methods known in the art, which optionally also prevent significant amount of information from passing through any particular device.

In some embodiments of the invention, the device calculates the priority and determines when the device owner should be vaccinated, treated and/or tested. For example, the number and duration of persons in proximity to the device can be used to calculate a risk score. Optionally, medical information, such as susceptibility and/or risk of spreading by coughing is downloaded to the device. This is typically not a significant breach of anonymity, as the identity of the device is typically known to the medical record provider. In some embodiments of the invention, a person can apply to receive a rating, for example, based on importance, job (e.g., healthcare provider), being part of critical infrastructure and/or risk of death. Such rating may be provided in the form of a one-time code, which the person can enter into the device. In this manner, the device can increase or decrease the risk score and/or priority of vaccination, without any central authority being aware of the person's activities.

In some embodiments of the invention, as the device calculates the person's score, it may generate warning to the device owner to avoid or reduce certain behavior. Optionally, such warning is tied to reduction in priority if not heeded. Optionally or additionally, the manually entered rating may affect such warnings. For example, socially promiscuous activity by a doctor may not merit such warning and/or may not reduce the doctor's score (at least while activity is performed at an allowed location, such as a hospital, which location may be indicated as part of the rating), but will generate a warning or a sanction (e.g., if not heeded) to a person without such rating.

In some embodiments of the invention, when deciding if to allow entry of a person into a crowded location, such as a sports arena or a shopping mall, a user may be required to show their rating.

A potential benefit of some embodiments of the invention is that rather than give out vaccination to critical workers, while placing the rest of society in a lockdown (e.g., complete or semi or otherwise restrictions), the total risk of spread may be reduced with a same or smaller number of vaccine doses.

A potential benefit of some embodiments of the invention is self-policing. If a person does not install suitable software for tracking movements, such person may receive a lower priority of treatment/vaccination. Similarly, if a person leaves their device off, then such off-time can be noted and used to affect the score, or even can be used as an indication that that person is not at risk.

In some embodiments of the invention, a process of using the method includes:

(a) Learning the behavior of individuals. This may be done, for example, using existing contact tracking methods and/or using methods as discussed herein. Optionally, such learned behavior is maintained in privacy and/or collected in an anonymous manner or processed as it is collected, to preserve anonymity.

(b) Scoring, which can be based, for example, on number, variety and/or quality of contacts, degree of bridging between subpopulations, risk to individual, risk to others the individual is in contact with, other facts that affect spreading (e.g., chronic cough) and/or existing immunity.

(c) Inviting the individual to be vaccinated, optionally though software on an electronic device used for contact tracking.

(d) Vaccination, optionally verified using the software to identify the person being vaccinated.

An aspect of some embodiments of the invention relates to identifying potential superspreaders without the use of personal data. In some embodiments, superspreaders are identified by providing an anonymous ID to each individual, for example, when a dedicated application/software (referred hereinafter as "application" or "app") is installed in an electronic device. In some embodiments, IDs are exchanged between electronic devices when in proximity to each other (e.g., to indicate a potentially infectious "meeting" of the device holders). In some embodiments, what is transmitted is only a part of such ID (or an indication thereof), which potentially decreases the chances to identify the specific user. In some embodiments of the invention, even the partial IDs substantially unique (e.g., a random number with more possibilities than the number of expected meetings). In some embodiments of the invention, the partial ID is selected to be non-unique, for example, including only 100, 1000, 10,000 or intermediate or smaller or greater possibilities. In some embodiments, prioritizing vaccinations and/or prophylactic treatments in a pandemic event is performed according to a superspreader score calculated by the number of IDs collected by each user.

An aspect of some embodiments of the invention relates to the quality of people an individual meets. In some embodiments of the invention, meeting with a person can be given a higher or lower weight, based on whether that person is himself a super spreader and/or tends to meet super spreaders and/or tends to meet others form many subpopulations. In some embodiments of the invention, when two devices meet, they exchange their own score and/or number of contacts or other information, which is used to generate an indication of how much of a potential superspreader that person is. In some embodiments, such people may be given a higher weight. Optionally or additionally, persons who are from a same subpopulation and/or which have fewer contacts and/or which are met more often, are given a lower weight.

An aspect of some embodiments of the invention relates to assessing the degree of contacts inside a subpopulation and between subpopulations. Society often has bubbles (subpopulations) within which there is a lot of contact within the bubble but considerably less contact between bubbles. In such a context, a person who bridges between bubbles may be a greater threat of disease spread than a person with more overall contacts but most or all within the bubble. In some embodiments of the invention, a method is provided for assessing the degree to which a person is within bubbles and/or bridges between bubbles or between non-bubble subpopulations. For example, the method may be used to distinguish between a first person where 90% of their contacts are within a strongly connected sub-group vs. a person where only 10% of their contacts are to a same strongly sub-group vs a person where 90% of contacts are to a strongly connected sub-group, but there are multiple (exclusive) such subgroups.

In some embodiments of the invention, a distributed method of assessing the degree to which contacts of an individual are within a strongly connected or other type of bubble, is provided. An alternative view of such method is assessing a degree of diffusion, which may be correlated with a degree of propagation of disease.

In some embodiments of the invention, some or all individuals are assigned a second (or more) ID which is transferred to people they meet at a probability lower than 100%. Optionally, when two individuals meet they exchange not only their second ID, but also all second IDs they have collected. As with a regular ID, the second or further IDs may be more or less unique. When an individual device assesses the second IDs it collected, it will tend to have fewer IDs if it is within a bubble (e.g., because it will mainly have IDs within the bubble) than if it interconnects bubbles (e.g., in which case it can have IDs from multiple bubbles). Optionally, the number of second IDs is used as a measure of diffusion of IDs in the contact network. In some embodiments of the invention, the transfer of second IDs can be weighted (and/or probability of transfer adjusted), for example, to better model the likely of transfer of disease, for example, weighted higher for IDs collected in closed spaces, at close distances or IDs received from a device owned by a person with a chronic cough and/or less if owner is known (e.g., recorded as such) to be careful with facemasks or other protective gear. Such weighting may be used additionally or alternatively also for the other scores described herein. The score may be normalized to the period in which the score is collected. Such normalization may be alternatively or additionally applied to score based on the first ID. The normalization may be non-linear (e.g., the score may increase faster at early times) and may be different for different IDs and/or for different individual characteristic values.

In some embodiments of the invention, the probability of transfer is preset (e.g., 0.01%, 0.1%, 1%, 10% or intermediate or smaller or greater percentages). Optionally or additionally, multiple additional IDs are provided, each one transferred at a different probability. Optionally, the preset probability is determined using a simulation. It is noted that with a very small transfer probability, there may not be sufficient diffusion of second ID values, while with a large probability, all individuals will collect all second IDs, given enough time. For example, a simulation of a contact network may be run with different preset transfer values to detect a value which allows to distinguish between typical subpopulation sizes and/or which, within the measurement period, does not reflect diffusion of substantially all second IDs all over the network. Similarly, the degree of uniqueness of the second ID may be selected using such a simulation to ensure that the probability of a same second ID reaching an individual from two different subgroups is sufficiently low (e.g., below 10%).

An aspect of some embodiments of the invention relates to the political issues involved in vaccination prioritization. In some embodiments of the invention, using an objective measure of risk due to behavior allows vaccination selection without (or less) a political fiat of selecting groups and/or reducing political pressure applied to prefer a particular group, as the individuals are treated by prioritization software as individuals and do are not identified as or treated as belonging to particular groups. Also within a particular group, using an automated vaccination prioritization method can be used to reduce friction and argument.

An aspect of some embodiments of the invention relates to encouraging users to use a dedicated application/software for tracking contacts (and optionally identifying potential superspreaders either anonymized or not) by providing vaccinations and/or prophylactic treatments first to those individuals that use the dedicated software. In some embodiments, individuals that use the dedicated software are those individuals that contribute to the overall benefit of the population, therefore are provided with vaccinations and/or prophylactic treatments before those who not.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Definition of the Population

During a pandemic, once a valid vaccine/prophylactic drug becomes available, and the number of vaccines/drug doses is limited or not all available at the same time, the government must decide who will receive first the vaccine/prophylactic treatment. According to studies, governments decide to provide the first doses of the treatment to the group of individuals that belong to:

a) Health care services, for example doctors, nurses, laboratories, hospitals, etc.;

b) Essential service services, for example police, fire fighters, public sector personnel, governmental personnel, etc.; and c) High risk individuals, for example people with high risk of complications, pregnant women, children, etc.

These individuals belong to a group called critical groups, due to the nature of their activity or due to their health status during pandemic times. Usually, critical groups amount to about 2% to about 10% of the total population of a country.

After the critical groups have been vaccinated and/or provided prophylactic treatments, since the number of vaccinations/treatments is limited, there is the question who should be vaccinated/treated next. This is generally true also within a critical group or other group chosen for vaccination, for example, a group of less at risk individuals, such as males aged 50-60.

In some embodiments, the population is defined as a number of individuals between about 10 individuals and about 100 individuals, optionally between about 100 individuals and about 1,000 individuals, optionally between about 1,000 individuals and about 1,000,000 individuals, optionally up to 10,000,000, optionally up to 100,000,000, optionally up to the entire population of earth (e.g., 8 billion).

Principals of Herd Immunity

Before explaining the invention, the notion of herd immunity should be explained. Herd immunity (also called herd effect, community immunity, population immunity, or social immunity) is a form of indirect protection from infectious disease that occurs when a large percentage of a population has become immune (resistant) to an infection, whether through vaccination/prophylactic treatment or previous infections, thereby providing a measure of protection for individuals who are not immune. In a population in which a large proportion of individuals possess immunity, such people being unlikely to contribute to disease transmission, chains of infection are more likely to be disrupted, which either stops or substantially slows the spread of disease. The greater the proportion of immune individuals in a community, the smaller the probability that non-immune individuals will come into contact with an infectious individual, helping to shield non-immune individuals from infection. Individuals can become immune by recovering from an earlier infection or through vaccination/prophylactic treatment. Some individuals cannot become immune because of medical conditions, such as an immunodeficiency or immunosuppression, and for this group herd immunity is a crucial method of protection. Once a certain threshold has been reached, herd immunity gradually eliminates a disease from a population. This elimination, if achieved worldwide, may result in the permanent reduction in the number of infections to zero, called eradication. For example, herd immunity created via vaccination/treatment contributed to the eventual eradication of smallpox in 1977 and has contributed to the reduction of the frequencies of other diseases. Herd immunity does not apply to all diseases, just those that are contagious, meaning that they can be transmitted from one individual to another. Tetanus, for example, is infectious but not contagious, so herd immunity does not apply. Herd immunity was recognized as a naturally occurring phenomenon in the 1930s when it was observed that after a significant number of children had become immune to measles, the number of new infections temporarily decreased, including among susceptible children. Mass vaccination/treatment to induce herd immunity has since become common and proved successful in preventing the spread of many infectious diseases. One of the main problems with achieving herd immunity is that there might be a limited number of vaccinations/treatments available to the population and mass vaccination/treatment is either not possible or it would take a long time to achieve herd immunity while the infectious disease continues to spread.

It is a potential benefit of some embodiments of the invention to provide a method to resolve the problem of who to vaccinate/treat during a pandemic when a low amount of vaccine/treatment doses are available, while still providing an effective herd immunity, optionally by better targeting those individuals likely to pass on disease and vaccinating at least some of them, in a preferential manner.

Definition of Superspreaders

A superspreader is an unusually contagious organism infected with a disease (infectious disease/virus/pathogen). In the context of a human-borne illness, a superspreader is an individual who is more likely to infect others, compared with a typical infected person.

Some cases of superspreading conform to the 80/20 rule, where approximately 20% of infected individuals are responsible for 80% of transmissions, although superspreading can still be said to occur when superspreaders account for a higher or lower percentage of transmissions. In epidemics with such superspreader events (SSEV), the majority of individuals infect relatively few secondary contacts.

Although loose definitions of superspreader events exist, some effort has been made at defining what qualifies as a superspreader event (SSEV). Lloyd-Smith et al. (2005) define a protocol to identify a superspreader event as follows:

a. estimate the effective reproductive number, R, for the disease and population in question;

b. construct a Poisson distribution with mean R, representing the expected range of Z due to stochasticity without individual variation;

c. define an SSEV as any infected person who infects more than Z(n) others, where Z(n) is the nth percentile of the Poisson® distribution.

This protocol defines a 99th-percentile SSEV as a case, which causes more infections than would occur in 99% of infectious histories in a homogeneous population. For example, during the SARS-CoV-1 2002-2004 SARS outbreak from China, epidemiologists defined a superspreader as an individual with at least eight transmissions of the disease. Furthermore, superspreaders may or may not show any symptoms of the disease. In the methods described here, a threshold (or scale) for being a superspreader may be defined manually and/or determined by analyzing actual contact-transmission data collected manually and/or automatically.

Putting aside hospitals, private residences and old-age homes, almost all of these superspreader events (SSEVs) took place in the context of (1) parties, (2) face-to-face professional networking events and meetings, (3) religious gatherings, (4) sports events, (5) meat-processing facilities, (6) ships at sea, (7) singing groups, and (8) funerals.

Factors of Transmission

Superspreaders have been identified who excrete a higher than normal number of pathogens during the time they are infectious. This causes their contacts to be exposed to higher viral/bacterial loads than would be seen in the contacts of non-superspreaders with the same duration of exposure. This medical information may be available for at least some individuals, for example, if the epidemic is a recurring one, such as influenza. In addition, behavioral and medical attributes may also increase infectivity. For example, a chronic cough (or one due to a temporary disease, which may be noted in a person's medical record) may increase the degree to which an individual is contagious. It is noted that coughs and sneezes (and rate thereof) can be detected automatically by a carried device, such as a cellphone, by signal analysis on an automatically and optionally continually (or repeatedly discrete) collected audio signal form the microphone. It is noted that an individual's cellphone or other electronic device may have access to a person medical records, by connecting to an EMR of that individual.

Basic Reproductive Number

The basic reproduction number $R0$ is the average number of secondary infections caused by a typical infective person in a totally susceptible population. The basic reproductive number is found by multiplying the average number of contacts by the average probability that a susceptible individual will become infected, which is called the shedding potential. The average number of contacts may further be weighed by quality of contact (e.g., length, repetition, distance, protective means and/or airflow quality)

$R0 = \text{Number of contacts} \times \text{Shedding potential}$

Individual Reproductive Number

The individual reproductive number represents the number of secondary infections caused by a specific individual during the time that individual is infectious. Some individuals have significantly higher than average individual reproductive numbers and are known as superspreaders. Through contact tracing, epidemiologists have identified superspreaders in measles, tuberculosis, rubella, monkeypox, smallpox, Ebola hemorrhagic fever and SARS.

Co-Infections with Other Pathogens

Studies have shown that men with HIV who are co-infected with at least one other sexually transmitted disease, such as gonorrhea, hepatitis C, and herpes simplex 2 virus, have a higher HIV shedding rate than men without co-infection. This shedding rate was calculated in men with similar HIV viral loads. Once treatment for the co-infection has been completed, the HIV shedding rate returns to levels comparable to men without co-infection. Therefore, it could be hypothesized that in case of viral diseases transmitted through fluids, people with other pathologies, like chronic coughing, could also be defined as superspreaders and are optionally so defined, or weighted accordingly in some embodiments of the invention.

Exemplary Pathogens

In some embodiments, a pathogen may be one or more of a virus (in pl. viruses), bacterium (bacteria), fungus (fungi) or a protozoan (protozoa), for example coronavirus (COVID-19, SARS-CoV-1, SARS-CoV-2, MERS-CoV). In some embodiments, the pathogen may be a virus, and said virus is an influenza virus. In some embodiments, the disease results in influenza like symptoms. It should be understood, that where referred to "virus" and/or "pathogen", any one of an "infectious disease", a "generic or specific pathogen", a "generic or specific virus" are included, and the use of the term "virus" and/or "pathogen" is just to facilitate the explanation and they should include them.

In some embodiments of the invention, the disease is transmitted by respiratory means, for example, aerosol and/or droplets. Optionally, an electronic device, such as a cellphone is used to detect contact which may be sufficient to transmit (e.g., detecting proximity for example, using Bluetooth power; detecting physical activity for example, buy analysis of an audio trace recorded from such device; detecting being indoors or outdoors based on geolocation or based on other sensors on the cellphone that are affected by being indoors (e.g., echoes in audio).

Vaccinations and Prophylactic Treatments

In some embodiments, the term vaccination means the administration of a vaccine to help the immune system develop protection from a disease. In some embodiments, vaccines contain a microorganism or virus in a weakened, live or killed state, or proteins or toxins from the organism. In some embodiments, in stimulating the body's adaptive immunity, they help prevent sickness from an infectious disease. In some embodiments, as stated above, when a sufficiently large percentage of a population has been vaccinated, herd immunity results.

In some embodiments, the term prophylactic treatment means a preventive measure taken to fend off a disease or another unwanted consequence.

In order to facilitate the explanation of the invention, the term "treatment" will be used. It should be understood that when the term "treatment" is used it refers to both vaccinations and prophylactic treatment.

In some embodiments, vaccines are all compounds as disclosed in in the website of the World Health Organization (https://www[dot]who[dot]int/publications/m/item/draft-landscape-of-covid-19-candidate-vaccines), which are all incorporated herein by reference, and which are optionally provided (e.g., as a kit) with software such as described herein and/or provided with instructions for use targeting potential super spreaders detected, for example, using methods and apparatus as described herein, and include the following:

28 Candidate Vaccines in Clinical Evaluation

| COVID-19 Vaccine developer/ manufacturer | Vaccine platform | Type of candidate vaccine | Number of doses | Timing of doses | Route of Administration | Clinical Stage Phase 1 | Phase 1/2 | Phase 2 | Phase 3 |
|---|---|---|---|---|---|---|---|---|---|
| University of Oxford/ AstraZeneca | Non-Replicating Viral Vector | ChAdOx 1-S | 1 | | IM | | PACTR202006 922165132 2020-001072-15 Interim Report | 2020-00 1228-32 | ISRCTN8 9951424 |
| Sinovac | Inactivated | Inactivated | 2 | 0, 14 days | IM | | NCT04383574 NCT04352608 | | NCT0445 6595 |
| Wuhan Institute of Biological Products/ Sinopharm | Inactivated | Inactivated | 2 | 0, 14 or 0, 21 days | IM | | ChiCTR20000 31809 | | ChiCTR20 00034780 |
| Beijing Institute of Biological Products/ Sinopharm | Inactivated | Inactivated | 2 | 0, 14 or 0, 21 days | IM | | ChiCTR20000 32459 | | ChiCTR20 00034780 |
| Moderna/NIAID | RNA | LNP-encapsulated mRNA | 2 | 0, 28 days | IM | NCT04283 461 Interim Report | | NCT044 05076 | NCT0447 0427 |
| BioNTech/Fosun Pharma/Pfizer | RNA | 3 LNP-mRNAs | 2 | 0, 28 days | IM | | 2020-001038-36 ChiCTR20000 34825 | | NCT0436 8728 |

-continued

| COVID-19 Vaccine developer/manufacturer | Vaccine platform | Type of candidate vaccine | Number of doses | Timing of doses | Route of Administration | Clinical Stage Phase 1 | Phase ½ | Phase 2 | Phase 3 |
|---|---|---|---|---|---|---|---|---|---|
| CanSino Biological Inc./Beijing Institute of Biotechnology | Non-Replicating Viral Vector | Adenovirus Type 5 Vector | 1 | | IM | ChiCTR2000030906 Study Report | | ChiCTR2000031781 Study Report | |
| Anhui Zhifei Longcom Biopharmaceutical/Institute of Microbiology, Chinese Academy of Sciences | Protein Subunit | Adjuvanted recombinant protein (RBD-Dimer) | 2 or 3 | 0, 28 or 0, 28, 56 days | IM | NCT04445194 | | NCT04466085 | |
| Institute of Medical Biology, Chinese Academy of Medical Sciences | Inactivated | Inactivated | 2 | 0, 28 days | IM | NCT04412538 | NCT04470609 | | |
| Inovio Pharmaceuticals/International Vaccine Institute | DNA | DNA plasmid vaccine with electroporation | 2 | 0, 28 days | ID | | NCT04447781 NCT04336410 | | |
| Osaka University/AnGes/Takara Bio | DNA | DNA plasmid vaccine + Adjuvant | 2 | 0, 14 days | IM | | NCT04463472 | | |
| Cadila Healthcare Limited | DNA | DNA plasmid vaccine | 3 | 0, 28, 56 days | ID | | CTRI/2020/07/026352 | | |
| Genexine Consortium | DNA | DNA Vaccine (GX-19) | 2 | 0, 28 days | IM | | NCT04445389 | | |
| Bharat Biotech | Inactivated | Whole-Virion Inactivated | 2 | 0, 14 days | IM | | NCT04471519 | | |
| Janssen Pharmaceutical Companies | Non-Replicating Viral Vector | Ad26COVS1 | 2 | 0, 56 days | IM | | NCT04436276 | | |
| Novavax | Protein Subunit | Full length recombinant SARS CoV-2 glycoprotein nanoparticle vaccine adjuvanted with Matrix M | 2 | 0, 21 days | IM | | NCT04368988 | | |
| Kentucky Bioprocessing, Inc | Protein Subunit | RBD-baed | 2 | 0, 21 days | IM | | NCT04473690 | | |
| Arcturus/Duke-NUS | RNA | mRNA | | | IM | | NCT04480957 | | |
| Gamaleya Research Institute | Non-Replicating Viral Vector | Adeno-based | 1 | | IM | NCT04436471 NCT04437875 | | | |
| Clover Biopharmaceuticals Inc./GSK/Dynavax | Protein Subunit | Native like Trimeric subunit Spike Protein vaccine | 2 | 0, 21 days | IM | NCT04405908 | | | |
| Vaxine Ply Ltd/Medytox | Protein Subunit | Recombinant spike protein with Advax™ adjuvant | 1 | | IM | NCT04453852 | | | |
| University of Queensland/CSL/Seqirus | Protein Subunit | Molecular clamp stabilized Spike protein with MF59 adjuvant | 2 | 0, 28 days | IM | ACTRN12620000674932p | | | |
| Institute Pasteur/Themis/Univ. of Pittsburg CVR/Merck Sharp & Dohme | Replicating Viral Vector | Measles-vector based | 1 or 2 | 0, 28 days | IM | NCT04497298 (not yet recruiting) | | | |
| Imperial College London | RNA | LNP-nCoVsaRNA | 2 | | IM | ISRCTN17072692 | | | |
| Curevac | RNA | mRNA | 2 | 0, 28 days | IM | NCT04449276 | | | |
| People's Liberation Army (PLA) Academy of Military Sciences/Walvax Biotech. | RNA | mRNA | 2 | 0, 14 or 0, 28 days | IM | ChiCTR2000034112 | | | |

-continued

| COVID-19 Vaccine developer/ manufacturer | Vaccine platform | Type of candidate vaccine | Number of doses | Timing of doses | Route of Administration | Clinical Stage Phase 1 | Phase 1/2 | Phase 2 | Phase 3 |
|---|---|---|---|---|---|---|---|---|---|
| Medicago Inc. | VLP | Plant-derived VLP adjuvanted with GSK or Dynavax adjs. | 2 | 0, 21 days | IM | NCT04450004 | | | |
| Medigen Vaccine Biologics Corporation/NIAID/ Dynavax | Protein Subunit | S-2P protein + CpG1018 | 2 | 0 28 days | IM | NCT04487210 | | | |

139 Candidate Vaccines in Preclinical Evaluation

| Platform | Type of candidate vaccine | Developer | Coronavirus target | Current stage of clinical evaluation/ regulatory status- Coronavirus candidate | Same platform for non- Coronavirus candidates |
|---|---|---|---|---|---|
| DNA | DNA, engineered vaccine inserts compatible with multiple delivery systems | DIOSynVax Ltd/ University of Cambridge | SARS-CoV-2 and Sarbeco Coronaviruses | Pre-Clinical | |
| DNA | DNA vaccine | Ege University | SARS-CoV2 | Pre-Clinical | |
| DNA | DNA plasmid vaccine RBD & N | Scancell/University of Nottingham/ Nottingham Trent University | SARS-CoV2 | Pre-Clinical | |
| DNA | DNA plasmid vaccine S, S1, S2, RBD & N | National Research Centre, Egypt | SARS-CoV2 | Pre-Clinical | |
| DNA | DNA with electroporation | Karolinska Institute/Cobra Biologics (OPENCORONA Project) | SARS-CoV2 | Pre-Clinical | |
| DNA | DNA with electroporation | Chula Vaccine Research Center | SARS-CoV2 | Pre-Clinical | |
| DNA | DNA | Takis/Applied DNA Sciences/Evvivax | SARS-CoV2 | Pre-Clinical | |
| DNA | Plasmid DNA, Needle-Free Delivery | Immunomic Therapeutics, Inc./EpiVax, Inc./PharmaJet | SARS-CoV2 | Pre-Clinical | SARS |
| DNA | DNA vaccine | BioNet Asia | SARS-CoV2 | Pre-Clinical | |
| DNA | msDNA vaccine | Mediphage Bioceuticals/University of Waterloo | SARS-CoV2 | Pre-Clinical | |
| DNA | DNA vaccine | Entos Pharmaceuticals | SARS-CoV2 | Pre-Clinical | |
| DNA | bacTRL-Spike | Symvivo | SARS-CoV2 | Pre-Clinical | |
| Inactivated | Inactivated + alum | KM Biologics | SARS-CoV2 | Pre-Clinical | JE, Zika |
| Inactivated | Inactivated | Selcuk University | SARS-CoV2 | Pre-Clinical | |
| Inactivated | Inactivated | Erciyes University | SARS-CoV2 | Pre-Clinical | |
| Inactivated | Inactivated whole virus | National Research Centre, Egypt | SARS-CoV2 | Pre-Clinical | |
| Inactivated | Inactivated | Beijing Minhai Biotechnology Co., Ltd. | SARS-CoV2 | Pre-Clinical | |
| Inactivated | TBD | Osaka University/ BIKEN/ NIBIOHN | SARS-CoV2 | Pre-Clinical | |

-continued

| Platform | Type of candidate vaccine | Developer | Coronavirus target | Current stage of clinical evaluation/ regulatory status- Coronavirus candidate | Same platform for non- Coronavirus candidates |
|---|---|---|---|---|---|
| Inactivated | Inactivated + CpG 1018 | Sinovac/Dynavax | SARS-CoV2 | Pre-Clinical | |
| Inactivated | Inactivated + CpG 1018 | Valneva/Dynavax | SARS-CoV2 | Pre-Clinical | |
| Inactivated | Inactivated | Research Institute for Biological Safety Problems, Rep of Kazakhstan | SARS-CoV2 | Pre-Clinical | |
| Live Attenuated Virus | Codon deoptimized live attenuated vaccines | Mehmet Ali Aydinlar University/ Acıbadem Labmed Health Services A.S. | SARS-CoV2 | Pre-Clinical | |
| Live Attenuated Virus | Codon deoptimized live attenuated vaccines | Codagenix/Serum Institute of India | SARS-CoV2 | Pre-Clinical | HAV, InfA, ZIKV, FMD, SIV, RSV, DENV |
| Live Attenuated Virus | Codon deoptimized live attenuated vaccines | Indian Immunologicals Ltd/Griffith University | SARS-CoV2 | Pre-Clinical | |
| Non-Replicating Viral Vector | Sendai virus vector | ID Pharma | SARS-CoV2 | Pre-Clinical | |
| Non-Replicating Viral Vector | Adenovirus-based | Ankara University | SARS-CoV2 | Pre-Clinical | |
| Non-Replicating Viral Vector | Adeno-associated virus vector (AAVCOVID) | Massachusetts Eye and Ear/Massachusetts General Hospital/Ave Xis | SARS-CoV2 | Pre-Clinical | |
| Non-Replicating Viral Vector | MVA encoded VLP | GeoVax/ BravoVax | SARS-CoV2 | Pre-Clinical | LASV, EBOV, MARV, HIV |
| Non-Replicating Viral Vector | Replication defective Simian Adenovirus (GRAd) encoding SARS-CoV-2 S | ReiThera/ LEUKOCARE/ Univercells | SARS-CoV2 | Pre-Clinical | |
| Non-replicating viral vector | MVA-S encoded | DZIF- German Center for Infection Research/IDT Biologika GmbH | SARS-CoV2 | Pre-clinical | Many |
| Non-replicating viral vector | MVA-S | IDIBAPS- Hospital Clinic, Spain | SARS-CoV2 | Pre-clinical | |
| Non-Replicating Viral Vector | adenovirus-based NasoVAX expressing SARS2-CoV spike protein | Altimmune | SARS-CoV2 | Pre-Clinical | influenza |

-continued

| Platform | Type of candidate vaccine | Developer | Coronavirus target | Current stage of clinical evaluation/ regulatory status- Coronavirus candidate | Same platform for non- Coronavirus candidates |
|---|---|---|---|---|---|
| Non- Replicating Viral Vector | Adeno5-based | Erciyes University | SARS-CoV2 | Pre-Clinical | |
| Non- Replicating Viral Vector | 2nd Gen E2b- Ad5 Spike, RBD, Nucleocapsid Subcutaneous & Oral | ImmunityBio, Inc. & NantKwest, Inc. | SARS-CoV2 | Pre-Clinical | flu, Chik, Zika, EBOV, LASV, HIV/SIV, Cancer |
| Non- Replicating Viral Vector | Ad5 S (GREVAX ™ platform) | Greffex | SARS-CoV2 | Pre-Clinical | MERS |
| Non- Replicating Viral Vector | Oral Ad5 S | Stabilitech Biopharma Ltd | SARS-CoV2 | Pre-Clinical | Zika, VZV, HSV-2 and Norovirus |
| Non- Replicating Viral Vector | adenovirus- based + HLA- matched peptides | Valo Therapeutics Ltd | Pan-Corona | Pre-Clinical | |
| Non- Replicating Viral Vector | Oral Vaccine platform | Vaxart | SARS-CoV2 | Pre-Clinical | InfA, CHIKV, LASV, NORV; EBOV, RVF, HBV, VEE |
| Non- Replicating Viral Vector | MVA expressing structural proteins | Centro Nacional Biotecnología (CNB- CSIC), Spain | SARS-CoV2 | Pre-Clinical | Multiple candidates |
| Non- Replicating Viral Vector | Dendritic cell- based vaccine | University of Manitoba | SARS-CoV2 | Pre-Clinical | |
| Non- Replicating Viral Vector | parainfluenza virus 5 (PIV5)- based vaccine expressing the spike protein | University of Georgia/University of Iowa | SARS-CoV2 | Pre-Clinical | MERS |
| Non- Replicating Viral Vector | Recombinant deactivated rabies virus containing S1 | Bharat Biotech/Thomas Jefferson University | SARS-CoV2 | Pre-Clinical | HeV, NiV, EB OV, LASSA, CCHFV, MERS |
| Non- Replicating Viral Vector | Influenza A H1N1 vector | National Research Centre, Egypt | SARS-CoV2 | Pre-Clinical | |
| Non- Replicating Viral Vector | Inactivated Flu-based SARS-CoV2 vaccine + Adjuvant | National Center for Genetic Engineering and Biotechnology (BIOTEC)/ GPO, Thailand | SARS-CoV2 | Pre-Clinical | |
| Protein Subunit | Protein Subunit | Research Institute for Biological Safety Problems, Rep of Kazakhstan | SARS-CoV2 | Pre-Clinical | |

-continued

| Platform | Type of candidate vaccine | Developer | Coronavirus target | Current stage of clinical evaluation/ regulatory status- Coronavirus candidate | Same platform for non- Coronavirus candidates |
|---|---|---|---|---|---|
| Protein Subunit | RBD-protein | Mynvax | SARS-CoV2 | Pre-Clinical | |
| Protein Subunit | Recombinant S protein | Izmir Biomedicine and Genome Center | SARS-CoV2 | Pre-Clinical | |
| Protein Subunit | Peptide + novel adjuvant | Bogazici University | SARS-CoV2 | Pre-Clinical | |
| Protein Subunit | S subunit intranasal liposomal formulation with GLA/3M052 adjs. | University of Virginia | SARS-CoV2 | Pre-Clinical | |
| Protein Subunit | S-Protein (Subunit) + Adjuvant, *E coli* based Expression | Helix Biogen Consult, Ogbomoso & Trinity Immonoefficient Laboratory, Ogbomoso, Oyo State, Nigeria. | SARS-CoV2 | Pre-Clinical | |
| Protein Subunit | Protein Subunit S, N, M & S1 protein | National Research Centre, Egypt | SARS-CoV2 | Pre-Clinical | |
| Protein Subunit | Protein Subunit | University of San Martin and CONICET, Argentina | SARS-CoV2 | Pre-Clinical | |
| Protein Subunit | RBD protein fused with Fc of IgG + Adj. | Chulalongkorn University/ GPO, Thailand | SARS-CoV2 | Pre-Clinical | |
| Protein Subunit | Capsid-like Particle | AdaptVac (PREVENT- nCoV consortium) | SARS-CoV2 | Pre-Clinical | |
| Protein Subunit | Drosophila S2 insect cell expression system VLPs | ExpreS2ion | SARS-CoV2 | Pre-Clinical | |
| Protein Subunit | Peptide antigens formulated in LNP | IMV Inc | SARS-CoV2 | Pre-Clinical | |
| Protein Subunit | S protein | WRAIR/US AMRIID | SARS-CoV2 | Pre-Clinical | |
| Protein Subunit | S protein + Adjuvant | National Institute of Infectious Disease, Japan/Shionogi/ UMN Pharma | SARS-CoV2 | Pre-Clinical | Influenza |
| Protein Subunit | VLP- recombinant protein + Adjuvant | Osaka University/ BIKEN/ National Institutes of Biomedical Innovation, Japan | SARS-CoV2 | Pre-Clinical | |
| Protein Subunit | microneedle arrays S1 subunit | Univ. of Pittsburgh | SARS-CoV2 | Pre-Clinical | MERS |
| Protein Subunit | Peptide | Vaxil Bio | SARS-CoV2 | Pre-Clinical | |

-continued

| Platform | Type of candidate vaccine | Developer | Coronavirus target | Current stage of clinical evaluation/ regulatory status- Coronavirus candidate | Same platform for non- Coronavirus candidates |
|---|---|---|---|---|---|
| Protein Subunit | Adjuvanted protein subunit (RBD) | Biological E Ltd | SARS-CoV2 | Pre-Clinical | |
| Protein Subunit | Peptide | Flow Pharma Inc | SARS-CoV2 | Pre-Clinical | Ebola, Marburg, HIV, Zika, Influenza, HPV therapeutic vaccine, BreastCA vaccine |
| Protein Subunit | S protein | AJ Vaccines | SARS-CoV2 | Pre-Clinical | |
| Protein Subunit | Ii-Key peptide | Generex/ EpiVax | SARS-CoV2 | Pre-Clinical | Influenza, HIV, SARS-CoV |
| Protein Subunit | S protein | EpiVax/Univ. of Georgia | SARS-CoV2 | Pre-Clinical | H7N9 |
| Protein Subunit | Protein Subunit EPV-CoV-19 | EpiVax | SARS-CoV2 | Pre-Clinical | |
| Protein Subunit | S protein (baculovirus production) | Sanofi Pasteur/GSK | SARS-CoV2 | Pre-Clinical | Influenza, SARS-CoV |
| Protein Subunit | gp-96 backbone | Heat Biologics/Univ. Of Miami | SARS-CoV2 | Pre-Clinical | NSCLC, HIV, malaria, Zika |
| Protein Subunit | Peptide vaccine | FBRI SRC VB VECTOR, Rospotrebnadzor, Koltsovo | SARS-CoV2 | Pre-Clinical | Ebola |
| Protein Subunit | Subunit vaccine | FBRI SRC VB VECTOR, Rospotrebnadzor, Koltsovo | SARS-CoV2 | Pre-Clinical | |
| Protein Subunit | S1 or RBD protein | Baylor College of Medicine | SARS-CoV2 | Pre-Clinical | SARS |
| Protein Subunit | Subunit protein, plant produced | iBio/CC- Pharming | SARS-CoV2 | Pre-Clinical | |
| Protein Subunit | Recombinant protein, nanoparticles (based on S- protein and other epitopes) | Saint- Petersburg scientific research institute of vaccines and serums | SARS-CoV2 | Pre-Clinical | |
| Protein Subunit | COVID-19 XWG-03 truncated S (spike) proteins | Innovax/Xiamen Univ./GSK | SARS-CoV2 | Pre-Clinical | HPV |
| Protein Subunit | Adjuvanted microsphere peptide | VIDO- InterVac, University of Saskatchewan | SARS-CoV2 | Pre-Clinical | |
| Protein Subunit | Synthetic Long Peptide Vaccine candidate for S and M proteins | OncoGen | SARS-CoV2 | Pre-Clinical | |
| Protein Subunit | Oral E. coli- based protein expression system of S and N proteins | MIGAL Galilee Research Institute | SARS-CoV2 | Pre-Clinical | |

| Platform | Type of candidate vaccine | Developer | Coronavirus target | Current stage of clinical evaluation/ regulatory status- Coronavirus candidate | Same platform for non- Coronavirus candidates |
|---|---|---|---|---|---|
| Protein Subunit | Nanoparticle vaccine | LakePharma, Inc. | SARS-CoV2 | Pre-Clinical | |
| Protein Subunit | Plant-based subunit (RBD-Fc + Adjuvant) | Baiya Phytopharm/ Chula Vaccine Research Center | SARS-CoV2 | Pre-Clinical | |
| Protein Subunit | OMV-based vaccine | Quadram Institute Biosciences | SARS-CoV2 | Pre-Clinical | Flu A, plague |
| Protein Subunit | OMV-based vaccine | BiOMViS Srl/Univ. of Trento | SARS-CoV2 | Pre-Clinical | |
| Protein subunit | structurally modified spherical particles of the tobacco mosaic virus (TMV) | Lomonosov Moscow State University | SARS-CoV2 | Pre-Clinical | rubella, rotavirus |
| Protein Subunit | Spike-based | University of Alberta | SARS-CoV2 | Pre-Clinical | Hepatitis C |
| Protein Subunit | Recombinant S1-Fc fusion protein | AnyGo Technology | SARS-CoV2 | Pre-Clinical | |
| Protein Subunit | Recombinant protein | Yisheng Biopharma | SARS-CoV2 | Pre-Clinical | |
| Protein Subunit | Recombinant S protein in IC-BEVS | Vabiotech | SARS-CoV2 | Pre-Clinical | |
| Protein Subunit | Orally delivered, heat stable subunit | Applied Biotechnology Institute, Inc. | SARS-CoV2 | Pre-Clinical | |
| Protein Subunit | Peptides derived from Spike protein | Axon Neuroscience SE | SARS-CoV2 | Pre-Clinical | |
| Protein Subunit | Protein Subunit | MOGAM Institute for Biomedical Research, GC Pharma | SARS-CoV2 | Pre-Clinical | |
| Protein Subunit | RBD-based | Neovii/Tel Aviv University | SARS-CoV2 | Pre-Clinical | |
| Protein Subunit | Outer Membrane Vesicle (OMV)-subunit | Intravacc/Epivax | SARS-CoV2 | Pre-Clinical | |
| Protein Subunit | Outer Membrane Vesicle (OMV)-peptide | Intravacc/Epivax | SARS-CoV2 | Pre-Clinical | |
| Protein Subunit | Spike-based (epitope screening) | ImmunoPrecise/ LiteVax BV | SARS-CoV2 | Pre-Clinical | |
| Replicating Viral Vector | YF17D Vector | KU Leuven | SARS-CoV2 | Pre-Clinical | |
| Replicating Viral Vector | Measles Vector | Cadila Healthcare Limited | SARS-CoV2 | Pre-Clinical | |
| Replicating Viral Vector | Measles Vector | FBRI SRC VB VECTOR, Rospotrebnadzor, Koltsovo | SARS-CoV2 | Pre-Clinical | |

-continued

| Platform | Type of candidate vaccine | Developer | Coronavirus target | Current stage of clinical evaluation/ regulatory status- Coronavirus candidate | Same platform for non- Coronavirus candidates |
|---|---|---|---|---|---|
| Replicating Viral Vector | Measles Virus (S, N targets) | DZIF- German Center for Infection Research/ CanVirex AG | SARS-CoV2 | Pre-clinical | Zika, H7N9, CHIKV |
| Replicating Viral Vector | Horsepox vector expressing S protein | Tonix Pharma/Southern Research | SARS-CoV2 | Pre-Clinical | Smallpox, monkeypox |
| Replicating Viral Vector | Live viral vectored vaccine based on attenuated influenza virus backbone (intranasal) | BiOCAD and IEM | SARS-CoV2 | Pre-Clinical | Influenza |
| Replicating Viral Vector | Recombinant vaccine based on Influenza A virus, for the prevention of COVID-19 (intranasal) | FBRI SRC VB VECTOR, Rospotrebnadzor, Koltsovo | SARS-CoV2 | Pre-Clinical | Influenza |
| Replicating Viral Vector | Attenuated Influenza expressing an antigenic portion of the Spike protein | Fundação Oswaldo Cruz and Instituto Buntantan | SARS-CoV2 | Pre-Clinical | Influenza |
| Replicating Viral Vector | Influenza vector expressing RBD | University of Hong Kong | SARS-CoV2 | Pre-Clinical | |
| Replicating Viral Vector | Replication- competent VSV chimeric virus technology (VSVΔG) delivering the SARS-CoV2 Spike (S) glycoprotein. | IAVI/Merck | SARS-CoV2 | Pre-Clinical | Ebola, Marburg, Lassa |
| Replicating Viral Vector | VSV-S | University of Western Ontario | SARS-CoV2 | Pre-Clinical | HIV, MERS |
| Replicating Viral Vector | VSV-S | Aurobindo | SARS-CoV2 | Pre-Clinical | |
| Replicating Viral Vector | VSV vector | FBRI SRC VB VECTOR, Rospotrebnadzor, Koltsovo | SARS-CoV2 | Pre-Clinical | |
| Replicating Viral Vector | VSV-S | Israel Institute for Biological Research/ Weizmann Institute of Science | SARS-CoV2 | Pre-Clinical | |
| Replicating Viral Vector | M2-deficient single replication (M2SR) influenza vector | UW- Madison/ FluGen/Bharat Biotech | SARS-CoV2 | Pre-Clinical | influenza |

| Platform | Type of candidate vaccine | Developer | Coronavirus target | Current stage of clinical evaluation/regulatory status- Coronavirus candidate | Same platform for non-Coronavirus candidates |
|---|---|---|---|---|---|
| Replicating Viral Vector | Newcastle disease virus vector (NDV-SARSCoV-2/Spike) | Intravacc/Wageningen Bioveterinary Research/Utrecht Univ. | SARS-CoV2 | Pre-Clinical | |
| Replicating Viral Vector | Avian paramyxovirus vector (APMV) | The Lancaster University, UK | SARS-CoV2 | Pre-Clinical | |
| RNA | Self-amplifying RNA | Gennova | SARS-CoV2 | Pre-Clinical | |
| RNA | mRNA | Selcuk University | SARS-CoV2 | Pre-Clinical | |
| RNA | LNP-mRNA | Translate Bio/Sanofi Pasteur | SARS-CoV2 | Pre-Clinical | |
| RNA | LNP-mRNA | CanSino Biologics/Precision NanoSystems | SARS-CoV2 | Pre-Clinical | |
| RNA | LNP-encapsulated mRNA cocktail encoding VLP | Fudan University/Shanghai JiaoTong University/RNACure Biopharma | SARS-CoV2 | Pre-Clinical | |
| RNA | LNP-encapsulated mRNA encoding RBD | Fudan University/Shanghai JiaoTong University/RNACure Biopharma | SARS-CoV2 | Pre-Clinical | |
| RNA | Replicating Defective SARS-CoV-2 derived RNAs | Centro Nacional Biotecnología (CNB-CSIC), Spain | SARS-CoV2 | Pre-Clinical | |
| RNA | LNP-encapsulated mRNA | University of Tokyo/Daiichi-Sankyo | SARS-CoV2 | Pre-Clinical | MERS |
| RNA | Liposome-encapsulated mRNA | BIOCAD | SARS-CoV2 | Pre-Clinical | |
| RNA | Several mRNA candidates | RNAimmune, Inc. | SARS-CoV2 | Pre-Clinical | |
| RNA | mRNA | FBRI SRC VB VECTOR, Rospotrebnadzor, Koltsovo | SARS-CoV2 | Pre-Clinical | |
| RNA | mRNA | China CDC/Tongji University/Stermina | SARS-CoV2 | Pre-Clinical | |
| RNA | LNP-mRNA | Chula Vaccine Research Center/University of Pennsylvania | SARS-CoV2 | Pre-Clinical | |
| RNA | mRNA in an intranasal delivery system | eTheRNA | SARS-CoV2 | Pre-Clinical | |

| Platform | Type of candidate vaccine | Developer | Coronavirus target | Current stage of clinical evaluation/regulatory status-Coronavirus candidate | Same platform for non-Coronavirus candidates |
|---|---|---|---|---|---|
| RNA | mRNA | Greenlight Biosciences | SARS-CoV2 | Pre-Clinical | |
| RNA | mRNA | IDIBAPS-Hospital Clinic, Spain | SARS-CoV2 | Pre-Clinical | |
| VLP | VLP | Bezmialem Vakif University | SARS-CoV2 | Pre-Clinical | |
| VLP | VLP | Middle East Technical University | SARS-CoV2 | Pre-Clinical | |
| VLP | Enveloped Virus-Like Particle (eVLP) | VBI Vaccines Inc. | SARS-CoV-2, SARS-CoV, & MERS-CoV | Pre-Clinical | CMV, GBM, Zika |
| VLP | S protein integrated in HIV VLPs | IrsiCaixa AIDS Research/IRTA-CReSA/Barcelona Supercomputing Centre/Grifols | SARS-CoV2 | Pre-Clinical | |
| VLP | VLP + Adjuvant | Mahidol University/The Government Pharmaceutical Organization (GPO)/Siriraj Hospital | SARS-CoV2 | Pre-Clinical | |
| VLP | Virus-like particles, lentivirus and baculovirus vehicles | Navarrabiomed, Oncoimmunology group | SARS-CoV2 | Pre-Clinical | |
| VLP | Virus-like particle, based on RBD displayed on virus-like particles | Saiba GmbH | SARS-CoV2 | Pre-Clinical | |
| VLP | ADDomerTM multiepitope display | Imophoron Ltd and Bristol University's Max Planck Centre | SARS-CoV2 | Pre-Clinical | |
| VLP | Unknown | Doherty Institute | SARS-CoV2 | Pre-Clinical | |
| VLP | VLP | OSIVAX | SARS-CoV1 SARS-CoV2 | Pre-Clinical | |
| VLP | eVLP | ARTES Biotechnology | SARS-CoV2 | Pre-Clinical | malaria |
| VLP | VLPs peptides/whole virus | Univ. of Sao Paulo | SARS-CoV2 | Pre-Clinical | |

In some embodiments, vaccines are all compounds as disclosed in in the website of ClinicalTrials.gov (https://clinicaltrials[dot]gov/ct2/results?cond=COVID-19), which are all incorporated herein by reference. Other vaccines may be used as well.

In some embodiments, treatment can be the use of Hydroxychloroquine and azithromycin plus zinc.

In some embodiments, vaccines include the vaccine developed by the Moscow-based Gamaleya Institute, named Sputnik-V.

In some embodiments, providing a treatment as disclosed above to healthy subjects can be understood as prophylactic treatment and/or vaccination.

Exemplary Classification of Superspreader

Referring now to FIG. 1, showing a schematic representation of a definition of superspreader, according to some embodiments of the invention. In addition to the notion that a superspreader might be identified as a person who excretes a higher than normal number of pathogens during the time they are infectious, a superspreader is a person who may excrete a normal (or low) number of pathogens during the time they are infectious but this person is potentially and/or effectively in contact with a high number of people, therefore potentially infecting the same or more number of people as a person who excretes a higher than normal number of pathogens, as schematically shown for example in FIG. 1. Following this logic, according to some embodiments of the invention, a superspreader is further identified according to the number of people he/she can potentially be in contact with, is expected or estimated to be in contact with (e.g., based on number he has been in contact with), no matter the level of excretion of said person.

Super-Spreading Potential Score

In accordance with some embodiments of the invention, there are provided methods and systems of providing subjects in a population with a "superspreading score", which will help to provide the order in which the subjects, optionally in groups of subjects, will receive treatments. In some embodiments, the higher the score the higher the potential of each individual to spread the disease. In some embodiments, the higher the score, the earlier the individual should receive the treatments. In some embodiments, a potential advantage of vaccinating/treating individuals having the higher superspreading score is to block potential intersections where a higher number of individuals might be infected by the potential superspreaders, and this is done by vaccinating individuals with potentially and/or actual higher chances to meet other people, and optionally also in relation to other individuals (for example by normalization of the data). In some embodiments, a potential advantage of this method is that a population will potentially reach faster a state of herd immunity, as the provision of treatments continues.

Figure 2:
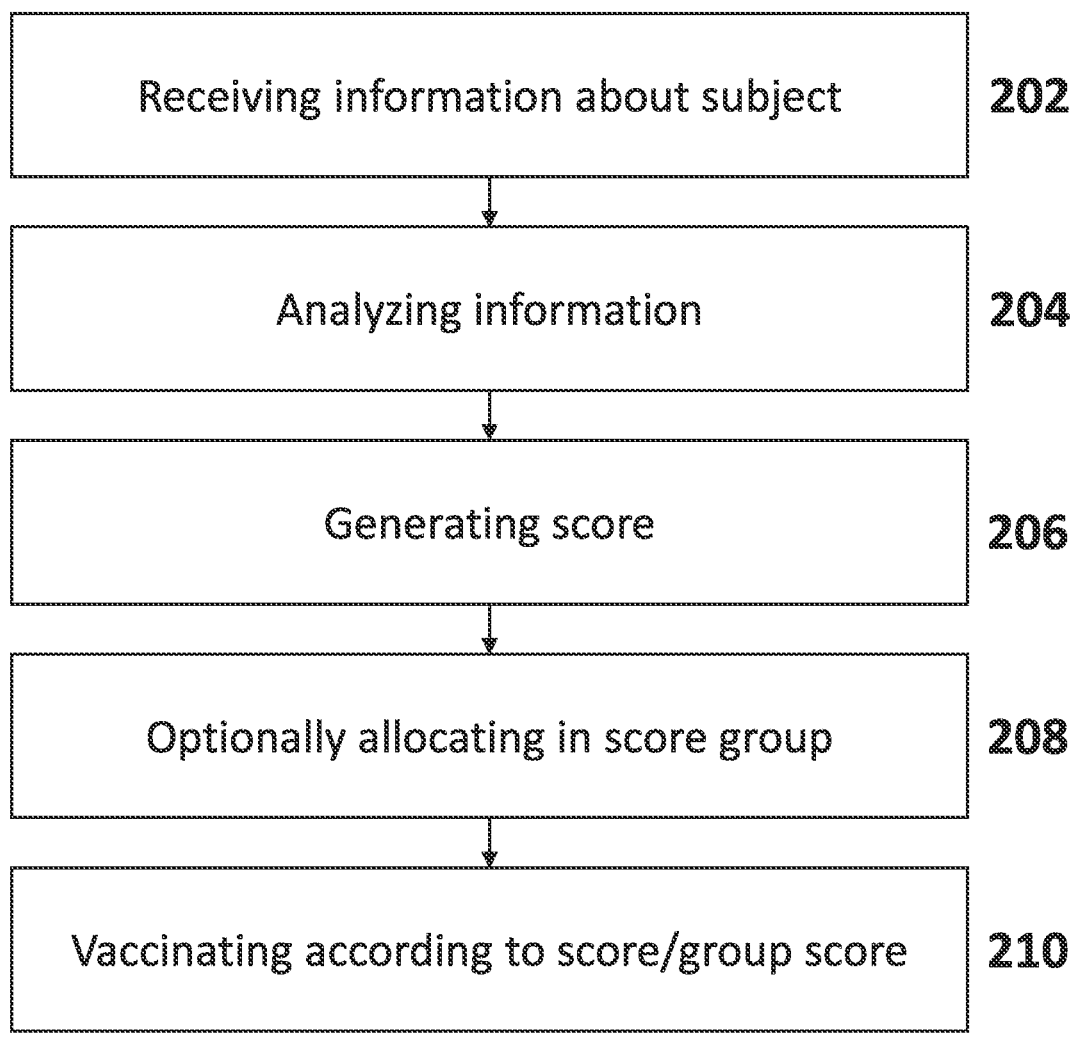
FIG. 2 is a flowchart of an exemplary embodiment of the invention, according to some embodiments of the invention.

Referring now to FIG. 2, showing a flowchart of an exemplary embodiment of the invention. In some embodiments, the system and methods are based on the following: receiving information about a subject 202, analyzing the received information 204, generating a score 206 based on the information, optionally allocating the subject based to the score to a score group 208, and providing treatment according to the score and/or according to the score group 210. As will be shown below, some or all of the receiving and generating may be performed on an electronic device of subject 202.

Exemplary Factors Influencing the Score

In some embodiments, the score is generated utilizing one or more factors and/or components, each influencing the final score by either adding or subtracting from the score. In some embodiments, the one or more factors can influence the score in a linear matter (increasing/decreasing the score linearly, for example +1 to the score or −2 to the score) and/or one or more factor can affect the score in a weighted matter, as will be further explained below. Exemplary factors and/or components are one or more of the following:

Profession in Record of the Individual

In some embodiments, the profession of the individual is correlated with a potential number of people the person might be in contact with during a regular day of operation. In some embodiments, individuals that potentially must meet many people due to their profession will receive a high score. For example, cashiers at the supermarket, vendors in markets, bus drivers, delivery people, technicians, librarians, etc. In some embodiments of the invention, the profession information is used to estimate a contact quality score, for example, doctors being more careful with PPE than teachers. It is a particular feature of some embodiments of the invention, that differences within such a group, such as between different doctors, are determined. In some embodiments of the invention, a subject's score is modified according to the profession, for example, to compensate for criticality of the subject and/or to lack of control of the subject (e.g., a bus driver) over number of contacts.

In some embodiments of the invention, a subject provides profession information or other information used to adjust scoring by scanning a barcode (or other machine-readable item such as a barcode or RFID chip identity card) which is optionally digitally signed with such information. Optionally, this allows the device to know the profession information, but may not allow the device and/or the information provider to link the request for data to a particular individual. Thus potentially maintaining privacy.

Characteristics of Population Potentially to Meet

In some embodiments, the kind of population that a certain subject can potentially meet will either increase or decrease the score. For example, teachers that meet many children will be provided with a higher score, since if and once the children are infected by the teacher, the children return home and potentially infect their families. While for example, a doctor that works at a prison would potentially receive a lower score since the incarcerated people in the prison are not leaving and probably will not infect anyone else (the infection is contained to the prison alone).

Another example, if a certain subject meets only a certain number of individuals, and mainly only those individuals, for example a subject in a close community, then that subject will receive a lower score.

Characteristics of Population that a Subject Actually Met

In some embodiments, if a certain subject meets people that were identified as superspreaders, this will influence the score by increasing their score, also when compared to subjects that do not meet superspreaders and/or regular people. In some embodiments, the information regarding meeting a superspreader is performed between the mobile devices in an anonymous matter, for example, as will be further explained below.

The Nature of the Locations

In some embodiments, the nature of a location means if it is in a closed place, if it is in an open space, if it is indoors, if it is outdoors, quality of ventilation or any combination thereof. In some embodiments, the nature of the locations can drastically change the score given to a subject. It has been shown that a likelihood of a subject transmitting a pathogen increases by a factor of between about 10 times to about 100 times when the location is indoors and/or in a closed space. This is because the risk of infection is increased due to the possible buildup of the airborne pathogen-carrying droplets, the pathogen likely higher stability in indoor air, and/or a larger density of people.

In some embodiments, if the location is indoors or in a closed location, then the score given to the subject for a contact will increase.

In some embodiments, other factors that influence the increment or reduction of the likelihood of a subject transmitting a pathogen indoors are one or more of ventilation rate, use of natural ventilation, avoidance of air recirculation and use of air filters.

In some embodiments, the system will comprise information on indoor locations related to the ventilation rate, use of natural ventilation, avoidance of air recirculation and use of air filters. In some embodiments, an indoor place comprising a high ventilation rate score will provide a lower score to the individual when compared to a place having a low ventilation rate score.

The Kind of Places Usually Visited by the Subject

In some embodiments, subjects that are prone to frequent religious or secular events, like in a synagogue, a church or a mosque or a dancing venue, where the people are in close proximity to each other, and talk, pray, sing and/or breathe deeply and/or mingle more, will receive a higher score (e.g., for such a contact event) than those who do not frequent religious events. In some embodiments, similarly to above, also subject that are prone to frequent sports events will receive a higher score. In some embodiments, places that are frequented regularly by a large quantity of individuals (including public transportation, detectable for example, by geolocation and/or regular start-stop movement that matches a public transportation profile and/or base don payment activity using the tracking electronic device) will be marked as points on interest for the potential spreading of the infectious disease/virus/pathogen, and subjects that frequent those places will receive a higher score.

The Length of Time at the Locations

In some embodiments, the length that a subject stays in one place will contribute to the determination of the probability to infect others and/or to be infected by others. For example, a subject that visits many places but stays there just for a minute or two might receive a lower score (e.g., for a contact event) than a person that stays for longer in a few places, since staying longer at one place potentially increases the chances to infect and/or be infected.

Historical Geolocation Data of the Individual

In some embodiments, historical data of the location of an individual is used to assess the potential geolocation activity of that specific individual. For example, Google Maps® data saved in servers, Waze® data saved in servers, and other geolocation applications configured to save geolocation activity data. In some embodiments, individuals having a high volume of movement data (and/or high usage of public transportation) in their historical geolocation data will receive a high score. In some embodiments, the historical data is used to further assess a reliability of change in behavior of a subject, for example to determine if to increase score in cases where the actual geolocation data changes drastically (for example if there is a risk that a subject wants a higher score to receive the vaccine and increases his movements to achieve so).

Actual Geolocation Data of the Individual

In some embodiments, actual measured geolocation data of each individual is monitored to assess their potential to meet other people. In some embodiments, people which show high number movements during the day in areas where other people are located will receive a high score. In some embodiments, actual geolocation data of each individual is monitored using one or more of:

1. Electronic devices, for example the location provided by the GPS of their own cellphones;
2. Using face recognition technology based on one or more of: a) video surveillance data received from available sources, for example street cameras, ATM's, private surveillance cameras in stores, buildings and houses, etc.; b) social media.
3. Digital activity, for example credit card usage, IP address used while using a computer or an electronic device, antennas that receive data while performing a phone call.

Optionally or additionally, such actual geolocation data is used instead of or in addition to actually identifying contact between people.

Historical Medical Data of the Individual

In some embodiments, historical medical data of each individual is assessed to provide a score. For example, as mentioned above, individuals with chronic coughing will receive a high score since they have potentially a higher chance to transmit the infectious disease/virus/pathogen. In some embodiments, individuals having a background condition that enhances the chances of transmitting the disease will receive a high score.

Actual Medical Data of the Individual

In some embodiments, during the pandemic, every new medical data concerning each individual is monitored to assess if the new data indicates a change in the medical status of the individual regarding their potential to infect others. Using the example above, if a person is diagnosed with chronic coughing it will increase their score (e.g., in general and/or per contact).

Third Party Information Regarding the Individual

In some embodiments, third party information from individuals informing on others will be assessed to decide if the information needs to affect the score. For example, if a third party informs that a person that showed low movement data and received a low score is actually performing many movements, once the information is verified, the score will change accordingly. The contrary is also valid, for example, a third party informed that a person that showed high movement data and received a high score is actually staying at home, once the information is verified, the score may change accordingly.

Dedicated Mandatory App

In some embodiments, in view of the pandemic, the government may order the citizens to install a dedicated application on their smartphones (or other smart devices like tablets, smart watches, smart glasses, etc.) to help the government with the logistics of the vaccination procedures. In some embodiments, the government (or other body) provides the public with such dedicated smart devices. In some embodiments, the app and/or the smart device is configured to inform on the user's location at all times and to communicate with adjacent smart devices (via Bluetooth for example) to assess the interactions between users, for example vicinity between users, movement of users, etc.). In some embodiments of the invention, already existing software may be used, for example, both android and is based cellphones have software (e.g., as an operating system service) which can detect proximity of others and such software may be used or improved to provide functionality as described herein.

In some embodiments, such app can be used to provide information regarding how many unique people the user meets. For example, a certain user can meet many people but they are all the same people all the time. While another user can meet fewer people but each one is a different individual. In some embodiments, the second user may potentially receive a higher score and therefore receive treatment first. In some embodiments, such app and/or smart devices are also used to assess the progression of the vaccination procedures and the efficacy of the vaccination procedure. In some embodiments, individual data arriving from each user is coupled with their health information (sick, vaccinated, recovered, etc.) to further assess the progression of the vaccination procedures and the efficacy of the vaccination procedure. Optionally, if the persons met by a user are vaccinated or otherwise determined to be immune, such contacts may not count and/or be weighted lower.

In some embodiments, the app will be also used to send personalized communication to the users, for example, to come and be vaccinated. In some embodiments, in view of the information received from the app, specific actions are taken, for example, send a communication to the user to enhance his awareness to behavioral rules during pandemic, to come and be vaccinated, to avoid certain locations, which are at high risk of contagion.

Dedicated Voluntary App

In some embodiments, in view of the pandemic, the population is encouraged to install a dedicated app, where those that do install the app are rewarded. In some embodiments, the reward is priority to receive treatment.

Monitoring Behavior of Subject

In some embodiments, the behavior of the subject is monitored in relation to safety features performed by the subject, for example, wearing a mask (e.g., analyzing images taken during calls or other looking at screen of cellphone), washing his hands (e.g., analyzing sounds of water running or movement by a smartwatch), keeping social distancing (e.g., based on Bluetooth power levels and/or NFC detection), moving between multiple locations, etc. In some embodiments, these are monitored using the same devices/methods as disclosed above.

Exemplary Scoring Method

In some embodiments, each individual in a population (e.g., above 100, 1000, 10000 and/or 100000 individuals) is provided with a score defining the potential level of superspreading of each individual. In some embodiments, scores are defined as number of contacts (see herein), and the number of contacts that are counted are from about 10 to about 100, optionally from about 100 to about 1000, optionally from about 1000 to about 10000, for example 100, 400, 1000, 2000, 10000 or intermediate or greater numbers. In some embodiments, a high score defines a high potential of superspreading, while a low score defines a low potential of superspreading. In order to facilitate the explanations of the invention, a scoring scale from 0 to 100 will be used. It should be understood that other scales can be used, like heat-map scoring, decimal order scales, etc., all of which are included in the scope of the invention. In some embodiments of the invention, the score is open ended. In some embodiments of the invention, the score is normalized, for example, to other scores. The normalization need not be linear. In some embodiments of the invention, the score is a scalar. In some embodiments of the invention, the score is multi-dimensional, for example, including a superspreader potential dimension and a variability in behavior dimension)

Figure 3:
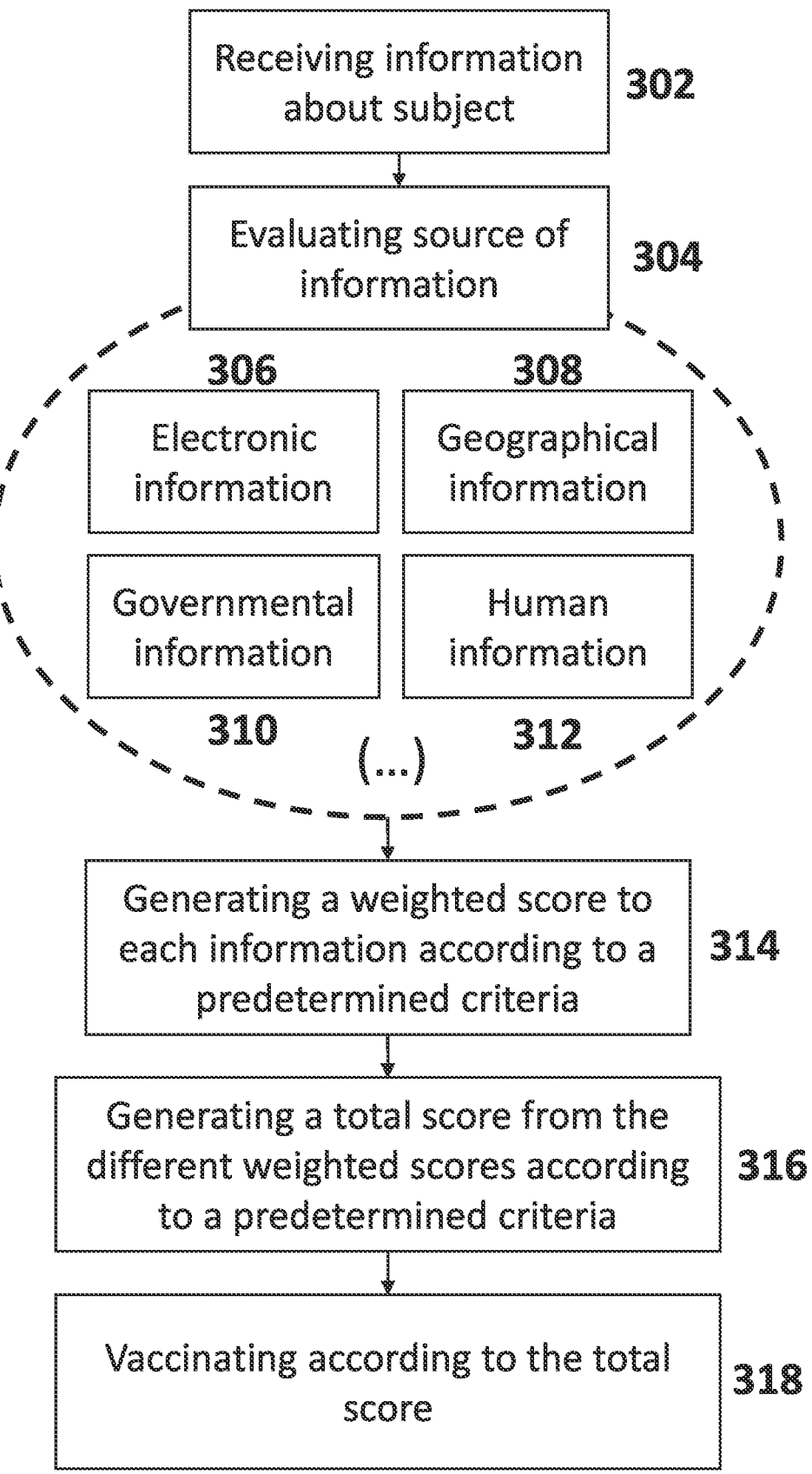
FIG. 3 is a schematic flowchart of a method of calculating a weighted score, according to some embodiments of the invention.

In some embodiments, the score is calculated using weighted scoring models, in which one or more factors and/or components are assessed according to the received information data. Referring now to FIG. 3, showing a schematic flowchart of a method of calculating a weighted score, according to some embodiments of the invention. In some embodiments, the system receives information data about a subject 302. In some embodiments, the information data is divided according to the source of the information data 304, for example, electronic information 306 from smartphones, cameras, credit card information, etc., geographical information 308, for example from GPS or cell towers, governmental information 310, for example from the census bureau or EMR (electronic medical records), human information 312, for example from other individuals calling an providing the information about other individuals, and one or more of the factors and/or components disclosed above. In some embodiments, the system then calculates a weighted score of each information, optionally according to a predetermined criterion 314. In some embodiments, the system then generates a total score from the different weighted scores, optionally according to a predetermined criterion 316. In some embodiments, the system then provides a list comprising an order of treatment, which is then used to actually treat the population 318.

In some embodiments, the score comprises a plurality of components, for example predicted likelihood of a subject transmitting an infectious disease/virus/pathogen, predicted likelihood of a subject contracting an infectious disease/virus/pathogen, relative health risk to a subject if said subject contracts a infectious disease/virus/pathogen, damage to society if the subject contracts a infectious disease/virus/pathogen; one or more of the above optionally in view of physical proximity data to other subjects.

In some embodiments, physical proximity data of a subject with other subjects is calculated by including one or more of:

1. The number of subjects the subject potentially is in contact with;
2. The potential and/or actual distance of the subject to the other subjects;
3. The time length of the potential and/or actual encounter of the subject with the other subjects.

In some embodiments of the invention, the score is updated for and/or after each contact event. In some embodiments of the invention, update is at end of the day, which may allow aggregating multiple meetings with a same person. Optionally or additionally, the score is updated per a set of contact events. In some embodiments of the invention, the score is calculated after all contact events are collected, for example, based on an analysis of a contact-network to identify individuals, which, if vaccinated, will best stop infection. Such analysis may be carried out by simulating the contact network and trying out various vaccination schemes and/or removal of various individuals and/or sets of individuals.

From Score to Treatment

In some embodiments, once the scoring of each individual is achieved, or optionally the scoring of a high number of individuals of the population, a list is created having the order in which each individual will receive the treatment. In some embodiments, the list is optionally divided by groups, for example, all the individuals that scored between 100 and 90 are grouped in group A, which will receive first the treatments. Then all the individuals that scored between 90 and 80 are grouped in group B, which will receive second the treatments, and so on.

Informing the Public

In some embodiments, once the list is made, individuals will be informed on when and where to go and receive the treatments, for example, by means of emails, dedicated apps in their cellphones, over the media, etc.

Exemplary Simulations

In some embodiments, models and simulations are run in dedicated computers, for example, to assess the potential progression of the treatments and the probable time to reach herd immunity and/or select values for various parameters. In some embodiments, simulations include the insertion of one or more of actual data received from individuals, simulated data of/from individuals (in case is necessary to run probable scenarios). In some embodiments, evaluations and models utilize one or more of neural networks, machine learning and dedicated simulations.

In some embodiments, the simulations take under consideration and model the probability of the treatments to work (or not work) on the individual.

In some embodiments, the simulations take under consideration and model the kind of population that a certain subject can potentially meet and the potential population those individuals will potentially meet afterwards. For example, teachers that meet many children will be provided with a higher simulated score, since if and once the children are infected by the teacher, the children return home and potentially infect their families. While for example, a doctor that works at a prison would potentially receive a lower simulated score since the incarcerated people in the prison are not leaving and probably will not infect anyone else (the infection is contained to the prison alone).

In some embodiments, simulations are performed to evaluate parameter values used to identify a superspreader and possibly how to differentiate them from regular individuals.

Exemplary Spreading Network

Figure 4:
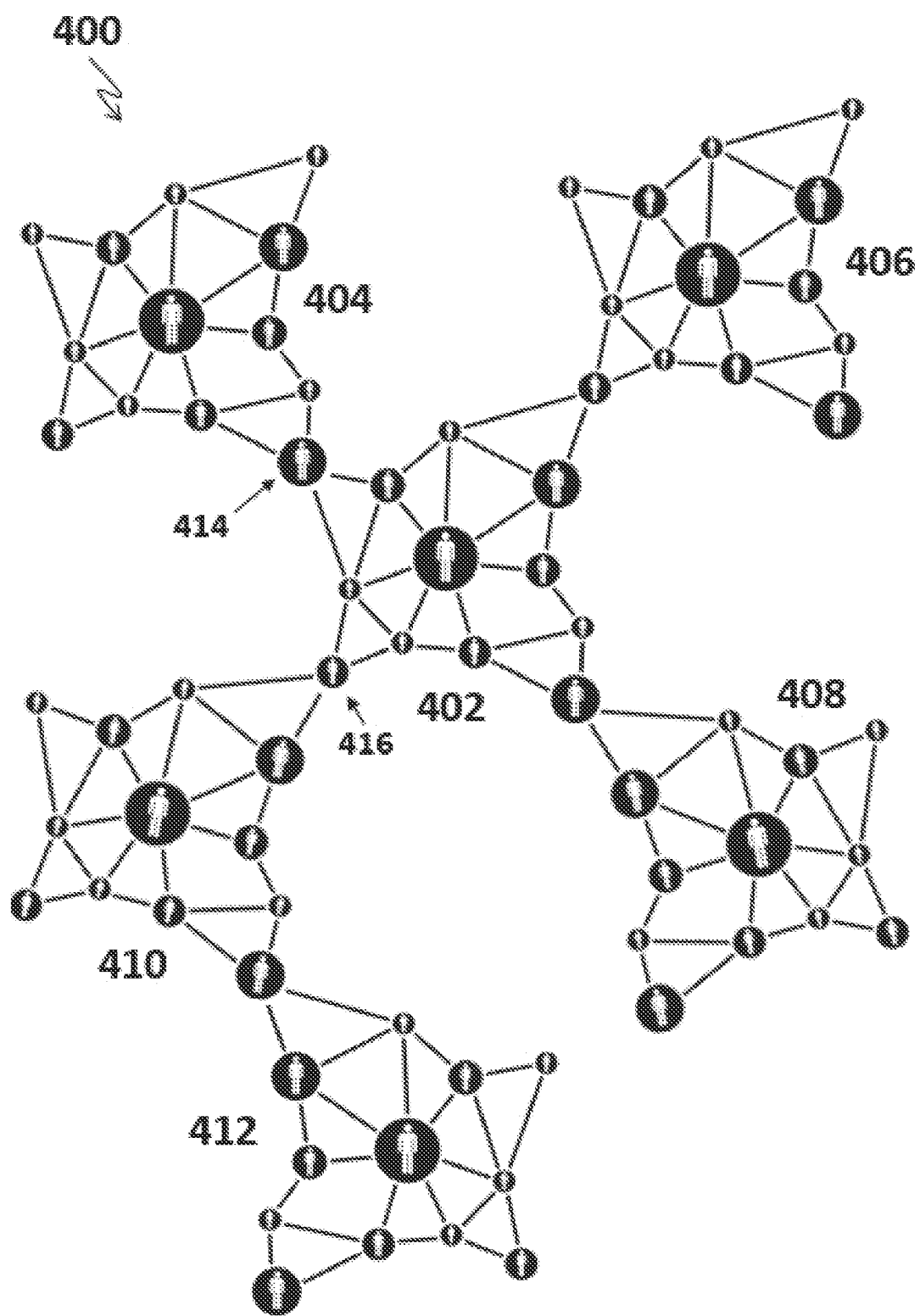
FIG. 4 is a schematic representation of an exemplary spreading network, according to some embodiments of the invention.

In some embodiments, before, during and/or receiving the information regarding the individuals in the whole population, a network 400 of the population is created, as shown for example in FIG. 4. In some embodiments, the network is constantly updated by the system. In some embodiments, the network is used to determine the potential spreading of the infectious disease/virus/pathogen if a certain individual is infected. In some embodiments, when possible, clusters in the network are identified, for example clusters 402 through 412 in network 400. In some embodiments, when evaluating whom to provide treatments, the system assesses the individuals in the clusters and performs analysis and simulations to choose which individuals to treat (e.g., individuals that interconnect clusters). In some embodiments, this is performed in addition to the scoring performed and generated on each single individual. For example, it can be seen that individual 414 belongs to both clusters 402 and 404, thereby creating a potential bottleneck (or bridge) between clusters. Therefore, it would be advantageous to treat individual 414 to protect cluster 404 from potential infections coming from cluster 402. Same logic is applied to individual 416. Treating individual 416 can potentially protect clusters 410 and 412 from potential infections coming from cluster 402. In some embodiments, the system identifies potential key individuals and/or potential key groups of individuals to treat first in order to potentially protect clusters of individuals. In some embodiments, the systems performs this assessment in view of the number of doses available to the population. For example, if there is a large number of doses, instead of treating the individuals located in the bottlenecks, it might be advantageous to treat first all individuals in the cluster 402, thereby potentially protecting the rest of the clusters from infection.

In one example, the system selectively removes individuals to identify which set of N individuals (e.g., where N is the number of doses to be used) is best to remove. This can be done using brute force approaches, e.g., of trying a plurality of sets. Optionally or additionally, this is done by selecting sets of individuals (e.g., based on some shared characteristic, such as profession or place in the network) and seeing the effect of vaccinating these individuals. Optionally or additionally, a different search technique is used, e.g., treating the problem as an optimization problem.

Exemplary Use of the System and Methods for Testing

In some embodiments, the system and methods are used to identify selected subjects to be tested for the disease. In some embodiments, the testing is used to assess one or more of the progress of the disease, the progress of the treatments, the progress of the herd immunity, etc.

Exemplary Use of the System and Methods for Determining Who Will Receive a Certain Type of Vaccination In some embodiments, during the development of vaccines for a certain disease, different vaccines comprising different vaccine potencies are developed. In some embodiments, vaccine potency is a quantitative measure of the specific ability of the vaccine product to achieve an intended biological effect defined in a suitable biological assay based on the attribute of the product that is linked to the relevant biological properties. In some embodiments, the system is used to identify which individuals will receive which types of vaccines in relation to their potency. For example, individuals that received and/or were identified as a high superspreading score by the system would be vaccinated with more potent vaccines, when compared with other individuals having lower superspreading scores. In some embodiments, those individuals having lower superspreading scores might either receive later a vaccination or receive a vaccine having a lower potency.

Exemplary Privacy Settings

In some embodiments, the system comprises one or more layers of protection and/or privacy. In some embodiments, layers of protection include one or more of encryption algorithms and/or software.

For example, encryption algorithms and/or software convert the data into ciphertext to transform the original data to a non-readable format accessible only to authorized parties who can decrypt the data back to a readable format. The process of encrypting and decrypting messages optionally involves keys. The two main types of keys in cryptographic systems are symmetric-key and public-key (also known as asymmetric-key).

Exemplary types of keys: Symmetric-keys: In symmetric-key schemes, the encryption and decryption keys are the same. Communicating parties must have the same key in order to achieve secure communication. Public Keys: In public-key encryption schemes, the encryption key is published for anyone to use and encrypt messages. However, only the receiving party has access to the decryption key that enables messages to be read. In some embodiments, the length of the encryption key used in the system is one or more of 128-bits, 256-bits, 1024-bits and 2048-bits.

In some embodiments, the privacy of the users that information is being collected is protected by anonymizing the user at the source. For example, when a cellular phone/electronic device is used to collect the relevant data, the name of the owner of the electronic device is either encrypted and/or anonymized so any interaction with external sources (for example the servers of the systems) will be managed without the use of the actual name of the user but using an encrypted and/or anonymized user name. In a practical example, electronic devices/cellphones are used to evaluate, quantify and qualify the interactions of the user with other people during the day. In some embodiments, the cellphone communicates with other cellphones to monitor the interactions (distance, location, duration, etc.). In some embodiments, when collecting the data about the interactions, the software in the electronic device will use encrypted and/or anonymized user names. For example, using the names as mentioned in the example below, John Doe, Jane smith and Mark Lite are three users, all having cellphones and optionally comprising a dedicated app for this purpose. In some embodiments, the software of the app in the electronic device will encrypt and/or anonymize the names to be, for example, John Doe=user 265498756124565526, Jane smith=user 31678465923128 and Mark Lite=user 463212887036554. From this point on, all communications between their electronic devices and external sources will be performed using the encrypted and/or anonymized user names. Optionally, for example as described below, the user IDs or what is exchanged between telephones) are non-unique. For example, provided at a ratio of, for example 1:100, 1:1000, 1:10000, 1:100000 between codes and individuals. While this may mean a potential for confusion between individuals, such confusion may be small, while the increase in difficulty of identifying a use based on the tracked information can significantly increase.

Furthermore, when assessing the order of receiving treatment, either individually or by groups, (e.g., at a server) may comprise the parameters needed to enter a certain group (for example, the first group to receive treatment, the second group to receive treatment, etc.). In some embodiments, the action of comparing between the parameters of each group and the collected data from the user will be performed inside and by the electronic device itself, thereby avoiding sending data to the servers. In some embodiments, the electronic device will contact the server to requests the parameters, the electronic device will perform the necessary calculations and will generate a score that will be sent back to the server in an anonymized matter (as explained before). In some embodiments, additional information regarding each individual user, as disclosed above, is also downloaded to the electronic device for use of calculations. Once the calculations are finished, the resulting data will be sent to the servers and, in response, the server will optionally send a notification to the user to go and receive treatment.

It is a particular feature of some embodiments of the invention that information about a person's activities, locations, meetings, are not sent out of the device except as, for example, an overall score or a priority for treatment. In some cases, the behavior is sent out but is anonymized and/or condensed, for example, indicating a number (e.g., optionally not an exact number and/or time and/or date) of people met and a number of large congregations attended (optionally not an exact number and/or location), but with enough details removed so that identification of an identity of the device owner will be difficult or impossible.

In some embodiments, whether the calculations are performed on the servers or on the electronic device, the encryption and/or anonymizing of the name of the user is always used. In some embodiments, the means to read between the encrypted/anonymized user name and the actual name will only be available in the user's electronic device.

In some embodiments, the notification for getting treatment may or may not contain information regarding the results of the calculations. For example, an individual that was identified as a superspreader may or may not receive information about the fact that he/she was identified as such. In some embodiments, the potential advantage of not providing such information is to further enhance the privacy protection of the user. For example, an onlooker may not be able to tell if a user received a high score due to his own behavior, the behavior of those he meets and/or an underlying health condition, which may put them at higher risk.

In some embodiments, dedicated codes, for example in the form of coupons, will be provided to individuals having important/relevant professions (like doctors, police, etc.). In some embodiments, insertion of the codes into their personal electronic devices will inform the system that that encrypted/anonymized user needs a correction in their score. In some embodiments, the correction can be either increasing the score or decreasing the score. In some embodiments, when the electronic device detects certain behavior, like an increase in the movements of the user, the electronic device (for example via the dedicated app) will warn the user that his score will be changed if the behavior is not changed. In some embodiments, changing the score can be either increasing or decreasing the score.

Exemplary Methods for Identifying Superspreaders with High Levels of Anonymization It has been shown that individuals are concerned that the authorities and/or companies are constantly collecting data with or without their consent for a plurality of reasons. It is also scope of some embodiments of the invention to provide a method of identifying superspreaders without the need to collect data that could potentially be used to lead to the identification of the person in question.

As an example, consider three types of systems having different levels of possible anonymization techniques, in accordance with various exemplary embodiments of the invention:

1. A system that uses personal information but does not transmits that personal information about the individual;

2. A system that uses personal information but does not transmits specific information that could be used to potentially identify the individual; and 3. A system that does not require any personal information to work.

In some embodiments, the anonymization techniques described in the "Exemplary Privacy Settings" section belong to the first type and/or the second type of technique, where relevant data (positional data, personal data, etc.) is used by the system but: a) anything that is transmitted is either coded and/or anonymized when used, or b) the necessary calculations are performed on the electronic device itself, thereby avoiding sending any personal data at all.

In the following paragraphs, systems belonging to the third type of system comprising a method of identifying a superspreader that potentially does not require the use of any personal information will be explained.

Exemplary "ID" Based System for the Identification of Superspreaders

In some embodiments, the system is based on the following assumptions: 1) all individuals comprise an electronic device of any kind; 2) on each electronic device there is installed a dedicated application/app that runs the system's software (as will be explained in the following paragraphs); and 3) when individuals meet other individuals, information is passed between their electronic devices.

Referring to FIGS. 5*a-f*, showing flowcharts of exemplary methods of identification of superspreaders, with an anonymization, according to some embodiments of the invention. In some embodiments, the method begins when a user downloads the software, in the form of an application (or app) into their electronic device 502. In some embodiments, dedicated electronic devices comprising the software will be distributed to those individuals who either do not possess an electronic device or do not want the software downloaded into their electronic devices. In some cases, the device has such software preinstalled thereon.

In some embodiments, when the individual opens the application, optionally, the individual will be requested to provide and/or insert an identification (ID), optionally using alphanumeric digits 504, optionally comprising a high number of digits, for example 10 digits, 20 digits, 40 digits. In some embodiments, the system will automatically provide an ID to the device (e.g., will be generated locally, for example, as a random number or as an encrypted version of the user ID. To facilitate the explanations below, a 20 digits ID will be assumed. It should be understood that other length of ID can be used, noting the difference between IDs that are expected unique and IDs that are not expected to be unique and within unique IDs, IDs that also a particular part thereof is long enough to be expected to be unique.

At this point, all users have an electronic device with a software in the form and/or as part of an application in which an ID comprising 20 digits has been assigned to the device. It should be noted that the use of "application", "app" and "software" are interchangeable for the explanation of the following methods. From here, four different methods can be used, as will be further explained bellow.

Anonymized Method 1—Count

Figure 5A:
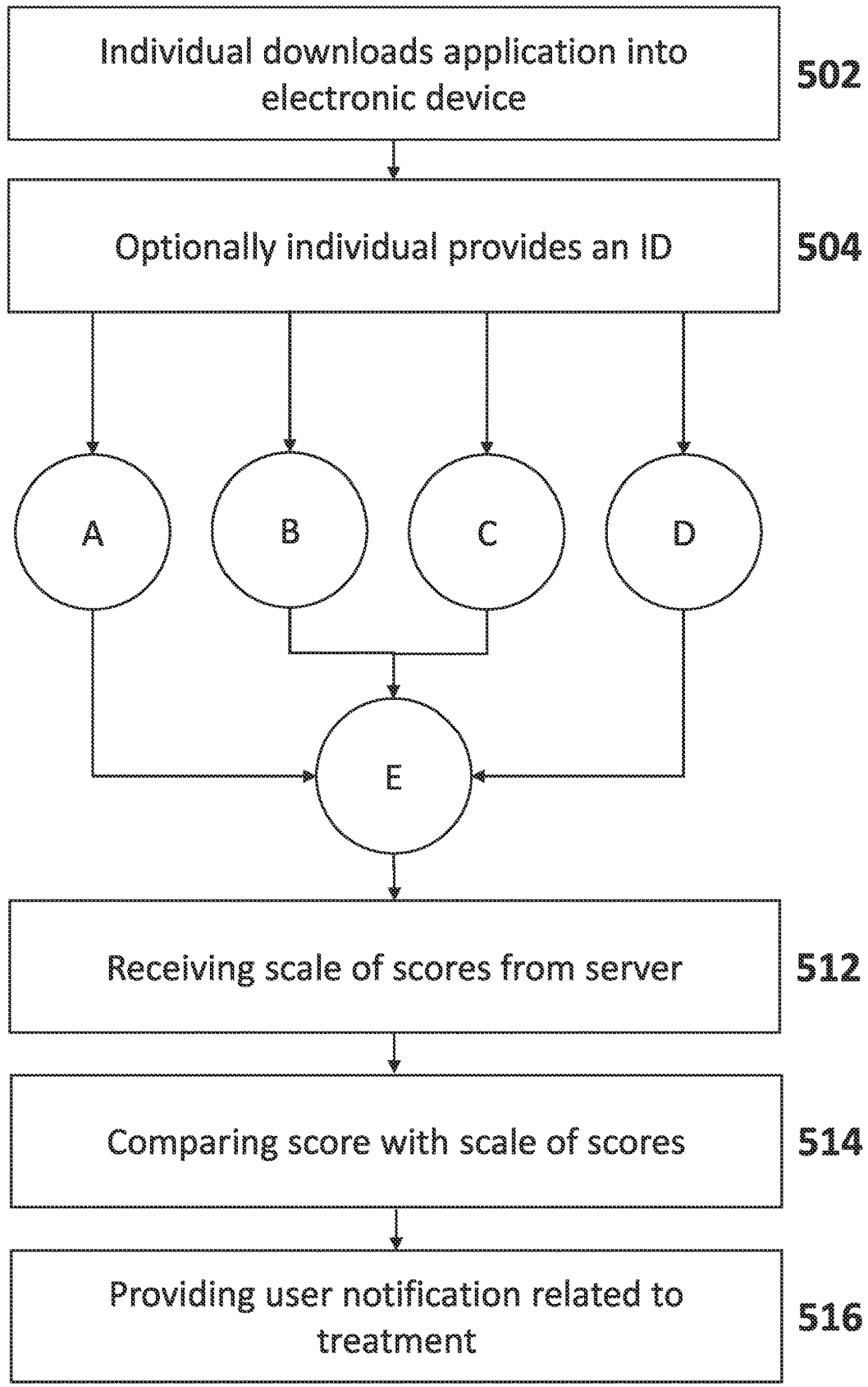
FIGS. 5a-5f are flowcharts of exemplary methods for identifying superspreaders with high levels of anonymization, according to some embodiments of the invention.
Figure 5B:
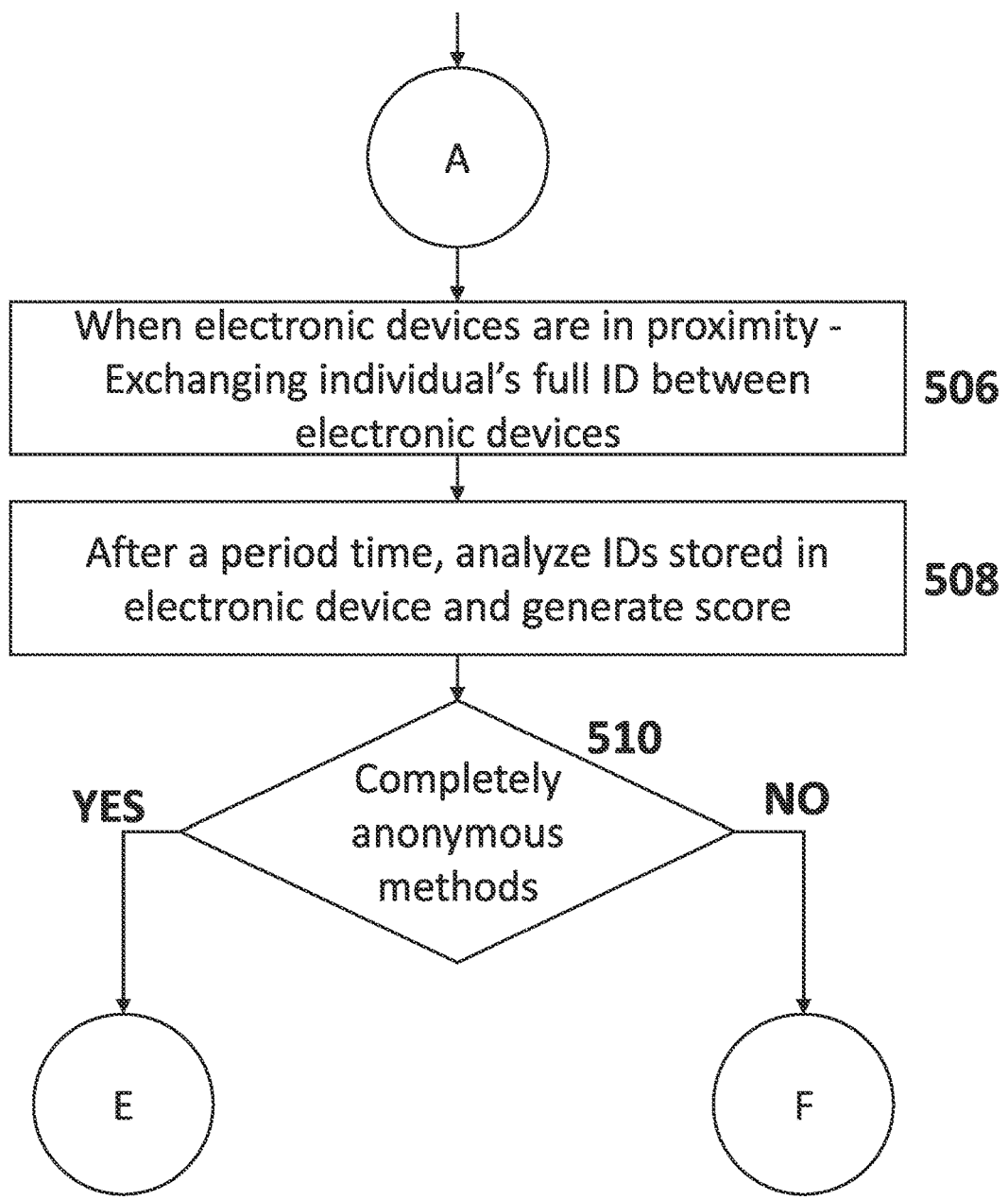

Referring to FIG. 5b, showing a flowchart of exemplary anonymized method 1, according to some embodiments of the invention. Following the letter "A" from FIG. 5a to FIG. 5b, in some embodiments, when an electronic device comes in proximity to another electronic device, the devices exchange full IDs 506 between each other, and the software saves the received ID in the application itself. In some embodiments, after a certain period of time, for example, after one day, after 7 days, after 14 days, after 30 days, or intermediate or shorter times and/or on request by a central server, the application analyzes the IDs stored in the electronic device 508. In some embodiments, analyzing comprises one or more of counting the number of IDs that were received, the number of times that a specific ID was received and the number of IDs received in a day. In some embodiments of the invention, the counting is weighted so different IDs get a different weight, for example, IDs with a high score may be weighted higher, for example as described herein. In particular, IDs that are associated with contacting other suspected superspreaders may receive a higher score. In some embodiments, the software then generates a score based on the result of the analysis.

At this point one of two different methods is optionally applied, a completely anonymous method and a semi-anonymous method 510.

In some embodiments, when the method is a completely anonymous method, the method continues following the letter "E" back to FIG. 5a.

In some embodiments, the application receives from the server a scale of scores 512. For example, continuing using the scale as above, from 1 to 100, group 1 are those individuals having a score higher than 90, group 2 are those individuals having a score from 80 to 90, and so on. In some embodiments, the software then compares the score generated from the analysis with the scale of scores 514. In some embodiments, based on the result of the comparison, the software provides the user of the device with relevant information related the treatment to be received. For example, a predetermined date to receive vaccination (information received with the scale of scores from the server) and/or the group number for receiving the vaccination. In some embodiments of the invention, the scale of scores is generated by the receiving information about the score distribution and selecting cutoff values optionally based on available vaccines. Optionally, the information comprises receiving scores form some or all devices. Optionally, only a statistical same of scores is used, for example, fewer than 10%, 1%, 0.1% of available devices, for example, between 50 and 10,000 scores. It is noted that such scores may be delivered anonymously, for example, using an anonymous web service, optionally anonymized using anonymity tools such as Tor, so that the deliverer of each score is unknown. Optionally, the scores are digitally signed by the sender.

Figure 5C:
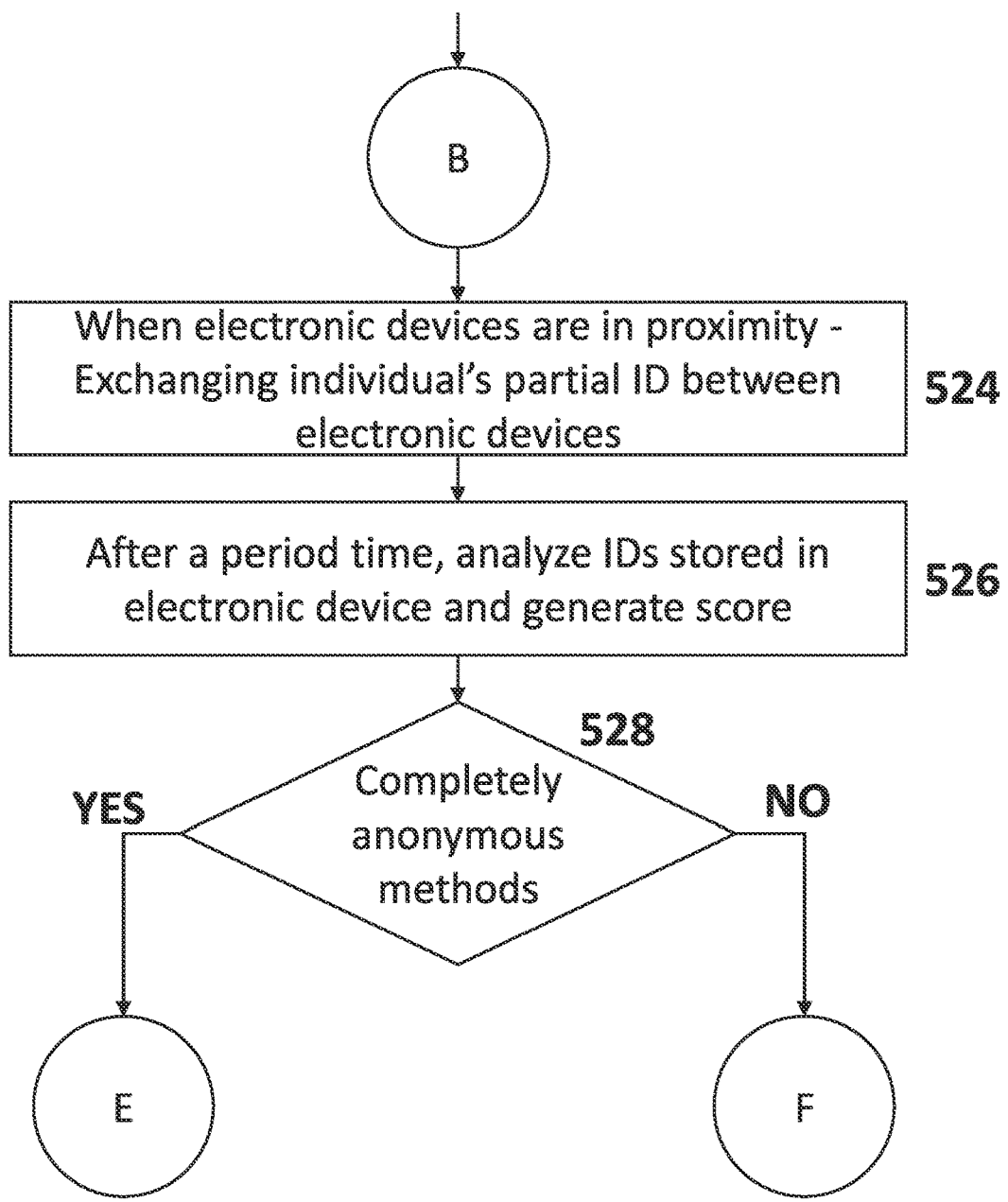
Figure 5D:
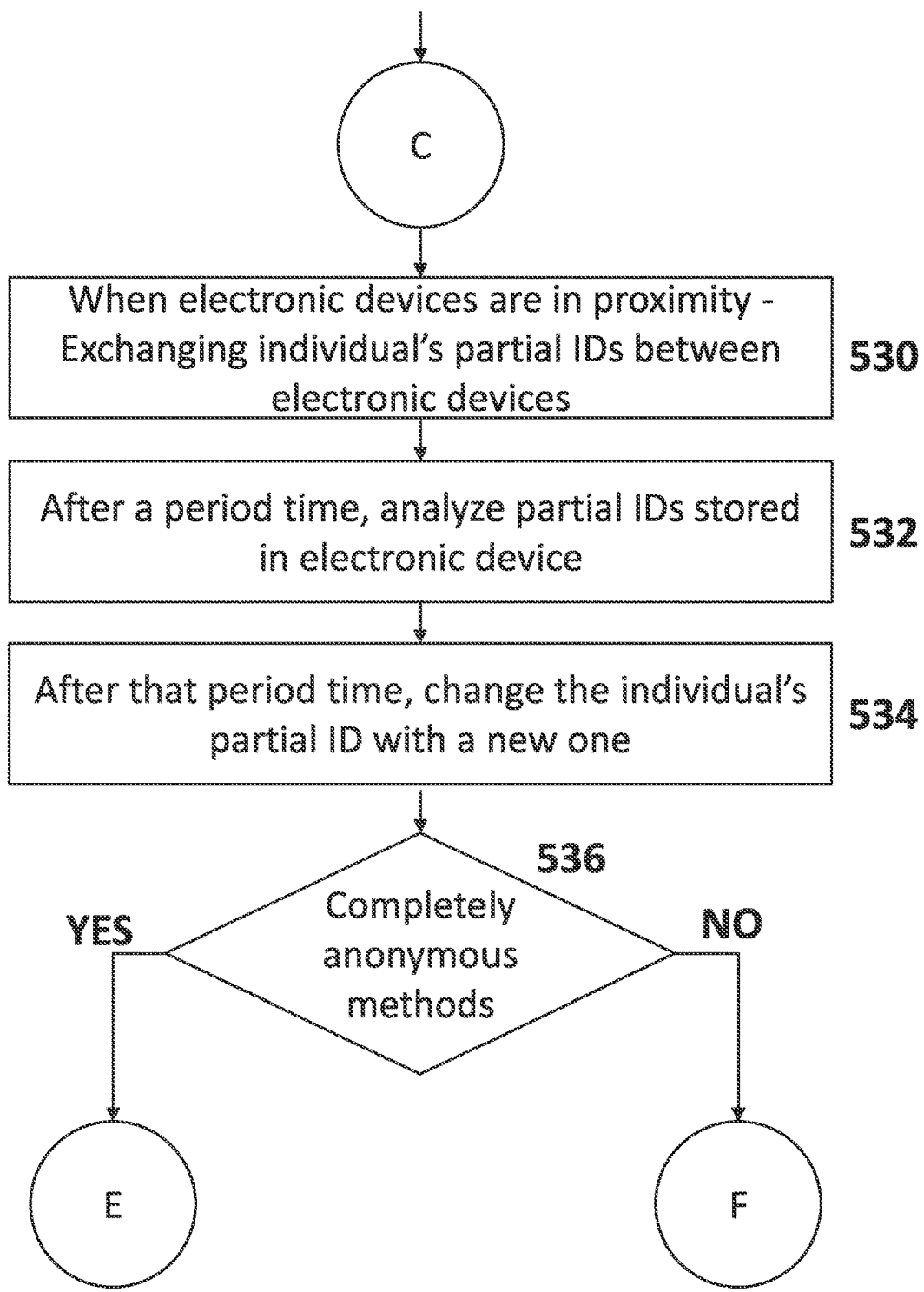
Figure 5E:
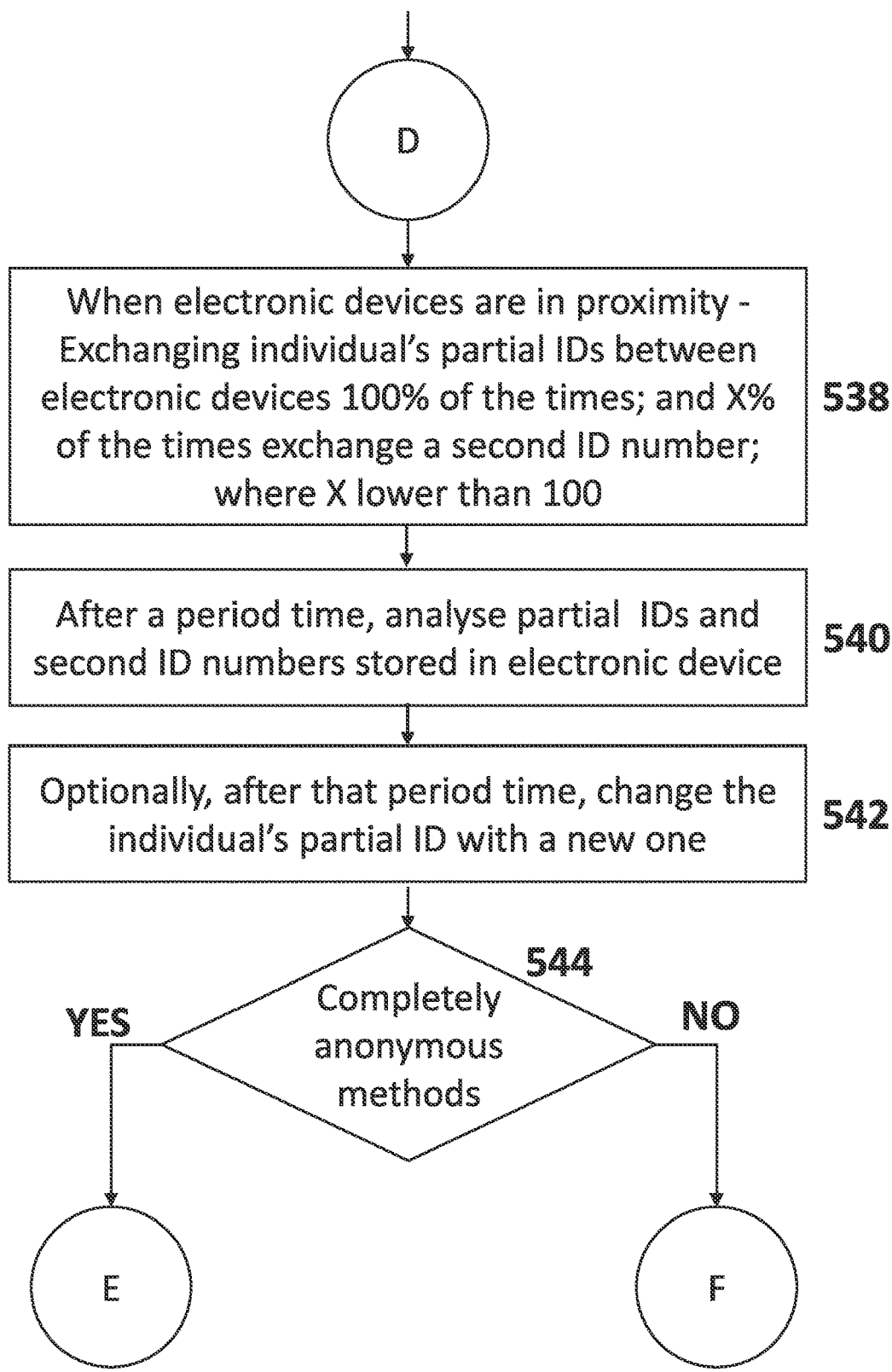
Figure 5F:
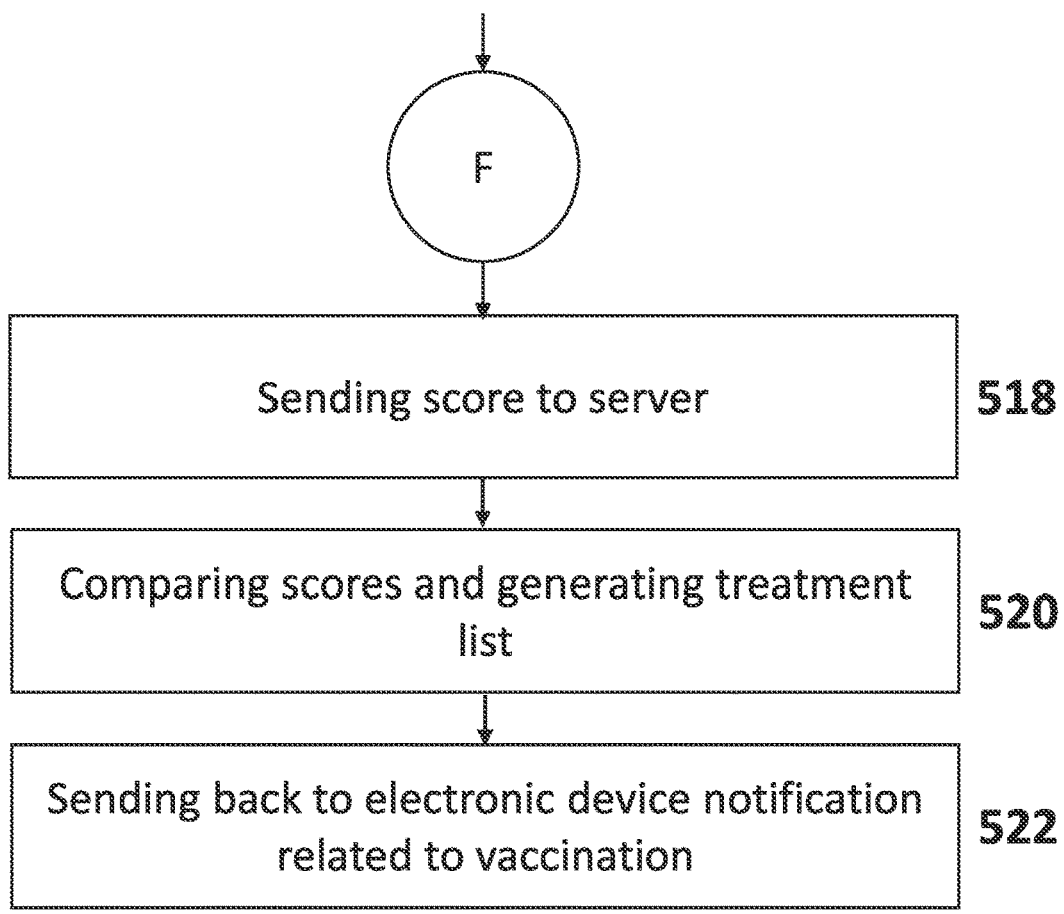

Returning to FIG. 5b, in some embodiments, when the method is not a completely anonymous method, the method continues following the letter "F" to FIG. 5f.

In some embodiments, after the software has generated a score based on the analysis, the software sends the score, together with the full ID (here and in other examples, a full ID may be encrypted or Hashed or otherwise used to generate a token, which, optionally, is not decipherable by the server), to the server to be used to evaluate if that specific individual is potentially a superspreader or not, when compared to other users 518. In some embodiments, the server performs an evaluation by comparing the scores of the different IDs 520 and generates a treatment list according to the result of the evaluation. In some embodiments, the server then sends back notification regarding the vaccination procedures 522, for example, when to go to receive a vaccination, the group number, etc.

In some embodiments, optionally, the user can choose to respond to a series of personal questions presented by the application, which are then translated into factors that affect the score, for example as disclosed herein.

In some embodiments, the user choses the level of anonymity that the system will work (completely anonymous or partially anonymous), e.g., different individuals may have different anonymity levels in a same vaccination prioritization system.

Anonymized Method 2—Count with Transmission of Partial Username

Referring to FIG. 5c, showing a flowchart of exemplary anonymized method 2, according to some embodiments of the invention. Following the letter "B" from FIG. 5a to FIG. 5c, in some embodiments, when an electronic device comes in proximity to another electronic device, the devices exchange partial IDs, for example only the last 10 digits of the 20 digits of the ID 524, and the application saves the received partial ID in the application itself. In some embodiments, the partial ID is a substantially unique partial ID. For example, the use of the last 10 digits of the 20 digits increases the chances that the partial ID is a substantially unique partial ID. In some embodiments, the partial ID is a substantially non-unique partial ID. For example, the use of the last 3 digits of the 20 digits increases the chances that the partial ID is a substantially non-unique partial ID, since there is an increased chance that the same last 3 digits appear in more than one ID. It should be understood that the word "substantially" in this context does not mean to be vague, but it is related to the statistical probabilities that a presented partial ID could be identical to another.

In some embodiments, a potential advantage of exchanging only partial IDs is that it decreases the chances that the specific individual could be identified. It is also noted that, in some embodiments, transmitting partial ID might introduce errors to the analysis of the meeting between individuals since it increases the possibility that one or more individuals will transmit the same partial ID. Since the scope of the method is to protect the privacy of the individuals while contemporarily providing an indication of a potential superspreader, a certain margin of error is acceptable.

In some embodiments, when a received partial ID is stored in the application, it is stored (or only transmitted that way) by adding its own partial ID. In some embodiments, a potential advantage of using this method is that if such pairs of partial ids are transmitted to a third party, such third party can track and count unique meetings.

In some embodiments, after a certain period of time, for example, after 7 days, after 14 days, after 30 days (or other times for as discussed in the previous method), the application analyzes the partial IDs stored in the electronic device 524. In some embodiments, analyzing comprises one or more of counting the number of partial IDs that were received, the number of times that a specific partial ID was received and the number of partial IDs received in a day. In some embodiments, the software then generates a score based on the result of the analysis. In some embodiments of the invention, a repeat meeting with a same partial ID is not counted or given a lower weight. Other methods of counting as described herein may be used. In some embodiments of the invention, the count is otherwise normalized. For example, the distribution of counts may be used to reconstruct an estimate of actual diversity of meetings, using statistical methods of distribution estimation, such as known in the art. Such methods may also be used if instead of always transmitting the ID the ID is only sometimes transmitted. This statistical distribution may be used to estimate the percentage of unique meetings vs percentage of repeat meetings, for example, assuming a given distribution shape for repeat meetings. Such a given shape may be provided, for example, by a central server (e.g., based on real-time data collection) or a priori. Optionally or additionally, such distribution may be created by sometimes applying method 1 of full ID transmission.

At this point, one of two different methods is optionally applied, a completely anonymous method and a semi-anonymous method 528. In some embodiments, when the method is a completely anonymous method, the method continues following the letter "E" back to FIG. 5a.

In some embodiments, when the method is not a completely anonymous method, the method continues following the letter "F" to FIG. 5f. These alternatives may be applied as above.

Anonymized Method 3—Count with Transmission of Partial Username and Username Changes Periodically In this method, which can be used as a variant of the last two methods, and is shown in FIG. 5d, the ID or partial ID used by the device is modified.

In some embodiments, for example, after the certain period of time mentioned above for counting, the partial ID that is used for the transmission of IDs between is changed by the system and/or the individual itself 534. The actual ID may be changed or a different part of the ID transmitted. In some embodiments of the invention, the original ID is used as a seed to generate a series of pseudo random IDs to be used for transmission. In some embodiments, for example, when the system changes the transmitted partial ID, the system transmits instead of the last 10 digits of the ID, the first 10 digits of the ID; or for example the first 5 digits together with the last 5 digits. It should be understood that the above-mentioned are only examples, and that other methods of randomizing the partial ID that is transmitted are also included in the scope of some embodiments of the invention. In some embodiments, periodically changing the partial ID may further cause to errors since it further increases the possibility that one or more individuals will transmit the same partial ID. As mentioned above, a further certain margin of error is still acceptable.

The method then continues with various options for acting on the score, for example, a completely anonymous method and a semi-anonymous method 536. In some embodiments, when the method is a completely anonymous method, the method continues following the letter "E" back to FIG. 5a.

In some embodiments, when the method is not a completely anonymous method, the method continues following the letter "F" to FIG. 5f.

In this and other embodiments it is noted that other follow up activities may be provided in addition or instead, in particular, activity by a central server may be reduced. For example, a user may simply go to a vaccinating station and show their score and be given a vaccination or date therefore accordingly.

Anonymized Method 4—Complex Count with Transmission of Partial Username, at Least One Additional Number and Optionally Username Changes Periodically Referring to FIG. 5e, showing a flowchart of exemplary anonymized method 4, according to some embodiments of the invention. In some embodiments, a complex count method is used for probabilistically determining if a certain individual is a potential superspreader. In some embodiments, the complex count method comprises the use of two independent counts for the determination.

Following the letter "D" from FIG. 5a to FIG. 5e, in some embodiments, when an electronic device is in proximity to another electronic device, the system is configured to exchange not one, but at least two ID numbers as following.

In some embodiments, the first number to be exchanged is the partial ID 538. In some embodiments, the exchange of the first number is as disclosed in method 1, where the full ID is exchanged. In some embodiments, the exchange of the first number is as disclosed in either method 2 or method 3, where a partial ID is exchanged. For the explanation of the method and as disclosed in FIG. 5e, the explanation will refer to the transmission of a partial ID. It should be understood that this method could also be applied when transmitting the full ID.

In some embodiments, the first number is used to evaluate the number of contacts.

In some embodiments, the second number to be exchanged is a different set of digits, either created by the system or inserted by the user itself 538. In some embodiments, the actual second number to be exchanged is a partial second number, similar to what is done with the first number.

In some embodiments, the second number is used to evaluate if the individual is meeting people from outside a limited subpopulation and/or track the general promiscuousness (optionally in a non-sexual sense) of such individuals.

In some embodiments, contrary to the first number that always is exchanged in an encounter, the second number is exchanged at a certain "rate of probability". In some embodiments, a rate of probability is, for example, a calculated number that responds to the question: what is the percentage rate necessary to separate between a superspreader and a non-superspreader. In some embodiments, the rate of probability is achieved by running a simulation, and checking for different probability rates the degree of discrimination. For example, a rate of probability can be 3%, 5%, 10%, 20% or smaller or intermediate values. In some embodiments, this means that, if the rate of probability is 3% for example, an electronic device that encounters 100 electronic devices will exchange 100 times (100% of the times) the first number and 3 times (3% of the times), in addition to the first number, will also exchange the second number. In some embodiments, the rate of probability is lower than 100.

In some embodiments, from the moment the system is activated, the electronic devices of the individuals will begin collecting first and second numbers as long as they continue to meet other electronic devices.

In some embodiments, when a certain electronic device exchanges the second number (under the rate of probability), the electronic device will exchange in addition to its second number, all second numbers that were collected until that moment. In some embodiments, potentially and probabilistically, an individual that is a superspreader will collect a high number of second numbers because he/she meets many different individuals, who themselves meet different individuals. While an individual "trapped" in a subpopulation may only collect at most as many numbers are there are persons in the subpopulation. Therefore, in some embodiments, when someone meets that superspreader, many second numbers will be potentially exchanged from that superspreader to that someone. In some embodiments, those second numbers collected from other individuals will later be used to indicate a specific meeting between an individual and a superspreader.

In some embodiments, an individual that collects many second numbers, potentially and probabilistically, met a superspreader and/or is one themselves. In some embodiments, this information is used to cause an effect (e.g., increase) in the scoring of the individual and/or in the weight of the contact.

The collected IDs may be counted after a time, e.g., as described in the other methods (540) In some embodiments, optionally, after the certain period of time mentioned above, the partial ID transmitted between devices is changed by the system and/or the individual itself 542 as disclosed above.

Optionally, a method of follow-up is selected, for example, a completely anonymous method and a semi-anonymous method 544. In some embodiments, when the method is a completely anonymous method, the method continues following the letter "E" back to FIG. 5a.

In some embodiments, when the method is not a completely anonymous method, the method continues following the letter "F" to FIG. 5f, for example as described above.

In any of the above methods, optionally, statistical information about collected first and/or second numbers (e.g., how many people had how many collected first and/or second numbers) may be transmitted to the server to help generate a better picture of these statistics of the population's collected information.

In some embodiments of the invention, more than one second number is used. Optionally, each additional such number is transmitted at a different probability. This allows different numbers to give information about different characteristics of subpopulations. It is noted that if only one number is used and its transmission rate not selected correctly, it may result is propagation of such second number over a significant part of the network of contacts, making it less useful for identifying more closed and more open parts of the network.

In some embodiments of the invention, no additional second number is used. Rather the first number is optionally counted and/or transmitted using such probabilistic transmission rate. So, for example, during a contact, the second device will store the received ID of the first contact in a memory for storing and/or counting contacts with a first ID and also, with some probability store that number in a second memory used for counting and/or tracking second numbers. Additional memories may be provided if more numbers are tracked.

In some embodiments of the invention, a relatively small non-unique ID is used and this ID may be used as an index for the first and/or second memory. For example, when meeting an individual who passes a non-unique ID 234, memory location 234 is increment (optionally in a weighted manner). If a second ID list, say (123, 456, 789) is passed, the count in each of those indexes in the second memory is incremented (optionally in a weighted manner). In some embodiments, only one bit (or an equivalent thereof) is saved for each ID in the second memory and it is either set or unset. Optionally, the second ID uses more bits than the first ID, for example, 2, 3, 4, 5 times as many bits or an intermediate of smaller or greater number. This may allow preventing saturation of second ID tracking. Optionally or additionally, a statistical estimation of the actual number of second IDs is reconstructed using statistical methods and the number of second IDs received and optionally a count of at least a sample thereof. Optionally, an assumption is made about the expected shape of distribution of second IDs.

Optionally or additionally, the number of second IDs collected is tracked as a function of time. Optionally, potential superspreaders (and which get an increased score and/or contact weight) are those who early on accumulate a larger number of second IDs (e.g., as compared to other persons an individual comes in contact with) and/or those persons (e.g., with repeated contact) whose second ID count asymptotes later or not at all.

Regarding repeat meetings with an individual, it is noted that an individual is a sum of all his contacts, so that after a time, if and as that individual meets new contacts, the individual changes and should be weighted more heavily. Such tracking can be by time and/or can be by change in count of first and/or second IDs that an individual has, which count (and/or a date of contact) is optionally transmitted upon meeting and may be stored.

Exemplary Effect of Meeting an Individual that has Met Potential Superspreaders

Figure 6:
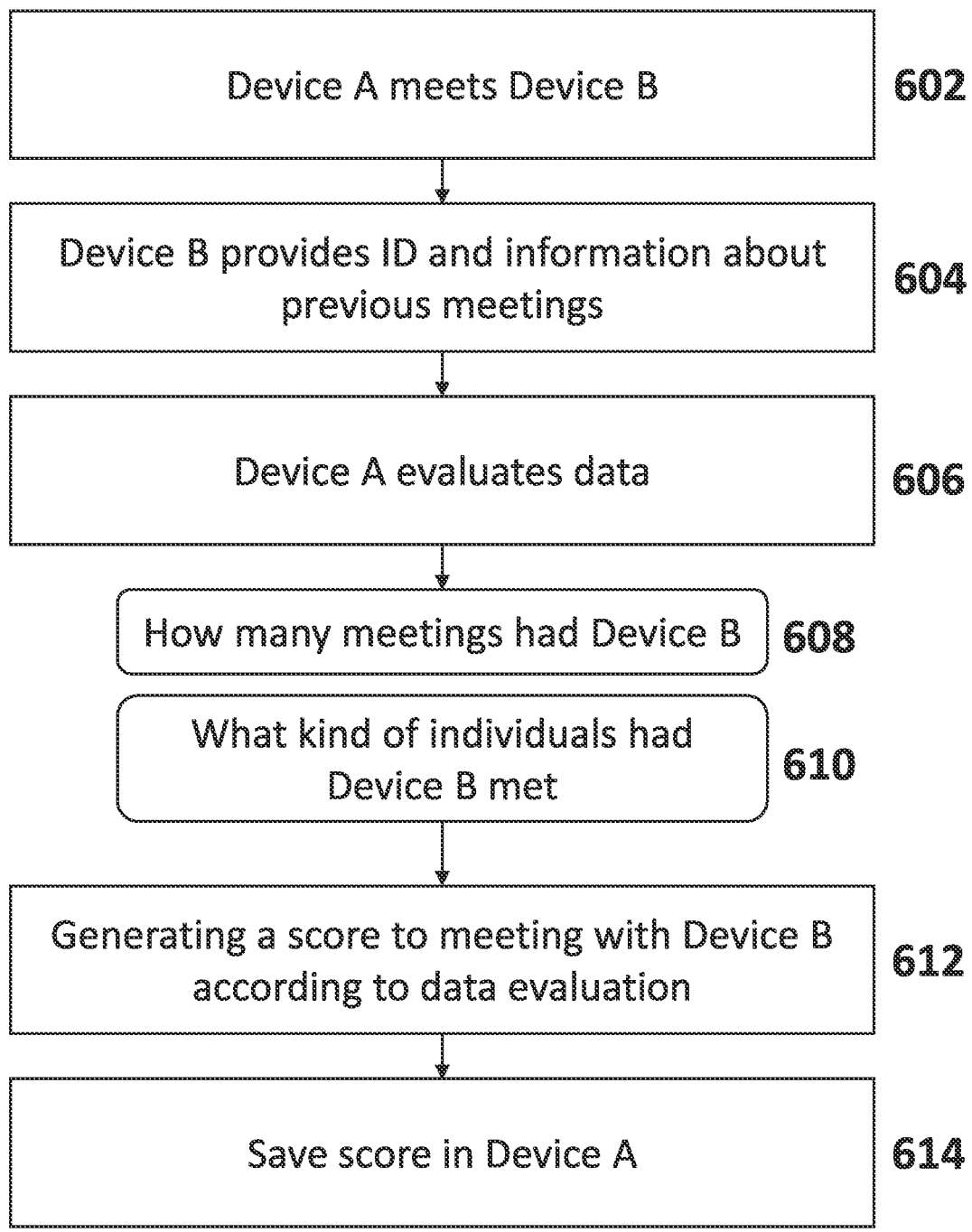
FIG. 6 is a flowchart of a method of generating a score, according to some embodiments of the invention.

Referring now to FIG. 6, showing a schematic flowchart of an example of the effect caused when a certain individual meets another individual that had been in contact with possible superspreaders, according to some embodiments of the invention. In some embodiments, as previously mentioned, when a Device A meets Device B 602, IDs are exchanged and optionally also information regarding previous meetings 604. In some embodiments, for example, the software in Device A, that has just received the ID and previous meetings of Device B, will evaluate the received data 606. In some embodiments, evaluation of data comprises one or more of evaluating the number of meetings Device B has had 608 and the kind of individuals were met during those meetings 610. In some embodiments, since these operations were also previously performed by Device B during its meetings, the information about the possible meeting with a potential superspreader will be also delivered by Device B to Device A, when information is exchanged. In some embodiments, the software in Device A will generate a score to the meeting between Device A and Device B, also in view of the information regarding the kind of individuals that Device B has met 612. In some embodiments, the score is then saved in Device A 614 to be used in the final score calculations, as previously described.

Exemplary Methods

In some embodiments, an exemplary method of providing the order of treatments to a population comprises:
1. Collecting relevant data regarding each individual in the population, according to predetermined parameters.
2. Providing a superspreading score to each of the individuals according to a formula using the predetermined parameters.
3. Ordering each individual according to his or her superspreading score from high to low.
4. Optionally dividing all individuals in groups according to their superspreading score.

In some embodiments, after the list is ready, optionally in groups:
5. Notifying the individuals with a location and a time to receive the treatments.
6. Treating the population according to their superspreading score, optionally by groups, where individuals and/or groups hiving the higher scores will receive first the treatments. In some embodiments of the invention, treatment is rather testing, as testing superspreaders may be a faster and more effective way of detecting a resurging pandemic.

Exemplary System

In some embodiments, the system comprises a computer network architecture optionally with machine learning and/ or other artificial intelligence tools to allow for the automated prioritization of treatments in a pandemic event. In some embodiments, the system allows for prioritization of treatments using information regarding subjects in a population, disease process and progression, number of available treatment doses, and a plurality physical location attributes. In some embodiments, this potentially enables relevant authorities to measure, predict and/or improve their health-related performance during a pandemic. In some embodiments, this in turn enables relevant decision-making personnel and healthcare providers to get a true quantitative sense of what is possible to achieve with any given population of patients, in view of the parameters that define each individual and the population.

The following is an example of the workflow of a user experience with a system of the present invention:

1. A user makes a request for an analysis and list generation report to the system.
2. The system uses an analytics module (A.M.) to analyze the information of the population (for example, information as disclosed above).
3. The system automatically issues a request to a Database Module (DB.M) to provide all relevant information and/or issues a request to external sources (see above) to provide the required information and/or issues a request to a simulations module (S.M) to perform the necessary simulations.
4. The analytics module (A.M.) collates the results into a unified analysis response, based on any combination of the subjects in the population and factors and/or components data available. In some embodiments of the invention, the A.M includes a ML module (optionally in the form of an analytic system or a neural network) which is used to predict transmission and super-spreader potential of an individual based on their past behavior. Optionally, an initial model is provided for such mapping. Optionally, the ML module also receives actual infection information, for example, by automated collection from medical records or from epidemiological studies (e.g., of some or all infected people) and uses this information to update the model, for example, using a machine learning method as known in the art, to generate a prediction of infectiveness (and/or superspreader potential) of an individual given his contacts and the superspreader potential of similar individuals. In some embodiments of the invention, statistical methods are used instead of or in addition to ML methods. Optionally or additionally, what is created is a classifier, which classifies an individual as a potential superspreader. Such a classifier can build a classification scheme given a set of individuals, each with behaviors and actual infectiveness as determined, for example, using epidemiological studies and/or contact tracking combined with disease detection in such tracked contacts. Such classifier may be used (or transmitted to individual devices to be used instead of and/or in addition to counting for example as described herein) to generate a general score for an individual based on the classification and optionally based on additional information, such as medical risk.

Optionally or additionally, the AM includes one or more optimization tools which given the various inputs described herein and/or one or more goals, optimizes vaccine delivery and/or schedule to achieve a better approach to the goal.

5. The analytics module (A.M.) serves the response back to the system, and transmits the list to the user, and the list is now available to the relevant personnel. In some embodiments, this potentially helps the relevant personnel to decide whom, when and where distribute the available doses to the population.

Each and any of such modules may be implemented, for example, using a central server, a distributed server and/or a cloud implementation.

In some embodiments, the system may automatically use the simulation models to select and apply a predictive model for the preferred deployment of the doses (for example, the parameter may be number of available doses or the higher number of individuals protected by the act of vaccination and/or a total number of expected of deaths and/or time to reach a threshold where one or more limitations on society may be removed). In some embodiments, the system may then predict the performance of an underperforming vaccination result (if no changes are made to trend performance) and predict the performance of the same treatment result if the requirements are met, and then compare the before and after predicted performance to show the impact of meeting the requirements. A report of the requirements and of the predicted impacts of meeting the requirements may then be prepared by the system, and transmitted to the user.

Figure 7:
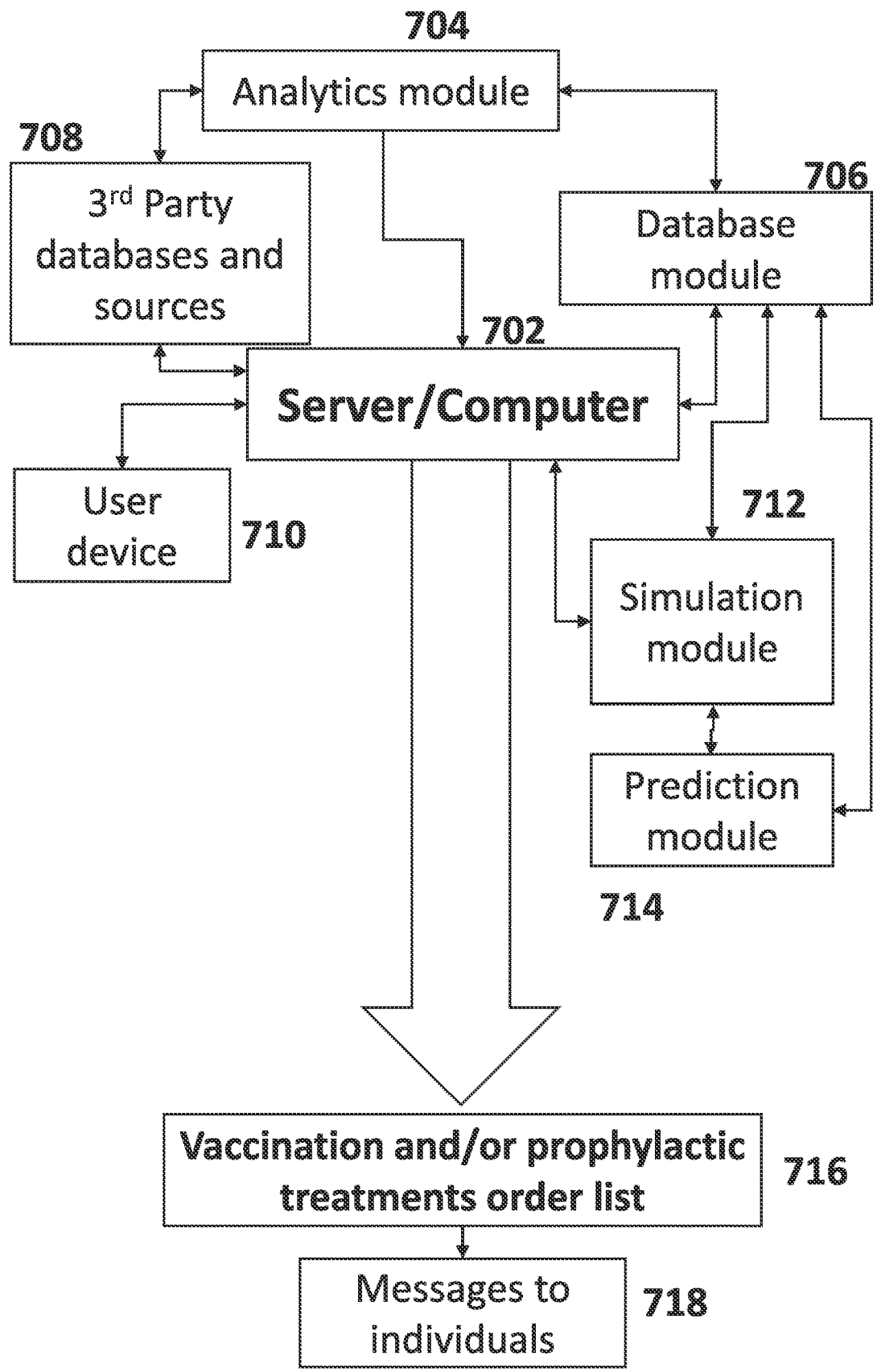
FIG. 7 is a schematic representation of an exemplary system, according to some embodiments of the invention.

FIG. 7 schematically illustrates components of an exemplary system comprising a computer network architecture usable in some embodiments of the invention, comprising at least one optional server 702, an optional analytics module (A.M.) 704, an optional Database Module (DB.M) 706, and/or optional access to various third-party databases and sources 708, and an optional simulations module 712.

In some embodiments, a user using a user device 710 accesses the at least one server 702. In some embodiments, the user transmits a user request to the analytics module (A.M.) 704 for analysis of data and the generation of a list 716. In some embodiments, analytics module (A.M.) 704 accesses the Database Module (DB.M) 706 either directly and/or via the server 702. In some embodiments, the analytics module (A.M.) 704 accesses through various identified third party and sources 708. In some embodiments, data accessed from third-party databases and sources 708 may be analyzed and stored in Database Module (DB.M) 706, thus supporting the simulations module 712, which performs machine-learning prediction activities. In some embodiments, the analytics module (A.M.) 704 may also access data received from the simulations module 712 and previously stored in the Database Module (DB.M) 706, thus benefiting from the machine learning and artificial intelligence of the simulations module 712.

In some embodiments, the system optionally comprises a prediction module 714 with a prediction generator and in communication with the simulation module 712 and with the database module 706.

Not shown is a vaccination management server, which is optionally a separate component of the system or be a separate system. In some embodiments of the invention, this server is used to manage distribution of vaccinations (e.g., locations and/or times) and/or tracking of subjects that requested vaccination and/or received such vaccination. Optionally, this server manages the logistics of vaccine distribution using the information form the system indicating which subjects are to be vaccinated and in what order. In some embodiments of the invention, vaccinations are distributed based on population density and the vaccination management server is used to track subjects receiving vaccinations to ensure that they are not vaccinated out of turn, for example, by comparing prioritization data provided by the devices against a record of prioritization intentions.

In some embodiments, the system allows automatic machine learning as new data sources are added, and new data is collected, and the predictive algorithms are recalibrated and reselected using the expanded, and hence more reliable, data. In some embodiments, this may potentially enable users of the system to quickly realize the value of new data.

In some embodiments, the system utilizes machine learning, optionally incorporated in predictive model algorithms to execute predictive analytical operations. Learning may be supervised or unsupervised. In general, a predictive model analyzes historical data to identify patterns in the data. The patterns identified may include relationships between various events, characteristics, or other attributes of the data being analyzed. Modeling of such patterns may provide a predictive model whereby predictions may be made. Development of predictive models may employ mathematical or statistical modeling techniques such as curve fitting, smoothing, and regression analysis to fit or train the data. Such techniques may be used to model the distribution and relationships of the variables, e.g., how one or more events, characteristics, or circumstances (which may be referred to as "independent variables" or "predictor variables") relate to an event or outcome (which may be referred to as a "dependent variable" or "response").

In some embodiments, a machine learning process may include developing a predictive model. For example, a dataset comprising observed data may be input into a modeling process for mapping of the variables within the data. The mapped data may be used to develop a predictive model. The machine learning process may also include utilizing the predictive model to make predictions regarding a specified outcome that is a dependent variable with respect to the predictive model. The machine may then be provided an input of one or more observed predictor variables upon which the output or response is requested. By executing the machine-learning algorithm utilizing the input, the requested response may be generated and outputted. Thus, based on the presence or occurrence of a known predictor variable, the machine-learning algorithm may be used to predict a related future event or the probability of the future event.

It is noted that a most basic prediction may be used, e.g., behavior in past predicts behavior in future. For example, if a person regularly meets 30 people a day for over 15 minutes each and within 2 meters and I a location that is closed (e.g., based on mapping data sources), it is assumed that may continue. Similarly, if a person attends a church of 200 people once a week, that may be assumed to continue. In addition, class behavior may be applied. For example, if the person is collage age, the system may be programmed with an expectation of a certain number and/or expected dates and/or expected probability of parties such a person might attend. Such information may also be generate by statistically analyzing the behavior of others in that person' cohort.

In some embodiments, once the treatment order list 716 is ready, individual messages 718 are sent to the specific individuals notifying them where and when they should go to be treated.

The architecture of the system may depend on the implementation. For example, if the system is mainly anonymous, with scorings being generated on individual cellphones (or other devices), the server may be used to generate information to be used by the cellphones and/or to collate results generate vaccination prioritization plans and/or invite individuals to be vaccinated.

In such an example, the software of the electronic device may increase in relative importance. Such device may include a memory (e.g., as noted herein) for storing actual IDs or partial IDs and/or counts thereof. Optionally or additionally, such device includes an ID generator. Optionally or additionally, such device includes communication software (e.g., addresses) for making an anonymous drop of information and/or for receiving a general broadcast of information (e.g., from the server) and/or for accessing an individual's EMR or other repository with relevant medical information. Optionally or additionally, such a device includes a count analysis and/or other module that applies a classification or scoring method for example, as described herein. Optionally or additionally, such a device includes a sensor an associated software for detecting infection related information, for example, being indoors, location, distance from other electronic devices, duration at such distance, coughing sounds and/or video or still analysis to detect mask wearing. Optionally or additionally, such a device includes a display and associated software for showing a vaccination invitation and/or a score. Optionally or additionally, such a device includes an input (e.g., a camera) for receiving information form printed or other screens, for example, a user's occupation or special dispensation. Optionally or additionally, such device includes software, which generates behavior alerts to the user, for example, when the user engages in riskier behavior.

Various embodiments and aspects of the present invention as delineated hereinabove and as claimed in the claims section below find calculated support in the following examples.

Example

Reference is now made to the following prophetic examples, which together with the above descriptions illustrate some embodiments of the invention in a non limiting fashion.

In the following example, three imaginary individuals (John Doe, Jane Smith and Mark Lite) will be scored according to one or more exemplary factors and/or components, as disclosed above. It should be understood that the following scenario is not limiting and it is only provided to enable a person having skills in the art to implement the invention.

Background Information

|  | John Doe | Jane Smith | Mark Lite |
| --- | --- | --- | --- |
| Age (relative weight 1%) | 30 | 35 | 33 |
| Profession (relative weight 5%) | Teacher | Operator | Unemployed |
| Known health conditions (relative weight 4%) | None | Chronic coughing | None |
| Visits religious gathering (relative weight 20%) | No | Yes | Yes |

Weekly Mobility Data

|  | John Doe | Jane Smith | Mark Lite |
|---|---|---|---|
| Day 1 | Total locations visited: 5<br>Estimated potential number of individuals in contact with subject on this day: 650 | Total locations visited: 3<br>Estimated potential number of individuals in contact with subject on this day: 150 | Total locations visited: 1<br>Estimated potential number of individuals in contact with subject on this day: 5 |
| Day 2 | Total locations visited: 6<br>Estimated potential number of individuals in contact with subject on this day: 750 | Total locations visited: 4<br>Estimated potential number of individuals in contact with subject on this day: 250 | Total locations visited: 1<br>Estimated potential number of individuals in contact with subject on this day: 5 |
| Day 3 | Total locations visited: 5<br>Estimated potential number of individuals in contact with subject on this day: 650 | Total locations visited: 2<br>Estimated potential number of individuals in contact with subject on this day: 80 | Total locations visited: 2<br>Estimated potential number of individuals in contact with subject on this day: 30 |
| Day 4 | Total locations visited: 5<br>Estimated potential number of individuals in contact with subject on this day: 650 | Total locations visited: 2<br>Estimated potential number of individuals in contact with subject on this day: 80 | Total locations visited: 1<br>Estimated potential number of individuals in contact with subject on this day: 5 |
| Day 5 | Total locations visited: 5<br>Estimated potential number of individuals in contact with subject on this day: 650 | Total locations visited: 3<br>Estimated potential number of individuals in contact with subject on this day: 150 | Total locations visited: 2<br>Estimated potential number of individuals in contact with subject on this day: 30 |
| Day 6 | Total locations visited: 5<br>Estimated potential number of individuals in contact with subject on this day: 650 | Total locations visited: 1<br>Estimated potential number of individuals in contact with subject on this day: 5 | Total locations visited: 1<br>Estimate potential number of individuals in contact with subject on this day: 5 |
| Day 7 | Total locations visited: 5<br>Estimated potential number of individuals in contact with subject on this day: 650 | Total locations visited: 2 (*visited Church)<br>Estimated potential number of individuals in contact with subject on this day: 500 | Total locations visited: 3 (*visited stadium)<br>Estimated potential number of individuals in contact with subject on this day: 500 |
| Score (relative weight 70%) | 80 | 60 | 15 |

In view of the results of the Weekly mobility data alone, the order of the treatments will be John Doe, Jane Smith and then Mark Lite.

The calculation of the overall score is:

| criteria |  | John Doe | Jane Smith | Mark Lite |
|---|---|---|---|---|
| Age | 1% | 50 | 50 | 50 |
| Profession | 5% | 80 | 50 | 0 |
| Known health conditions | 4% | 0 | 90 | 0 |
| Visits religious gathering | 20% | 0 | 80 | 80 |
| Mobility data | 70% | 80 | 60 | 15 |
| weighted scores | 100% | 60.5 | 66.2 | 14.2 |

As can be seen, when taking under consideration all the information data, the order of the treatments will be Jane Smith, John Doe and then Mark Lite.

It should be understood that the above numeric examples are just examples to help a person having skills in the art to understand the invention. It also should be understood that different weight values, scores and methods of calculating a score could be used.

It is expected that during the life of a patent maturing from this application many relevant parameters of scoring activity of individuals and methods of measuring said parameters will be developed; the scope of the invention herein is intended to include all such new technologies a priori.

As used herein with reference to quantity or value, the term "about" means "within ±20% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of prophylactically treating a population having a plurality of subjects with a prophylactic treatment against an epidemic infectious disease, said plurality of subjects each using a smart electronic device, the method comprising:
   a. determining a score for each said plurality of subjects based on behavior data collected using said smart electronic device, said behavior data representing behavior of a subject which increases risk of transmitting said epidemic infectious disease to others, if said subject is infected;
   b. generating for each said plurality of subjects a prioritization of the prophylactic treatment based on said score, said prioritization being higher with increasing risk of spreading said epidemic infectious disease; and
   c. prophylactically treating particular subjects of said plurality of subjects according to said prioritization.

2. The method according to claim 1, wherein said prophylactically treating comprises prophylactically vaccinating; whereas prophylactic treatment comprises prophylactic vaccine.

3. The method according to claim 1, further comprising:
   a. identifying that said smart electronic device is in a closed space;
   b. determining a score for propensity of each said plurality of subjects to be in a closed space with other subjects based on data collected using said smart electronic device;
   wherein higher scores for propensity of each said plurality of subjects to be in a closed space with other subjects increases said prioritization of the prophylactic treatment.

4. The method according to claim 1, further comprising generating, by circuitry, for each said plurality of subjects a predicted likelihood of transmitting said epidemic infectious disease, if itself would have been infected, based on said data collected using said smart electronic device.

5. The method according to claim 1, further comprising receiving a primary prioritization of treatment score of each said plurality of subjects; and updating for each said plurality of subjects said prioritization of treatment based on said primary prioritization of treatment score and said score.

6. The method according to claim 1, wherein said score depends on an estimation of propensity of proximity of said smart electronic device to one or more other smart electronic devices.

7. The method according to claim 1, wherein said generating for each said plurality of subjects a prioritization of the treatment comprises transmitting said score to a server and generating said prioritization on said server.

8. The method according to claim 1, wherein said generating said prioritization comprises comparing scores by different ones of said electronic devices.

9. The method according to claim 1, wherein said generating for each said plurality of subjects a prioritization of vaccination comprises generating said prioritization on said particular electronic device.

10. The method according to claim 1, wherein said generating said prioritization comprises receiving from a server a list or a function indication prioritization according to score.

11. The method according to claim 1, comprising displaying prophylactically treating instructions on said particular electronic device based on said generated prioritization.

12. The method according to claim 1, wherein said generated score is not transmitted outside said smart electronic device.

13. The method according to claim 1, further comprising updating for each said plurality of subjects said prioritization of treatment based on at least one additional parameter.

14. The method according to claim 13, wherein said at least one parameter is historical geolocation data of a certain subject.

15. The method according to claim 13, wherein said at least one parameter is actual medical data of a certain subject.

16. The method according to claim 13, wherein said at least one parameter is profession in record of a certain subject.

17. The method according to claim 13, wherein said at least one parameter is a nature of location of meetings between subjects.

18. The method according to claim 13, wherein said at least one parameter is one or more of:
   a. characteristics of population of subjects potentially to meet with a certain subject;
   b. characteristics of population of subjects that actually met with a certain subject;
   c. a nature of locations usually visited by a certain subject;
   d. a length of time at locations visited by a certain subject;
   e. historical medical data of a certain subject;
   f. third party information received regarding a certain subject.

19. The method according to claim 1, wherein previous data collected using said smart electronic device is used to predict potential future behavior of a certain subject.

20. A system for selecting subjects for prophylactically treating against an epidemic infectious disease a population having a plurality of said subjects, comprising:
   a. a plurality of smart electronic devices configured to be carried around by said subjects and configured with instructions to:
      i. determining a score for each said plurality of subjects based on behavior data collected using said smart electronic device, said behavior data representing behavior of a subject which increases risk of transmitting said epidemic infectious disease to others, if said subject is infected;
      ii. generating for each said plurality of subjects a prioritization of the prophylactic treatment based on said score, said prioritization being higher with increasing risk of spreading said epidemic infectious disease;
      iii. receiving information from a server; and
      iv. displaying relevant prophylactically treating instructions to said subjects based on said received information;
   b. at least one server comprising a memory and a plurality of modules; said memory comprising instructions for:
      i. sending to said plurality of smart electronic devices information usable by a circuitry in said plurality of smart electronic devices to display said relevant prophylactically treating instructions.

21. The system according to claim 20, wherein said information comprises one or more of subject specific information.

22. The system according to claim 20, wherein said information comprises general information usable by a plurality of subjects and devices thereof.

23. The system according to claim 22, wherein said server is configured with instructions to receive scores for a plurality of said electronic devices and use said received scores to generate said general information, said electronic devices configured to use said general information to determine a relative treatment priority for their respective subjects.

24. The system according to claim 20, wherein said smart electronic devices comprise a proximity-detecting module using one or more of:
   a. physical proximity data received by means of electronic positioning data of said subject;
   b. a distance indicating sensor which indicates physical proximity of the location of a device in relation to the location of said another device; and
   c. historical location data.

25. The system according to claim 24, wherein said at least one server or said smart electronic devices comprise instructions to determine a prophylactically treating prioritization based on a propensity for proximity.

26. The system according to claim 25, wherein said determine said treatment prioritization further comprises one or more of:
   a. generating a score component based on a nature of a location where said physical proximity data is related;
   b. generating a score component comprising health data of the subject of one or both smart electronic devices;
   c. generating a score component comprising a profession of the subject of one or both smart electronic devices;
   d. generating a score component reflecting relative health risk to said subject if said subject contracts said epidemic infectious disease; and
   e. generating a score component reflecting damage to society if said subject contracts said epidemic infectious disease.

27. The system according to claim 25, wherein when said physical proximity data is related to a location that is either indoors or in a closed space, then said score of said subject of transmitting said epidemic infectious disease increases by a factor of between about 10 times to about 100 times.

28. The system according to claim 20, wherein said server comprises a simulation module configured to predict the effect of said prophylactic treatment on a disease spread.

29. An electronic device configured to be carried around by a plurality of subjects in a population for selecting subjects for prophylactically treating against an epidemic infectious disease said population having said plurality of subjects and configured with instructions to:
   i. determining a score for each said plurality of subjects based on behavior data collected using said electronic device, said behavior data representing behavior of a subject which increases risk of transmitting said epidemic infectious disease to others, if said subject is infected;
   ii. generating for each said plurality of subjects a prioritization of the prophylactic treatment based on said score, said prioritization being higher with increasing risk of spreading said epidemic infectious disease;
   iii. receiving information from a server; and
   iv. displaying relevant prophylactically treating instructions to said subjects based on said received information.

* * * * *